US007008781B1

(12) United States Patent
Davis et al.

(10) Patent No.: US 7,008,781 B1
(45) Date of Patent: Mar. 7, 2006

(54) METHOD OF ENHANCING THE BIOLOGICAL ACTIVITY OF LIGANDS

(75) Inventors: Samuel Davis, New York, NY (US); Nicholas W. Gale, Tarrytown, NY (US); George D. Yancopoulos, Yorktown Heights, NY (US); Neil Stahl, Carmel, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 09/868,677

(22) PCT Filed: Dec. 23, 1999

(86) PCT No.: PCT/US99/30900

§ 371 (c)(1),
(2), (4) Date: Oct. 1, 2001

(87) PCT Pub. No.: WO00/37642

PCT Pub. Date: Jun. 29, 2000

Related U.S. Application Data

(60) Provisional application No. 60/113,387, filed on Dec. 23, 1998.

(51) Int. Cl.
*C12N 15/18* (2006.01)
*C12N 15/62* (2006.01)

(52) U.S. Cl. .................. 435/69.7; 435/348; 435/254.2; 435/252.33; 435/360; 435/365.1; 435/320.1; 536/23.5; 530/399; 514/2; 514/12; 424/134.1; 424/192.1

(58) Field of Classification Search ................ 530/350, 530/351, 387.3; 536/23.5; 435/365, 320.1, 435/69.5, 325, 252.3, 358, 254.2, 348; 424/192.1
See application file for complete search history.

(56) References Cited

U.S. PATENT DOCUMENTS

| 5,521,073 | A |   | 5/1996  | Davis et al.      |         |
|-----------|---|---|---------|-------------------|---------|
| 5,580,757 | A | * | 12/1996 | Desnick et al.    | 435/69.7|
| 5,643,755 | A |   | 7/1997  | Davis et al.      |         |
| 5,650,490 | A |   | 7/1997  | Davis et al.      |         |
| 5,747,033 | A |   | 5/1998  | Davis et al.      |         |
| 5,814,478 | A |   | 9/1998  | Valenzuela et al. |         |
| 5,851,797 | A |   | 12/1998 | Valenzuela et al. |         |
| 5,879,672 | A |   | 3/1999  | Davis et al.      |         |
| 6,265,564 | B1| * | 7/2001  | Davis et al.      | 536/23.5|
| 6,337,387 | B1| * | 1/2002  | Sakano et al.     | 530/350 |

FOREIGN PATENT DOCUMENTS

| EP | 0816510     | 1/1998  |
|----|-------------|---------|
| WO | WO 92/03569 | 3/1992  |
| WO | WO 94/11020 | 5/1994  |
| WO | WO 95/27060 | 10/1995 |
| WO | WO 96/11269 | 4/1996  |
| WO | WO 96/31598 | 10/1996 |
| WO | WO 96/37621 | * 11/1996 |
| WO | WO 97/15667 | 5/1997  |
| WO | WO 97/48804 | 12/1997 |
| WO | WO 98/05779 | 2/1998  |

OTHER PUBLICATIONS

ONCOGENE, vol. 9, 1994, Henkemeyer, et al., "Immunolocalization of the Nuk receptor tyrosine kinase suggests roles in segmental patterning of the brain and axonogenesis" pp. 1001-1014.
SCIENCE, vol. 266, Nov. 4, 1994, Davis, et al., "Ligands for EPH-Related Receptor Tyrosine Kinases That Require Membrane Attachment or Clustering for Activity", pp. 816-819.
DNA Cell Biology, Aug. 1996 vol. 15, No. 8, Tournay C, et al., "Uptake of recombinant myeloperoxidase, free or fused to Fc-γ, by macrophages enhances killing activity towards micro-organisms", pp. 617-624.
Molecular and Cellular Biology, Sep. 1995, Bergemann, et al., "ELF-2, a New Member of the Eph Ligand Family, Is Segmentally Expressed in Mouse Embryos in the Region of the Hindbrain and Newly Forming Somites", pp. 4921-4929.
NEURON, vol. 17, Jul. 1996, Gale, et al., "Eph Receptors and Ligands Comprise Two Major Specificity Subclasses and Are Reciprocally Compartmentalized during Embryogenesis", pp. 9-19.
CELL, vol. 87, Dec. 27, 1996, Davis, et al., "Isolation of Angiopoietin-1, a Ligand for the TIE2 Receptor, by Secretion-Trap Expression Cloning", pp. 1161-1169.
CELL, vol. 90, 403-404, Aug. 8, 1997, Eph Nomenclature Committee, Letter to the Editor, "Unified Nomenclature for Eph Family Receptors and Their Ligands, the Ephrins", pp. 403-404.
Cell & Tissue Research, vol. 290, 1997, Gale, et al., "Ephrins and their receptors: a repulsive topic?", pp. 227-241.
SCIENCE, vol. 277, Jul. 4, 1997, Maisonpierre, et al., "Angiopoietin-2, a Natural Antagonist for Tie2 That Disrupts in vivo Angiogenesis", pp. 55-60.

* cited by examiner

*Primary Examiner*—Eileen B. O'Hara
(74) *Attorney, Agent, or Firm*—Valeta Gregg, Esq.

(57) ABSTRACT

Novel fusion polypeptide ligands that bind Eph family receptors or the Tie-2 receptor are identified, and methods for making the fusion polypeptide ligands in biologically active form are described. Nucleic acids encoding these novel fusion polypeptide ligands enable production of the fusion polypeptide ligands. The method of making the nucleic acids and the fusion polypeptide ligands is broadly applicable to the production of polypeptide ligands in general, resulting in improved affinity and/or increased activity of the ligand when compared to its native form.

15 Claims, 38 Drawing Sheets

Fig.1A.

```
              10          20          30          40
               *           *           *           *
ATG TCT GCA CTT CTG ATC CTA GCT CTT GTT GGA GCT GCA GTT GCT
Met Ser Ala Leu Leu Ile Leu Ala Leu Val Gly Ala Ala Val Ala>
___a___a___a___a_TRYPSIN SIGNAL SEQUENCE___a___a___a___a___>

50          60          70          80          90
        *           *           *           *           *
AGA GAC TGT GCA GAT GTA TAT CAA GCT GGT TTT AAT AAA AGT GGA
Arg Asp Cys Ala Asp Val Tyr Gln Ala Gly Phe Asn Lys Ser Gly>
___b___b___b___ANG1 FIBRINOGEN-LIKE DOMAIN_b___b___b___b___>

100         110         120         130
            *           *           *           *
ATC TAC ACT ATT TAT ATT AAT AAT ATG CCA GAA CCC AAA AAG GTG
Ile Tyr Thr Ile Tyr Ile Asn Asn Met Pro Glu Pro Lys Lys Val>
___b___b___b___ANG1 FIBRINOGEN-LIKE DOMAIN_b___b___b___b___>

140         150         160         170         180
        *           *           *           *           *
TTT TGC AAT ATG GAT GTC AAT GGG GGA GGT TGG ACT GTA ATA CAA
Phe Cys Asn Met Asp Val Asn Gly Gly Gly Trp Thr Val Ile Gln>
___b___b___b___ANG1 FIBRINOGEN-LIKE DOMAIN_b___b___b___b___>

190         200         210         220
            *           *           *           *
CAT CGT GAA GAT GGA AGT CTA GAT TTC CAA AGA GGC TGG AAG GAA
His Arg Glu Asp Gly Ser Leu Asp Phe Gln Arg Gly Trp Lys Glu>
___b___b___b___ANG1 FIBRINOGEN-LIKE DOMAIN_b___b___b___b___>

230         240         250         260         270
        *           *           *           *           *
TAT AAA ATG GGT TTT GGA AAT CCC TCC GGT GAA TAT TGG CTG GGG
Tyr Lys Met Gly Phe Gly Asn Pro Ser Gly Glu Tyr Trp Leu Gly>
___b___b___b___ANG1 FIBRINOGEN-LIKE DOMAIN_b___b___b___b___>

280         290         300         310
            *           *           *           *
AAT GAG TTT ATT TTT GCC ATT ACC AGT CAG AGG CAG TAC ATG CTA
Asn Glu Phe Ile Phe Ala Ile Thr Ser Gln Arg Gln Tyr Met Leu>
___b___b___b___ANG1 FIBRINOGEN-LIKE DOMAIN_b___b___b___b___>

320         330         340         350         360
        *           *           *           *           *
AGA ATT GAG TTA ATG GAC TGG GAA GGG AAC CGA GCC TAT TCA CAG
Arg Ile Glu Leu Met Asp Trp Glu Gly Asn Arg Ala Tyr Ser Gln>
___b___b___b___ANG1 FIBRINOGEN-LIKE DOMAIN_b___b___b___b___>

370         380         390         400
            *           *           *           *
TAT GAC AGA TTC CAC ATA GGA AAT GAA AAG CAA AAC TAT AGG TTG
Tyr Asp Arg Phe His Ile Gly Asn Glu Lys Gln Asn Tyr Arg Leu>
___b___b___b___ANG1 FIBRINOGEN-LIKE DOMAIN_b___b___b___b___>

410         420         430         440         450
        *           *           *           *           *
TAT TTA AAA GGT CAC ACT GGG ACA GCA GGA AAA CAG AGC AGC CTG
Tyr Leu Lys Gly His Thr Gly Thr Ala Gly Lys Gln Ser Ser Leu>
___b___b___b___ANG1 FIBRINOGEN-LIKE DOMAIN_b___b___b___b___>
```

Fig. 1B

```
              460             470             480             490
               *       *       *       *       *       *       *       *
ATC TTA CAC GGT GCT GAT TTC AGC ACT AAA GAT GCT GAT AAT GAC
Ile Leu His Gly Ala Asp Phe Ser Thr Lys Asp Ala Asp Asn Asp>
___b___b___b___ANG1 FIBRINOGEN-LIKE DOMAIN_b___b___b___b___>

500             510             520             530             540
               *       *       *       *       *       *       *       *       *
AAC TGT ATG TGC AAA TGT GCC CTC ATG TTA ACA GGA GGA TGG TGG
Asn Cys Met Cys Lys Cys Ala Leu Met Leu Thr Gly Gly Trp Trp>
___b___b___b___ANG1 FIBRINOGEN-LIKE DOMAIN_b___b___b___b___>

550             560             570             580
               *       *       *       *       *       *       *       *
TTT GAT GCT TGT GGC CCC TCC AAT CTA AAT GGA ATG TTC TAT ACT
Phe Asp Ala Cys Gly Pro Ser Asn Leu Asn Gly Met Phe Tyr Thr>
___b___b___b___ANG1 FIBRINOGEN-LIKE DOMAIN_b___b___b___b___>

590             600             610             620             630
               *       *       *       *       *       *       *       *       *
GCG GGA CAA AAC CAT GGA AAA CTG AAT GGG ATA AAG TGG CAC TAC
Ala Gly Gln Asn His Gly Lys Leu Asn Gly Ile Lys Trp His Tyr>
___b___b___b___ANG1 FIBRINOGEN-LIKE DOMAIN_b___b___b___b___>

640             650             660             670
               *       *       *       *       *       *       *       *
TTC AAA GGG CCC AGT TAC TCC TTA CGT TCC ACA ACT ATG ATG ATT
Phe Lys Gly Pro Ser Tyr Ser Leu Arg Ser Thr Thr Met Met Ile>
___b___b___b___ANG1 FIBRINOGEN-LIKE DOMAIN_b___b___b___b___>

680             690             700             710             720
               *       *       *       *       *       *       *       *       *
CGA CCT TTA GAT TTT GGC CCC GCG CCT TTT AGA GAC TGT GCA GAT
Arg Pro Leu Asp Phe>
___ANG1 FIBRINO____>
                        Gly Pro Ala Pro>
                        ___GPAP BRI____>
                                        Phe Arg Asp Cys Ala Asp>
                                        ___ANG1 FIBRINOGEN-____>

730             740             750             760
               *       *       *       *       *       *       *       *
GTA TAT CAA GCT GGT TTT AAT AAA AGT GGA ATC TAC ACT ATT TAT
Val Tyr Gln Ala Gly Phe Asn Lys Ser Gly Ile Tyr Thr Ile Tyr>
___d___d___d___ANG1 FIBRINOGEN-LIKE DOMAIN_d___d___d___d___>

770             780             790             800             810
               *       *       *       *       *       *       *       *       *
ATT AAT AAT ATG CCA GAA CCC AAA AAG GTG TTT TGC AAT ATG GAT
Ile Asn Asn Met Pro Glu Pro Lys Lys Val Phe Cys Asn Met Asp>
___d___d___d___ANG1 FIBRINOGEN-LIKE DOMAIN_d___d___d___d___>

820             830             840             850
               *       *       *       *       *       *       *       *
GTC AAT GGG GGA GGT TGG ACT GTA ATA CAA CAT CGT GAA GAT GGA
Val Asn Gly Gly Gly Trp Thr Val Ile Gln His Arg Glu Asp Gly>
___d___d___d___ANG1 FIBRINOGEN-LIKE DOMAIN_d___d___d___d___>
```

Fig.1C.

```
       860           870           880           890           900
        *    *    *    *    *    *    *    *    *
       AGT  CTA  GAT  TTC  CAA  AGA  GGC  TGG  AAG  GAA  TAT  AAA  ATG  GGT  TTT
       Ser  Leu  Asp  Phe  Gln  Arg  Gly  Trp  Lys  Glu  Tyr  Lys  Met  Gly  Phe>
       ___d____d____d___ANG1 FIBRINOGEN-LIKE DOMAIN_d____d____d____d___>

910           920           930           940
             *    *    *    *    *    *    *    *    *
            GGA  AAT  CCC  TCC  GGT  GAA  TAT  TGG  CTG  GGG  AAT  GAG  TTT  ATT  TTT
            Gly  Asn  Pro  Ser  Gly  Glu  Tyr  Trp  Leu  Gly  Asn  Glu  Phe  Ile  Phe>
            ___d____d____d___ANG1 FIBRINOGEN-LIKE DOMAIN_d____d____d____d___>

950           960           970           980           990
        *    *    *    *    *    *    *    *    *
       GCC  ATT  ACC  AGT  CAG  AGG  CAG  TAC  ATG  CTA  AGA  ATT  GAG  TTA  ATG
       Ala  Ile  Thr  Ser  Gln  Arg  Gln  Tyr  Met  Leu  Arg  Ile  Glu  Leu  Met>
       ___d____d____d___ANG1 FIBRINOGEN-LIKE DOMAIN_d____d____d____d___>

1000          1010          1020          1030
             *    *    *    *    *    *    *    *    *
            GAC  TGG  GAA  GGG  AAC  CGA  GCC  TAT  TCA  CAG  TAT  GAC  AGA  TTC  CAC
            Asp  Trp  Glu  Gly  Asn  Arg  Ala  Tyr  Ser  Gln  Tyr  Asp  Arg  Phe  His>
            ___d____d____d___ANG1 FIBRINOGEN-LIKE DOMAIN_d____d____d____d___>

1040          1050          1060          1070          1080
        *    *    *    *    *    *    *    *    *
       ATA  GGA  AAT  GAA  AAG  CAA  AAC  TAT  AGG  TTG  TAT  TTA  AAA  GGT  CAC
       Ile  Gly  Asn  Glu  Lys  Gln  Asn  Tyr  Arg  Leu  Tyr  Leu  Lys  Gly  His>
       ___d____d____d___ANG1 FIBRINOGEN-LIKE DOMAIN_d____d____d____d___>

1090          1100          1110          1120
             *    *    *    *    *    *    *    *    *
            ACT  GGG  ACA  GCA  GGA  AAA  CAG  AGC  AGC  CTG  ATC  TTA  CAC  GGT  GCT
            Thr  Gly  Thr  Ala  Gly  Lys  Gln  Ser  Ser  Leu  Ile  Leu  His  Gly  Ala>
            ___d____d____d___ANG1 FIBRINOGEN-LIKE DOMAIN_d____d____d____d___>

1130          1140          1150          1160          1170
        *    *    *    *    *    *    *    *    *
       GAT  TTC  AGC  ACT  AAA  GAT  GCT  GAT  AAT  GAC  AAC  TGT  ATG  TGC  AAA
       Asp  Phe  Ser  Thr  Lys  Asp  Ala  Asp  Asn  Asp  Asn  Cys  Met  Cys  Lys>
       ___d____d____d___ANG1 FIBRINOGEN-LIKE DOMAIN_d____d____d____d___>

1180          1190          1200          1210
             *    *    *    *    *    *    *    *    *
            TGT  GCC  CTC  ATG  TTA  ACA  GGA  GGA  TGG  TGG  TTT  GAT  GCT  TGT  GGC
            Cys  Ala  Leu  Met  Leu  Thr  Gly  Gly  Trp  Trp  Phe  Asp  Ala  Cys  Gly>
            ___d____d____d___ANG1 FIBRINOGEN-LIKE DOMAIN_d____d____d____d___>

1220          1230          1240          1250          1260
        *    *    *    *    *    *    *    *    *
       CCC  TCC  AAT  CTA  AAT  GGA  ATG  TTC  TAT  ACT  GCG  GGA  CAA  AAC  CAT
       Pro  Ser  Asn  Leu  Asn  Gly  Met  Phe  Tyr  Thr  Ala  Gly  Gln  Asn  His>
       ___d____d____d___ANG1 FIBRINOGEN-LIKE DOMAIN_d____d____d____d___>
```

Fig.1D.

```
            1270          1280          1290          1300
              *     *       *     *       *     *       *     *     *
          GGA AAA CTG AAT GGG ATA AAG TGG CAC TAC TTC AAA GGG CCC AGT
          Gly Lys Leu Asn Gly Ile Lys Trp His Tyr Phe Lys Gly Pro Ser>
          ___d___d___d__ANG1 FIBRINOGEN-LIKE DOMAIN_d___d___d___d___>

1310          1320          1330          1340          1350
              *     *       *     *       *     *       *     *       *     *
          TAC TCC TTA CGT TCC ACA ACT ATG ATG ATT CGA CCT TTA GAT TTT
          Tyr Ser Leu Arg Ser Thr Thr Met Met Ile Arg Pro Leu Asp Phe>
          ___d___d___d__ANG1 FIBRINOGEN-LIKE DOMAIN_d___d___d___d___>

1360          1370         1380          1390
                     *     *       *     *      *     *       *     *     *
          GGA CCG GGC GAG CCC AAA TCT TGT GAC AAA ACT CAC ACA TGC CCA
          Gly Pro Gly>
          ___e___e___>
                      Glu Pro Lys Ser Cys Asp Lys Thr His Thr Cys Pro>
                      ___f___f___f____FC TAG [SPLIT]_f___f___f___f___>

1400          1410          1420          1430          1440
              *     *       *     *       *     *       *     *       *     *
          CCG TGC CCA GCA CCT GAA CTC CTG GGG GGA CCG TCA GTC TTC CTC
          Pro Cys Pro Ala Pro Glu Leu Leu Gly Gly Pro Ser Val Phe Leu>
          ___f___f___f___f___f_FC TAG [SPLIT]___f___f___f___f___f___>

1450          1460          1470          1480
                     *     *       *     *       *     *       *     *
          TTC CCC CCA AAA CCC AAG GAC ACC CTC ATG ATC TCC CGG ACC CCT
          Phe Pro Pro Lys Pro Lys Asp Thr Leu Met Ile Ser Arg Thr Pro>
          ___f___f___f___f___f_FC TAG [SPLIT]___f___f___f___f___f___>

1490          1500          1510          1520          1530
              *     *       *     *       *     *       *     *       *
          GAG GTC ACA TGC GTG GTG GTG GAC GTG AGC CAC GAA GAC CCT GAG
          Glu Val Thr Cys Val Val Val Asp Val Ser His Glu Asp Pro Glu>
          ___f___f___f___f___f_FC TAG [SPLIT]___f___f___f___f___f___>

1540          1550          1560          1570
                     *     *       *     *       *     *       *     *     *
          GTC AAG TTC AAC TGG TAC GTG GAC GGC GTG GAG GTG CAT AAT GCC
          Val Lys Phe Asn Trp Tyr Val Asp Gly Val Glu Val His Asn Ala>
          ___f___f___f___f___f_FC TAG [SPLIT]___f___f___f___f___f___>

1580          1590          1600          1610          1620
              *     *       *     *       *     *       *     *       *
          AAG ACA AAG CCG CGG GAG GAG CAG TAC AAC AGC ACG TAC CGT GTG
          Lys Thr Lys Pro Arg Glu Glu Gln Tyr Asn Ser Thr Tyr Arg Val>
          ___f___f___f___f___f_FC TAG [SPLIT]___f___f___f___f___f___>

1630          1640          1650          1660
                     *     *       *     *       *     *       *     *
          GTC AGC GTC CTC ACC GTC CTG CAC CAG GAC TGG CTG AAT GGC AAG
          Val Ser Val Leu Thr Val Leu His Gln Asp Trp Leu Asn Gly Lys>
          ___f___f___f___f___f_FC TAG [SPLIT]___f___f___f___f___f___>
```

Fig. 1E.

```
         1670          1680          1690          1700          1710
           *     *      *     *       *     *      *     *      *
       GAG TAC AAG TGC AAG GTC TCC AAC AAA GCC CTC CCA GCC CCC ATC
       Glu Tyr Lys Cys Lys Val Ser Asn Lys Ala Leu Pro Ala Pro Ile>
       ___f___f___f___f___f__FC TAG [SPLIT]___f___f___f___f___f___>

1720          1730          1740          1750
           *     *      *     *       *     *      *     *
       GAG AAA ACC ATC TCC AAA GCC AAA GGG CAG CCC CGA GAA CCA CAG
       Glu Lys Thr Ile Ser Lys Ala Lys Gly Gln Pro Arg Glu Pro Gln>
       ___f___f___f___f___f__FC TAG [SPLIT]___f___f___f___f___f___>

1760          1770          1780          1790          1800
           *     *      *     *       *     *      *     *      *
       GTG TAC ACC CTG CCC CCA TCC CGG GAT GAG CTG ACC AAG AAC CAG
       Val Tyr Thr Leu Pro Pro Ser Arg Asp Glu Leu Thr Lys Asn Gln>
       ___f___f___f___f___f__FC TAG [SPLIT]___f___f___f___f___f___>

1810          1820          1830          1840
           *     *      *     *       *     *      *     *
       GTC AGC CTG ACC TGC CTG GTC AAA GGC TTC TAT CCC AGC GAC ATC
       Val Ser Leu Thr Cys Leu Val Lys Gly Phe Tyr Pro Ser Asp Ile>
       ___f___f___f___f___f__FC TAG [SPLIT]___f___f___f___f___f___>

1850          1860          1870          1880          1890
           *     *      *     *       *     *      *     *      *
       GCC GTG GAG TGG GAG AGC AAT GGG CAG CCG GAG AAC AAC TAC AAG
       Ala Val Glu Trp Glu Ser Asn Gly Gln Pro Glu Asn Asn Tyr Lys>
       ___f___f___f___f___f__FC TAG [SPLIT]___f___f___f___f___f___>

1900          1910          1920          1930
           *     *      *     *       *     *      *     *
       ACC ACG CCT CCC GTG CTG GAC TCC GAC GGC TCC TTC TTC CTC TAC
       Thr Thr Pro Pro Val Leu Asp Ser Asp Gly Ser Phe Phe Leu Tyr>
       ___f___f___f___f___f__FC TAG [SPLIT]___f___f___f___f___f___>

1940          1950          1960          1970          1980
           *     *      *     *       *     *      *     *      *
       AGC AAG CTC ACC GTG GAC AAG AGC AGG TGG CAG CAG GGG AAC GTC
       Ser Lys Leu Thr Val Asp Lys Ser Arg Trp Gln Gln Gly Asn Val>
       ___f___f___f___f___f__FC TAG [SPLIT]___f___f___f___f___f___>

1990          2000          2010          2020
           *     *      *     *       *     *      *     *
       TTC TCA TGC TCC GTG ATG CAT GAG GCT CTG CAC AAC CAC TAC ACG
       Phe Ser Cys Ser Val Met His Glu Ala Leu His Asn His Tyr Thr>
       ___f___f___f___f___f__FC TAG [SPLIT]___f___f___f___f___f___>

2030          2040          2050
           *     *      *     *       *     *
       CAG AAG AGC CTC TCC CTG TCT CCG GGT AAA TGA
       Gln Lys Ser Leu Ser Leu Ser Pro Gly Lys ***>
       ___f___f___f__FC TAG [SPLIT]___f___f___f___>
```

Fig.2A.

```
          10           20           30           40
           .            .            .            .
ATG TCT GCA CTT CTG ATC CTA GCT CTT GTT GGA GCT GCA GTT GCT
Met Ser Ala Leu Leu Ile Leu Ala Leu Val Gly Ala Ala Val Ala>
___a___a___a___a_TRYPSIN SIGNAL SEQUENCE___a___a___a___a___>

50           60           70           80           90
      .            .            .            .            .
AGA GAC TGT GCT GAA GTA TTC AAA TCA GGA CAC ACC ACA AAT GGC
Arg Asp Cys Ala Glu Val Phe Lys Ser Gly His Thr Thr Asn Gly>
___b___b___b__ANG2 FIBRINOGEN-LIKE DOMAIN #1___b___b___b___>

100          110          120          130
           .            .            .            .
ATC TAC ACG TTA ACA TTC CCT AAT TCT ACA GAA GAG ATC AAG GCC
Ile Tyr Thr Leu Thr Phe Pro Asn Ser Thr Glu Glu Ile Lys Ala>
___b___b___b__ANG2 FIBRINOGEN-LIKE DOMAIN #1___b___b___b___>

140          150          160          170          180
       .            .            .            .            .
TAC TGT GAC ATG GAA GCT GGA GGA GGC GGG TGG ACA ATT ATT CAG
Tyr Cys Asp Met Glu Ala Gly Gly Gly Gly Trp Thr Ile Ile Gln>
___b___b___b__ANG2 FIBRINOGEN-LIKE DOMAIN #1___b___b___b___>

190          200          210          220
           .            .            .            .
CGA CGT GAG GAT GGC AGC GTT GAT TTT CAG AGG ACT TGG AAA GAA
Arg Arg Glu Asp Gly Ser Val Asp Phe Gln Arg Thr Trp Lys Glu>
___b___b___b__ANG2 FIBRINOGEN-LIKE DOMAIN #1___b___b___b___>

230          240          250          260          270
       .            .            .            .            .
TAT AAA GTG GGA TTT GGT AAC CCT TCA GGA GAA TAT TGG CTG GGA
Tyr Lys Val Gly Phe Gly Asn Pro Ser Gly Glu Tyr Trp Leu Gly>
___b___b___b__ANG2 FIBRINOGEN-LIKE DOMAIN #1___b___b___b___>

280          290          300          310
           .            .            .            .
AAT GAG TTT GTT TCG CAA CTG ACT AAT CAG CAA CGC TAT GTG CTT
Asn Glu Phe Val Ser Gln Leu Thr Asn Gln Gln Arg Tyr Val Leu>
___b___b___b__ANG2 FIBRINOGEN-LIKE DOMAIN #1___b___b___b___>

320          330          340          350          360
       .            .            .            .            .
AAA ATA CAC CTT AAA GAC TGG GAA GGG AAT GAG GCT TAC TCA TTG
Lys Ile His Leu Lys Asp Trp Glu Gly Asn Glu Ala Tyr Ser Leu>
___b___b___b__ANG2 FIBRINOGEN-LIKE DOMAIN #1___b___b___b___>

370          380          390          400
           .            .            .            .
TAT GAA CAT TTC TAT CTC TCA AGT GAA GAA CTC AAT TAT AGG ATT
Tyr Glu His Phe Tyr Leu Ser Ser Glu Glu Leu Asn Tyr Arg Ile>
___b___b___b__ANG2 FIBRINOGEN-LIKE DOMAIN #1___b___b___b___>

410          420          430          440          450
       .            .            .            .            .
CAC CTT AAA GGA CTT ACA GGG ACA GCC GGC AAA ATA AGC AGC ATC
His Leu Lys Gly Leu Thr Gly Thr Ala Gly Lys Ile Ser Ser Ile>
___b___b___b__ANG2 FIBRINOGEN-LIKE DOMAIN #1___b___b___b___>
```

Fig.2B.

```
              460         470         480         490
               *           *           *           *
AGC CAA CCA GGA AAT GAT TTT AGC ACA AAG GAT GGA GAC AAC GAC
Ser Gln Pro Gly Asn Asp Phe Ser Thr Lys Asp Gly Asp Asn Asp>
___b___b___b__ANG2 FIBRINOGEN-LIKE DOMAIN #1___b___b___b___>

500         510         520         530         540
          *           *           *           *           *
AAA TGT ATT TGC AAA TGT TCA CAA ATG CTA ACA GGA GGC TGG TGG
Lys Cys Ile Cys Lys Cys Ser Gln Met Leu Thr Gly Gly Trp Trp>
___b___b___b__ANG2 FIBRINOGEN-LIKE DOMAIN #1___b___b___b___>

550         560         570         580
               *           *           *           *
TTT GAT GCA TGT GGT CCT TCC AAC TTG AAC GGA ATG TAC TAT CCA
Phe Asp Ala Cys Gly Pro Ser Asn Leu Asn Gly Met Tyr Tyr Pro>
___b___b___b__ANG2 FIBRINOGEN-LIKE DOMAIN #1___b___b___b___>

590         600         610         620         630
          *           *           *           *           *
CAG AGG CAG AAC ACA AAT AAG TTC AAC GGC ATT AAA TGG TAC TAC
Gln Arg Gln Asn Thr Asn Lys Phe Asn Gly Ile Lys Trp Tyr Tyr>
___b___b___b__ANG2 FIBRINOGEN-LIKE DOMAIN #1___b___b___b___>

640         650         660         670
               *           *           *           *
TGG AAA GGC TCA GGC TAT TCG CTC AAG GCC ACA ACC ATG ATG ATC
Trp Lys Gly Ser Gly Tyr Ser Leu Lys Ala Thr Thr Met Met Ile>
___b___b___b__ANG2 FIBRINOGEN-LIKE DOMAIN #1___b___b___b___>

680         690         700         710         720
          *           *           *           *           *
CGA CCA GCA GAT TTC GGG GGC CCC GCG CCT TTC AGA GAC TGT GCT
Arg Pro Ala Asp Phe>
___ANG2 FIBRINO____>
                    Gly Gly Pro Ala Pro>
                    ___GGPAP BRIDGE____>
                                        Phe Arg Asp Cys Ala>
                                        ___ANG2 FIBRINO____>

730         740         750         760
               *           *           *           *
GAA GTA TTC AAA TCA GGA CAC ACC ACA AAT GGC ATC TAC ACG TTA
Glu Val Phe Lys Ser Gly His Thr Thr Asn Gly Ile Tyr Thr Leu>
___d___d___d__ANG2 FIBRINOGEN-LIKE DOMAIN#2____d___d___d___>

770         780         790         800         810
          *           *           *           *           *
ACA TTC CCT AAT TCT ACA GAA GAG ATC AAG GCC TAC TGT GAC ATG
Thr Phe Pro Asn Ser Thr Glu Glu Ile Lys Ala Tyr Cys Asp Met>
___d___d___d__ANG2 FIBRINOGEN-LIKE DOMAIN#2____d___d___d___>

820         830         840         850
               *           *           *           *
GAA GCT GGA GGA GGC GGG TGG ACA ATT ATT CAG CGA CGT GAG GAT
Glu Ala Gly Gly Gly Gly Trp Thr Ile Ile Gln Arg Arg Glu Asp>
___d___d___d__ANG2 FIBRINOGEN-LIKE DOMAIN#2____d___d___d___>
```

Fig.2C.

```
       860         870         880         890         900
        *     *     *     *     *     *     *     *     *
GGC AGC GTT GAT TTT CAG AGG ACT TGG AAA GAA TAT AAA GTG GGA
Gly Ser Val Asp Phe Gln Arg Thr Trp Lys Glu Tyr Lys Val Gly>
___d___d___d__ANG2 FIBRINOGEN-LIKE DOMAIN#2____d___d___d___>

910         920         930         940
        *     *     *     *     *     *     *     *
TTT GGT AAC CCT TCA GGA GAA TAT TGG CTG GGA AAT GAG TTT GTT
Phe Gly Asn Pro Ser Gly Glu Tyr Trp Leu Gly Asn Glu Phe Val>
___d___d___d__ANG2 FIBRINOGEN-LIKE DOMAIN#2____d___d___d___>

950         960         970         980         990
        *     *     *     *     *     *     *     *     *
TCG CAA CTG ACT AAT CAG CAA CGC TAT GTG CTT AAA ATA CAC CTT
Ser Gln Leu Thr Asn Gln Gln Arg Tyr Val Leu Lys Ile His Leu>
___d___d___d__ANG2 FIBRINOGEN-LIKE DOMAIN#2____d___d___d___>

1000        1010        1020        1030
        *     *     *     *     *     *     *     *
AAA GAC TGG GAA GGG AAT GAG GCT TAC TCA TTG TAT GAA CAT TTC
Lys Asp Trp Glu Gly Asn Glu Ala Tyr Ser Leu Tyr Glu His Phe>
___d___d___d__ANG2 FIBRINOGEN-LIKE DOMAIN#2____d___d___d___>

1040        1050        1060        1070        1080
        *     *     *     *     *     *     *     *     *
TAT CTC TCA AGT GAA GAA CTC AAT TAT AGG ATT CAC CTT AAA GGA
Tyr Leu Ser Ser Glu Glu Leu Asn Tyr Arg Ile His Leu Lys Gly>
___d___d___d__ANG2 FIBRINOGEN-LIKE DOMAIN#2____d___d___d___>

1090        1100        1110        1120
        *     *     *     *     *     *     *     *
CTT ACA GGG ACA GCC GGC AAA ATA AGC AGC ATC AGC CAA CCA GGA
Leu Thr Gly Thr Ala Gly Lys Ile Ser Ser Ile Ser Gln Pro Gly>
___d___d___d__ANG2 FIBRINOGEN-LIKE DOMAIN#2____d___d___d___>

1130        1140        1150        1160        1170
        *     *     *     *     *     *     *     *     *
AAT GAT TTT AGC ACA AAG GAT GGA GAC AAC GAC AAA TGT ATT TGC
Asn Asp Phe Ser Thr Lys Asp Gly Asp Asn Asp Lys Cys Ile Cys>
___d___d___d__ANG2 FIBRINOGEN-LIKE DOMAIN#2____d___d___d___>

1180        1190        1200        1210
        *     *     *     *     *     *     *     *
AAA TGT TCA CAA ATG CTA ACA GGA GGC TGG TGG TTT GAT GCA TGT
Lys Cys Ser Gln Met Leu Thr Gly Gly Trp Trp Phe Asp Ala Cys>
___d___d___d__ANG2 FIBRINOGEN-LIKE DOMAIN#2____d___d___d___>

1220        1230        1240        1250        1260
        *     *     *     *     *     *     *     *     *
GGT CCT TCC AAC TTG AAC GGA ATG TAC TAT CCA CAG AGG CAG AAC
Gly Pro Ser Asn Leu Asn Gly Met Tyr Tyr Pro Gln Arg Gln Asn>
___d___d___d__ANG2 FIBRINOGEN-LIKE DOMAIN#2____d___d___d___>
```

Fig.2D.

```
          1270        1280        1290        1300
            *           *           *           *
ACA AAT AAG TTC AAC GGC ATT AAA TGG TAC TAC TGG AAA GGC TCA
Thr Asn Lys Phe Asn Gly Ile Lys Trp Tyr Tyr Trp Lys Gly Ser>
___d___d___d__ANG2 FIBRINOGEN-LIKE DOMAIN#2____d___d___d___>

1310        1320        1330        1340        1350
       *           *           *           *           *
GGC TAT TCG CTC AAG GCC ACA ACC ATG ATG ATC CGA CCA GCA GAT
Gly Tyr Ser Leu Lys Ala Thr Thr Met Met Ile Arg Pro Ala Asp>
___d___d___d__ANG2 FIBRINOGEN-LIKE DOMAIN#2____d___d___d___>

1360        1370        1380        1390
            *           *           *           *
TTC GGA CCG GGC GAG CCC AAA TCT TGT GAC AAA ACT CAC ACA TGC
Phe>
___>
    Gly Pro Gly>
    __e___e___>
              Glu Pro Lys Ser Cys Asp Lys Thr His Thr Cys>
              ___f___f___f___f__FC TAG___f___f___f___f___>

1400        1410        1420        1430        1440
       *           *           *           *           *
CCA CCG TGC CCA GCA CCT GAA CTC CTG GGG GGA CCG TCA GTC TTC
Pro Pro Cys Pro Ala Pro Glu Leu Leu Gly Gly Pro Ser Val Phe>
___f___f___f___f___f___f__FC TAG___f___f___f___f___f___f___>

1450        1460        1470        1480
            *           *           *           *
CTC TTC CCC CCA AAA CCC AAG GAC ACC CTC ATG ATC TCC CGG ACC
Leu Phe Pro Pro Lys Pro Lys Asp Thr Leu Met Ile Ser Arg Thr>
___f___f___f___f___f___f__FC TAG___f___f___f___f___f___f___>

1490        1500        1510        1520        1530
       *           *           *           *           *
CCT GAG GTC ACA TGC GTG GTG GTG GAC GTG AGC CAC GAA GAC CCT
Pro Glu Val Thr Cys Val Val Val Asp Val Ser His Glu Asp Pro>
___f___f___f___f___f___f__FC TAG___f___f___f___f___f___f___>

1540        1550        1560        1570
            *           *           *           *
GAG GTC AAG TTC AAC TGG TAC GTG GAC GGC GTG GAG GTG CAT AAT
Glu Val Lys Phe Asn Trp Tyr Val Asp Gly Val Glu Val His Asn>
___f___f___f___f___f___f__FC TAG___f___f___f___f___f___f___>

1580        1590        1600        1610        1620
       *           *           *           *           *
GCC AAG ACA AAG CCG CGG GAG GAG CAG TAC AAC AGC ACG TAC CGT
Ala Lys Thr Lys Pro Arg Glu Glu Gln Tyr Asn Ser Thr Tyr Arg>
___f___f___f___f___f___f__FC TAG___f___f___f___f___f___f___>

1630        1640        1650        1660
            *           *           *           *
GTG GTC AGC GTC CTC ACC GTC CTG CAC CAG GAC TGG CTG AAT GGC
Val Val Ser Val Leu Thr Val Leu His Gln Asp Trp Leu Asn Gly>
___f___f___f___f___f___f__FC TAG___f___f___f___f___f___f___>
```

Fig.2E.

```
           1670          1680          1690          1700          1710
             *     *       *     *       *     *       *     *       *
        AAG GAG TAC AAG TGC AAG GTC TCC AAC AAA GCC CTC CCA GCC CCC
        Lys Glu Tyr Lys Cys Lys Val Ser Asn Lys Ala Leu Pro Ala Pro>
        ___f___f___f___f___f___f__FC TAG___f___f___f___f___f___f___>

1720          1730          1740          1750
             *     *       *     *       *     *       *     *       *
        ATC GAG AAA ACC ATC TCC AAA GCC AAA GGG CAG CCC CGA GAA CCA
        Ile Glu Lys Thr Ile Ser Lys Ala Lys Gly Gln Pro Arg Glu Pro>
        ___f___f___f___f___f___f__FC TAG___f___f___f___f___f___f___>

1760          1770          1780          1790          1800
             *     *       *     *       *     *       *     *       *
        CAG GTG TAC ACC CTG CCC CCA TCC CGG GAT GAG CTG ACC AAG AAC
        Gln Val Tyr Thr Leu Pro Pro Ser Arg Asp Glu Leu Thr Lys Asn>
        ___f___f___f___f___f___f__FC TAG___f___f___f___f___f___f___>

1810          1820          1830          1840
             *     *       *     *       *     *       *     *       *
        CAG GTC AGC CTG ACC TGC CTG GTC AAA GGC TTC TAT CCC AGC GAC
        Gln Val Ser Leu Thr Cys Leu Val Lys Gly Phe Tyr Pro Ser Asp>
        ___f___f___f___f___f___f__FC TAG___f___f___f___f___f___f___>

1850          1860          1870          1880          1890
             *     *       *     *       *     *       *     *       *
        ATC GCC GTG GAG TGG GAG AGC AAT GGG CAG CCG GAG AAC AAC TAC
        Ile Ala Val Glu Trp Glu Ser Asn Gly Gln Pro Glu Asn Asn Tyr>
        ___f___f___f___f___f___f__FC TAG___f___f___f___f___f___f___>

1900          1910          1920          1930
             *     *       *     *       *     *       *     *       *
        AAG ACC ACG CCT CCC GTG CTG GAC TCC GAC GGC TCC TTC TTC CTC
        Lys Thr Thr Pro Pro Val Leu Asp Ser Asp Gly Ser Phe Phe Leu>
        ___f___f___f___f___f___f__FC TAG___f___f___f___f___f___f___>

1940          1950          1960          1970          1980
             *     *       *     *       *     *       *     *       *
        TAC AGC AAG CTC ACC GTG GAC AAG AGC AGG TGG CAG CAG GGG AAC
        Tyr Ser Lys Leu Thr Val Asp Lys Ser Arg Trp Gln Gln Gly Asn>
        ___f___f___f___f___f___f__FC TAG___f___f___f___f___f___f___>

1990          2000          2010          2020
             *     *       *     *       *     *       *     *       *
        GTC TTC TCA TGC TCC GTG ATG CAT GAG GCT CTG CAC AAC CAC TAC
        Val Phe Ser Cys Ser Val Met His Glu Ala Leu His Asn His Tyr>
        ___f___f___f___f___f___f__FC TAG___f___f___f___f___f___f___>

2030          2040          2050          2060
             *     *       *     *       *     *       *     *
        ACG CAG AAG AGC CTC TCC CTG TCT CCG GGT AAA TGA
        Thr Gln Lys Ser Leu Ser Leu Ser Pro Gly Lys ***>
        ___f___f___f___f____FC TAG_f___f___f___f___f___>
```

Fig.3A.

```
            10              20              30              40
             *       *       *       *       *       *       *       *
ATG TCT GCA CTT CTG ATC CTA GCT CTT GTT GGA GCT GCA GTT GCT
Met Ser Ala Leu Leu Ile Leu Ala Leu Val Gly Ala Ala Val Ala>
___a___a___a___a_TRYPSIN SIGNAL SEQUENCE___a___a___a___a___>

50              60              70              80              90
             *       *       *       *       *       *       *       *       *
AGA GAC TGT GCA GAT GTA TAT CAA GCT GGT TTT AAT AAA AGT GGA
Arg Asp Cys Ala Asp Val Tyr Gln Ala Gly Phe Asn Lys Ser Gly>
___b___b___b___ANG1 FIBRINOGEN-LIKE DOMAIN_b___b___b___b___>

100             110             120             130
             *       *       *       *       *       *       *       *       *
ATC TAC ACT ATT TAT ATT AAT AAT ATG CCA GAA CCC AAA AAG GTG
Ile Tyr Thr Ile Tyr Ile Asn Asn Met Pro Glu Pro Lys Lys Val>
___b___b___b___ANG1 FIBRINOGEN-LIKE DOMAIN_b___b___b___b___>

140             150             160             170             180
             *       *       *       *       *       *       *       *       *
TTT TGC AAT ATG GAT GTC AAT GGG GGA GGT TGG ACT GTA ATA CAA
Phe Cys Asn Met Asp Val Asn Gly Gly Gly Trp Thr Val Ile Gln>
___b___b___b___ANG1 FIBRINOGEN-LIKE DOMAIN_b___b___b___b___>

190             200             210             220
             *       *       *       *       *       *       *       *       *
CAT CGT GAA GAT GGA AGT CTA GAT TTC CAA AGA GGC TGG AAG GAA
His Arg Glu Asp Gly Ser Leu Asp Phe Gln Arg Gly Trp Lys Glu>
___b___b___b___ANG1 FIBRINOGEN-LIKE DOMAIN_b___b___b___b___>

230             240             250             260             270
             *       *       *       *       *       *       *       *       *
TAT AAA ATG GGT TTT GGA AAT CCC TCC GGT GAA TAT TGG CTG GGG
Tyr Lys Met Gly Phe Gly Asn Pro Ser Gly Glu Tyr Trp Leu Gly>
___b___b___b___ANG1 FIBRINOGEN-LIKE DOMAIN_b___b___b___b___>

280             290             300             310
             *       *       *       *       *       *       *       *       *
AAT GAG TTT ATT TTT GCC ATT ACC AGT CAG AGG CAG TAC ATG CTA
Asn Glu Phe Ile Phe Ala Ile Thr Ser Gln Arg Gln Tyr Met Leu>
___b___b___b___ANG1 FIBRINOGEN-LIKE DOMAIN_b___b___b___b___>

320             330             340             350             360
             *       *       *       *       *       *       *       *       *
AGA ATT GAG TTA ATG GAC TGG GAA GGG AAC CGA GCC TAT TCA CAG
Arg Ile Glu Leu Met Asp Trp Glu Gly Asn Arg Ala Tyr Ser Gln>
___b___b___b___ANG1 FIBRINOGEN-LIKE DOMAIN_b___b___b___b___>

370             380             390             400
             *       *       *       *       *       *       *       *       *
TAT GAC AGA TTC CAC ATA GGA AAT GAA AAG CAA AAC TAT AGG TTG
Tyr Asp Arg Phe His Ile Gly Asn Glu Lys Gln Asn Tyr Arg Leu>
___b___b___b___ANG1 FIBRINOGEN-LIKE DOMAIN_b___b___b___b___>
```

Fig.3B.

```
       410         420         430         440         450
        *           *           *           *           *
       TAT TTA AAA GGT CAC ACT GGG ACA GCA GGA AAA CAG AGC AGC CTG
       Tyr Leu Lys Gly His Thr Gly Thr Ala Gly Lys Gln Ser Ser Leu>
       ___b___b___b___ANG1 FIBRINOGEN-LIKE DOMAIN_b___b___b___b___>

460         470         480         490
               *           *           *           *
       ATC TTA CAC GGT GCT GAT TTC AGC ACT AAA GAT GCT GAT AAT GAC
       Ile Leu His Gly Ala Asp Phe Ser Thr Lys Asp Ala Asp Asn Asp>
       ___b___b___b___ANG1 FIBRINOGEN-LIKE DOMAIN_b___b___b___b___>

500         510         520         530         540
        *           *           *           *           *
       AAC TGT ATG TGC AAA TGT GCC CTC ATG TTA ACA GGA GGA TGG TGG
       Asn Cys Met Cys Lys Cys Ala Leu Met Leu Thr Gly Gly Trp Trp>
       ___b___b___b___ANG1 FIBRINOGEN-LIKE DOMAIN_b___b___b___b___>

550         560         570         580
               *           *           *           *
       TTT GAT GCT TGT GGC CCC TCC AAT CTA AAT GGA ATG TTC TAT ACT
       Phe Asp Ala Cys Gly Pro Ser Asn Leu Asn Gly Met Phe Tyr Thr>
       ___b___b___b___ANG1 FIBRINOGEN-LIKE DOMAIN_b___b___b___b___>

590         600         610         620         630
        *           *           *           *           *
       GCG GGA CAA AAC CAT GGA AAA CTG AAT GGG ATA AAG TGG CAC TAC
       Ala Gly Gln Asn His Gly Lys Leu Asn Gly Ile Lys Trp His Tyr>
       ___b___b___b___ANG1 FIBRINOGEN-LIKE DOMAIN_b___b___b___b___>

640         650         660         670
               *           *           *           *
       TTC AAA GGG CCA AGT TAC TCC TTA CGT TCC ACA ACT ATG ATG ATT
       Phe Lys Gly Pro Ser Tyr Ser Leu Arg Ser Thr Thr Met Met Ile>
       ___b___b___b___ANG1 FIBRINOGEN-LIKE DOMAIN_b___b___b___b___>

680         690         700         710         720
        *           *           *           *           *
       CGA CCT TTA GAT TTT GGC CCG GGC GAG CCC AAA TCT TGT GAC AAA
       Arg Pro Leu Asp Phe>
       ___ANG1 FIBRINO____>
                          Gly Pro Gly>
                          ___c___c___>
                                      Glu Pro Lys Ser Cys Asp Lys>
                                      ___d___d__FC TAG___d___d___>

730         740         750         760
               *           *           *           *
       ACT CAC ACA TGC CCA CCG TGC CCA GCA CCT GAA CTC CTG GGG GGA
       Thr His Thr Cys Pro Pro Cys Pro Ala Pro Glu Leu Leu Gly Gly>
       ___d___d___d___d___d___d__FC TAG___d___d___d___d___d___d___>

770         780         790         800         810
        *           *           *           *           *
       CCG TCA GTC TTC CTC TTC CCC CCA AAA CCC AAG GAC ACC CTC ATG
       Pro Ser Val Phe Leu Phe Pro Pro Lys Pro Lys Asp Thr Leu Met>
       ___d___d___d___d___d___d__FC TAG___d___d___d___d___d___d___>
```

Fig.3C.

```
         820           830           840           850
          *             *             *             *       *
ATC TCC CGG ACC CCT GAG GTC ACA TGC GTG GTG GTG GAC GTG AGC
Ile Ser Arg Thr Pro Glu Val Thr Cys Val Val Val Asp Val Ser>
___d___d___d___d___d___d__FC TAG___d___d___d___d___d___d___>

860           870           880           890           900
          *             *             *             *             *
CAC GAA GAC CCT GAG GTC AAG TTC AAC TGG TAC GTG GAC GGC GTG
His Glu Asp Pro Glu Val Lys Phe Asn Trp Tyr Val Asp Gly Val>
___d___d___d___d___d___d__FC TAG___d___d___d___d___d___d___>

910           920           930           940
          *             *             *             *       *
GAG GTG CAT AAT GCC AAG ACA AAG CCG CGG GAG GAG CAG TAC AAC
Glu Val His Asn Ala Lys Thr Lys Pro Arg Glu Glu Gln Tyr Asn>
___d___d___d___d___d___d__FC TAG___d___d___d___d___d___d___>

950           960           970           980           990
          *             *             *             *             *
AGC ACG TAC CGT GTG GTC AGC GTC CTC ACC GTC CTG CAC CAG GAC
Ser Thr Tyr Arg Val Val Ser Val Leu Thr Val Leu His Gln Asp>
___d___d___d___d___d___d__FC TAG___d___d___d___d___d___d___>

1000          1010          1020          1030
          *             *             *             *       *
TGG CTG AAT GGC AAG GAG TAC AAG TGC AAG GTC TCC AAC AAA GCC
Trp Leu Asn Gly Lys Glu Tyr Lys Cys Lys Val Ser Asn Lys Ala>
___d___d___d___d___d___d__FC TAG___d___d___d___d___d___d___>

1040          1050          1060          1070          1080
          *             *             *             *             *
CTC CCA GCC CCC ATC GAG AAA ACC ATC TCC AAA GCC AAA GGG CAG
Leu Pro Ala Pro Ile Glu Lys Thr Ile Ser Lys Ala Lys Gly Gln>
___d___d___d___d___d___d__FC TAG___d___d___d___d___d___d___>

1090          1100          1110          1120
          *             *             *             *       *
CCC CGA GAA CCA CAG GTG TAC ACC CTG CCC CCA TCC CGG GAT GAG
Pro Arg Glu Pro Gln Val Tyr Thr Leu Pro Pro Ser Arg Asp Glu>
___d___d___d___d___d___d__FC TAG___d___d___d___d___d___d___>

1130          1140          1150          1160          1170
          *             *             *             *             *
CTG ACC AAG AAC CAG GTC AGC CTG ACC TGC CTG GTC AAA GGC TTC
Leu Thr Lys Asn Gln Val Ser Leu Thr Cys Leu Val Lys Gly Phe>
___d___d___d___d___d___d__FC TAG___d___d___d___d___d___d___>

1180          1190          1200          1210
          *             *             *             *       *
TAT CCC AGC GAC ATC GCC GTG GAG TGG GAG AGC AAT GGG CAG CCG
Tyr Pro Ser Asp Ile Ala Val Glu Trp Glu Ser Asn Gly Gln Pro>
___d___d___d___d___d___d__FC TAG___d___d___d___d___d___d___>

1220          1230          1240          1250          1260
          *             *             *             *             *
GAG AAC AAC TAC AAG ACC ACG CCT CCC GTG CTG GAC TCC GAC GGC
Glu Asn Asn Tyr Lys Thr Thr Pro Pro Val Leu Asp Ser Asp Gly>
___d___d___d___d___d___d__FC TAG___d___d___d___d___d___d___>
```

Fig.3D.

```
         1270         1280         1290         1300
           *    *       *    *       *    *       *    *
TCC TTC TTC CTC TAC AGC AAG CTC ACC GTG GAC AAG AGC AGG TGG
Ser Phe Phe Leu Tyr Ser Lys Leu Thr Val Asp Lys Ser Arg Trp>
___d___d___d___d___d___d__FC TAG___d___d___d___d___d___d___>

1310         1320         1330         1340         1350
      *    *       *    *       *    *       *    *       *
CAG CAG GGG AAC GTC TTC TCA TGC TCC GTG ATG CAT GAG GCT CTG
Gln Gln Gly Asn Val Phe Ser Cys Ser Val Met His Glu Ala Leu>
___d___d___d___d___d___d__FC TAG___d___d___d___d___d___d___>

1360         1370         1380         1390
           *    *       *    *       *    *       *    *
CAC AAC CAC TAC ACG CAG AAG AGC CTC TCC CTG TCT CCG GGT AAA
His Asn His Tyr Thr Gln Lys Ser Leu Ser Leu Ser Pro Gly Lys>
___d___d___d___d___d___d__FC TAG___d___d___d___d___d___d___>

1400         1410         1420         1430         1440
      *    *       *    *       *    *       *    *       *
GGC GGT GGC GGT TCT GGC GCG CCT TTT AGA GAC TGT GCA GAT GTA
Gly Gly Gly Gly Ser Gly Ala Pro>
___G4S LINKER/ASC BRIDGE (N____>
                             Phe Arg Asp Cys Ala Asp Val>
                             ___ANG1 FIBRINOGEN-LIKE____>

1450         1460         1470         1480
           *    *       *    *       *    *       *    *
TAT CAA GCT GGT TTT AAT AAA AGT GGA ATC TAC ACT ATT TAT ATT
Tyr Gln Ala Gly Phe Asn Lys Ser Gly Ile Tyr Thr Ile Tyr Ile>
___f___f___f___ANG1 FIBRINOGEN-LIKE DOMAIN_f___f___f___f___>

1490         1500         1510         1520         1530
      *    *       *    . *       *    *       *    *       *
AAT AAT ATG CCA GAA CCC AAA AAG GTG TTT TGC AAT ATG GAT GTC
Asn Asn Met Pro Glu Pro Lys Lys Val Phe Cys Asn Met Asp Val>
___f___f___f___ANG1 FIBRINOGEN-LIKE DOMAIN_f___f___f___f___>

1540         1550         1560         1570
           *    *       *    *       *    *       *    *
AAT GGG GGA GGT TGG ACT GTA ATA CAA CAT CGT GAA GAT GGA AGT
Asn Gly Gly Gly Trp Thr Val Ile Gln His Arg Glu Asp Gly Ser>
___f___f___f___ANG1 FIBRINOGEN-LIKE DOMAIN_f___f___f___f___>

1580         1590         1600         1610         1620
      *    *       *    *       *    *       *·   *       *
CTA GAT TTC CAA AGA GGC TGG AAG GAA TAT AAA ATG GGT TTT GGA
Leu Asp Phe Gln Arg Gly Trp Lys Glu Tyr Lys Met Gly Phe Gly>
___f___f___f___ANG1 FIBRINOGEN-LIKE DOMAIN_f___f___f___f___>

1630         1640         1650         1660
           *    *       *    *       *    *       *    *
AAT CCC TCC GGT GAA TAT TGG CTG GGG AAT GAG TTT ATT TTT GCC
Asn Pro Ser Gly Glu Tyr Trp Leu Gly Asn Glu Phe Ile Phe Ala>
___f___f___f___ANG1 FIBRINOGEN-LIKE DOMAIN_f___f___f___f___>
```

Fig.3E.

```
        1670           1680           1690           1700           1710
          *      *      *      *      *      *      *      *      *
ATT ACC AGT CAG AGG CAG TAC ATG CTA AGA ATT GAG TTA ATG GAC
Ile Thr Ser Gln Arg Gln Tyr Met Leu Arg Ile Glu Leu Met Asp>
___f___f___f___ANG1 FIBRINOGEN-LIKE DOMAIN_f___f___f___f___>

1720           1730           1740           1750
          *      *      *      *      *      *      *      *      *
TGG GAA GGG AAC CGA GCC TAT TCA CAG TAT GAC AGA TTC CAC ATA
Trp Glu Gly Asn Arg Ala Tyr Ser Gln Tyr Asp Arg Phe His Ile>
___f___f___f___ANG1 FIBRINOGEN-LIKE DOMAIN_f___f___f___f___>

1760           1770           1780           1790           1800
          *      *      *      *      *      *      *      *      *
GGA AAT GAA AAG CAA AAC TAT AGG TTG TAT TTA AAA GGT CAC ACT
Gly Asn Glu Lys Gln Asn Tyr Arg Leu Tyr Leu Lys Gly His Thr>
___f___f___f___ANG1 FIBRINOGEN-LIKE DOMAIN_f___f___f___f___>

1810           1820           1830           1840
          *      *      *      *      *      *      *      *      *
GGG ACA GCA GGA AAA CAG AGC AGC CTG ATC TTA CAC GGT GCT GAT
Gly Thr Ala Gly Lys Gln Ser Ser Leu Ile Leu His Gly Ala Asp>
___f___f___f___ANG1 FIBRINOGEN-LIKE DOMAIN_f___f___f___f___>

1850           1860           1870           1880           1890
          *      *      *      *      *      *      *      *      *
TTC AGC ACT AAA GAT GCT GAT AAT GAC AAC TGT ATG TGC AAA TGT
Phe Ser Thr Lys Asp Ala Asp Asn Asp Asn Cys Met Cys Lys Cys>
___f___f___f___ANG1 FIBRINOGEN-LIKE DOMAIN_f___f___f___f___>

1900           1910           1920           1930
          *      *      *      *      *      *      *      *      *
GCC CTC ATG TTA ACA GGA GGA TGG TGG TTT GAT GCT TGT GGC CCC
Ala Leu Met Leu Thr Gly Gly Trp Trp Phe Asp Ala Cys Gly Pro>
___f___f___f___ANG1 FIBRINOGEN-LIKE DOMAIN_f___f___f___f___>

1940           1950           1960           1970           1980
          *      *      *      *      *      *      *      *      *
TCC AAT CTA AAT GGA ATG TTC TAT ACT GCG GGA CAA AAC CAT GGA
Ser Asn Leu Asn Gly Met Phe Tyr Thr Ala Gly Gln Asn His Gly>
___f___f___f___ANG1 FIBRINOGEN-LIKE DOMAIN_f___f___f___f___>

1990           2000           2010           2020
          *      *      *      *      *      *      *      *      *
AAA CTG AAT GGG ATA AAG TGG CAC TAC TTC AAA GGG CCA AGT TAC
Lys Leu Asn Gly Ile Lys Trp His Tyr Phe Lys Gly Pro Ser Tyr>
___f___f___f___ANG1 FIBRINOGEN-LIKE DOMAIN_f___f___f___f___>

2030           2040           2050           2060
          *      *      *      *      *      *      *      *
TCC TTA CGT TCC ACA ACT ATG ATG ATT CGA CCT TTA GAT TTT
Ser Leu Arg Ser Thr Thr Met Met Ile Arg Pro Leu Asp Phe>
___f___f___f_ANG1 FIBRINOGEN-LIKE DOMAIN___f___f___f___>
```

Fig.4A.

```
          10             20             30             40
     *    *    *    *    *    *    *    *    *
ATG  TCT  GCA  CTT  CTG  ATC  CTA  GCT  CTT  GTT  GGA  GCT  GCA  GTT  GCT
Met  Ser  Ala  Leu  Leu  Ile  Leu  Ala  Leu  Val  Gly  Ala  Ala  Val  Ala>
___a___a___a___a_TRYPSIN SIGNAL SEQUENCE___a___a___a___a___>

50             60             70             80             90
     *    *    *    *    *    *    *    *    *
AGA  GAC  TGT  GCT  GAA  GTA  TTC  AAA  TCA  GGA  CAC  ACC  ACA  AAT  GGC
Arg  Asp  Cys  Ala  Glu  Val  Phe  Lys  Ser  Gly  His  Thr  Thr  Asn  Gly>
___b___b___b___ANG2 FIBRINOGEN-LIKE DOMAIN_b___b___b___b___>

100            110            120            130
     *    *    *    *    *    *    *    *    *
ATC  TAC  ACG  TTA  ACA  TTC  CCT  AAT  TCT  ACA  GAA  GAG  ATC  AAG  GCC
Ile  Tyr  Thr  Leu  Thr  Phe  Pro  Asn  Ser  Thr  Glu  Glu  Ile  Lys  Ala>
___b___b___b___ANG2 FIBRINOGEN-LIKE DOMAIN_b___b___b___b___>

140            150            160            170            180
     *    *    *    *    *    *    *    *    *
TAC  TGT  GAC  ATG  GAA  GCT  GGA  GGA  GGC  GGG  TGG  ACA  ATT  ATT  CAG
Tyr  Cys  Asp  Met  Glu  Ala  Gly  Gly  Gly  Gly  Trp  Thr  Ile  Ile  Gln>
___b___b___b___ANG2 FIBRINOGEN-LIKE DOMAIN_b___b___b___b___>

190            200            210            220
     *    *    *    *    *    *    *    *    *
CGA  CGT  GAG  GAT  GGC  AGC  GTT  GAT  TTT  CAG  AGG  ACT  TGG  AAA  GAA
Arg  Arg  Glu  Asp  Gly  Ser  Val  Asp  Phe  Gln  Arg  Thr  Trp  Lys  Glu>
___b___b___b___ANG2 FIBRINOGEN-LIKE DOMAIN_b___b___b___b___>

230            240            250            260            270
     *    *    *    *    *    *    *    *    *
TAT  AAA  GTG  GGA  TTT  GGT  AAC  CCT  TCA  GGA  GAA  TAT  TGG  CTG  GGA
Tyr  Lys  Val  Gly  Phe  Gly  Asn  Pro  Ser  Gly  Glu  Tyr  Trp  Leu  Gly>
___b___b___b___ANG2 FIBRINOGEN-LIKE DOMAIN_b___b___b___b___>

280            290            300            310
     *    *    *    *    *    *    *    *    *
AAT  GAG  TTT  GTT  TCG  CAA  CTG  ACT  AAT  CAG  CAA  CGC  TAT  GTG  CTT
Asn  Glu  Phe  Val  Ser  Gln  Leu  Thr  Asn  Gln  Gln  Arg  Tyr  Val  Leu>
___b___b___b___ANG2 FIBRINOGEN-LIKE DOMAIN_b___b___b___b___>

320            330            340            350            360
     *    *    *    *    *    *    *    *    *
AAA  ATA  CAC  CTT  AAA  GAC  TGG  GAA  GGG  AAT  GAG  GCT  TAC  TCA  TTG
Lys  Ile  His  Leu  Lys  Asp  Trp  Glu  Gly  Asn  Glu  Ala  Tyr  Ser  Leu>
___b___b___b___ANG2 FIBRINOGEN-LIKE DOMAIN_b___b___b___b___>

370            380            390            400
     *    *    *    *    *    *    *    *    *
TAT  GAA  CAT  TTC  TAT  CTC  TCA  AGT  GAA  GAA  CTC  AAT  TAT  AGG  ATT
Tyr  Glu  His  Phe  Tyr  Leu  Ser  Ser  Glu  Glu  Leu  Asn  Tyr  Arg  Ile>
___b___b___b___ANG2 FIBRINOGEN-LIKE DOMAIN_b___b___b___b___>
```

Fig.4B.

```
              410          420          430          440          450
               *      *     *      *     *      *     *      *     *
              CAC CTT AAA GGA CTT ACA GGG ACA GCC GGC AAA ATA AGC AGC ATC
              His Leu Lys Gly Leu Thr Gly Thr Ala Gly Lys Ile Ser Ser Ile>
              ___b___b___b___ANG2 FIBRINOGEN-LIKE DOMAIN_b___b___b___b___>

460          470          480          490
                *     *      *     *      *     *      *     *      *
              AGC CAA CCA GGA AAT GAT TTT AGC ACA AAG GAT GGA GAC AAC GAC
              Ser Gln Pro Gly Asn Asp Phe Ser Thr Lys Asp Gly Asp Asn Asp>
              ___b___b___b___ANG2 FIBRINOGEN-LIKE DOMAIN_b___b___b___b___>

500          510          520          530          540
               *      *     *      *     *      *     *      *     *
              AAA TGT ATT TGC AAA TGT TCA CAA ATG CTA ACA GGA GGC TGG TGG
              Lys Cys Ile Cys Lys Cys Ser Gln Met Leu Thr Gly Gly Trp Trp>
              ___b___b___b___ANG2 FIBRINOGEN-LIKE DOMAIN_b___b___b___b___>

550          560          570          580
                *     *      *     *      *     *      *     *      *
              TTT GAT GCA TGT GGT CCT TCC AAC TTG AAC GGA ATG TAC TAT CCA
              Phe Asp Ala Cys Gly Pro Ser Asn Leu Asn Gly Met Tyr Tyr Pro>
              ___b___b___b___ANG2 FIBRINOGEN-LIKE DOMAIN_b___b___b___b___>

590          600          610          620          630
               *      *     *      *     *      *     *      *     *
              CAG AGG CAG AAC ACA AAT AAG TTC AAC GGC ATT AAA TGG TAC TAC
              Gln Arg Gln Asn Thr Asn Lys Phe Asn Gly Ile Lys Trp Tyr Tyr>
              ___b___b___b___ANG2 FIBRINOGEN-LIKE DOMAIN_b___b___b___b___>

640          650          660          670
                *     *      *     *      *     *      *     *      *
              TGG AAA GGC TCA GGC TAT TCG CTC AAG GCC ACA ACC ATG ATG ATC
              Trp Lys Gly Ser Gly Tyr Ser Leu Lys Ala Thr Thr Met Met Ile>
              ___b___b___b___ANG2 FIBRINOGEN-LIKE DOMAIN_b___b___b___b___>

680          690          700          710          720
               *      *     *      *     *      *     *      *     *
              CGA CCA GCA GAT TTC GGG GGC CCG GGC GAG CCC AAA TCT TGT GAC
              Arg Pro Ala Asp Phe>
              ___ANG2 FIBRINO____>
                              Gly Gly Pro Gly>
                              ___GGPG BRI____>
                                            Glu Pro Lys Ser Cys Asp>
                                            ___d____FC TAG_d___d___>

730          740          750          760
                *     *      *     *      *     *      *     *      *
              AAA ACT CAC ACA TGC CCA CCG TGC CCA GCA CCT GAA CTC CTG GGG
              Lys Thr His Thr Cys Pro Pro Cys Pro Ala Pro Glu Leu Leu Gly>
              ___d___d___d___d___d___d_FC TAG___d___d___d___d___d___d___>

770          780          790          800          810
               *      *     *      *     *      *     *      *     *
              GGA CCG TCA GTC TTC CTC TTC CCC CCA AAA CCC AAG GAC ACC CTC
              Gly Pro Ser Val Phe Leu Phe Pro Pro Lys Pro Lys Asp Thr Leu>
              ___d___d___d___d___d___d_FC TAG___d___d___d___d___d___d___>
```

Fig.4C.

```
              820           830           840           850
               *             *             *             *
ATG ATC TCC CGG ACC CCT GAG GTC ACA TGC GTG GTG GTG GAC GTG
Met Ile Ser Arg Thr Pro Glu Val Thr Cys Val Val Val Asp Val>
___d___d___d___d___d___d_FC TAG___d___d___d___d___d___d___>

860           870           880           890           900
               *             *             *             *             *
AGC CAC GAA GAC CCT GAG GTC AAG TTC AAC TGG TAC GTG GAC GGC
Ser His Glu Asp Pro Glu Val Lys Phe Asn Trp Tyr Val Asp Gly>
___d___d___d___d___d___d_FC TAG___d___d___d___d___d___d___>

910           920           930           940
               *             *             *             *
GTG GAG GTG CAT AAT GCC AAG ACA AAG CCG CGG GAG GAG CAG TAC
Val Glu Val His Asn Ala Lys Thr Lys Pro Arg Glu Glu Gln Tyr>
___d___d___d___d___d___d_FC TAG___d___d___d___d___d___d___>

950           960           970           980           990
               *             *             *             *             *
AAC AGC ACG TAC CGT GTG GTC AGC GTC CTC ACC GTC CTG CAC CAG
Asn Ser Thr Tyr Arg Val Val Ser Val Leu Thr Val Leu His Gln>
___d___d___d___d___d___d_FC TAG___d___d___d___d___d___d___>

1000          1010          1020          1030
               *             *             *             *
GAC TGG CTG AAT GGC AAG GAG TAC AAG TGC AAG GTC TCC AAC AAA
Asp Trp Leu Asn Gly Lys Glu Tyr Lys Cys Lys Val Ser Asn Lys>
___d___d___d___d___d___d_FC TAG___d___d___d___d___d___d___>

1040          1050          1060          1070          1080
               *             *             *             *             *
GCC CTC CCA GCC CCC ATC GAG AAA ACC ATC TCC AAA GCC AAA GGG
Ala Leu Pro Ala Pro Ile Glu Lys Thr Ile Ser Lys Ala Lys Gly>
___d___d___d___d___d___d_FC TAG___d___d___d___d___d___d___>

1090          1100          1110          1120
               *             *             *             *
CAG CCC CGA GAA CCA CAG GTG TAC ACC CTG CCC CCA TCC CGG GAT
Gln Pro Arg Glu Pro Gln Val Tyr Thr Leu Pro Pro Ser Arg Asp>
___d___d___d___d___d___d_FC TAG___d___d___d___d___d___d___>

1130          1140          1150          1160          1170
               *             *             *             *             *
GAG CTG ACC AAG AAC CAG GTC AGC CTG ACC TGC CTG GTC AAA GGC
Glu Leu Thr Lys Asn Gln Val Ser Leu Thr Cys Leu Val Lys Gly>
___d___d___d___d___d___d_FC TAG___d___d___d___d___d___d___>

1180          1190          1200          1210
               *             *             *             *
TTC TAT CCC AGC GAC ATC GCC GTG GAG TGG GAG AGC AAT GGG CAG
Phe Tyr Pro Ser Asp Ile Ala Val Glu Trp Glu Ser Asn Gly Gln>
___d___d___d___d___d___d_FC TAG___d___d___d___d___d___d___>

1220          1230          1240          1250          1260
               *             *             *             *             *
CCG GAG AAC AAC TAC AAG ACC ACG CCT CCC GTG CTG GAC TCC GAC
Pro Glu Asn Asn Tyr Lys Thr Thr Pro Pro Val Leu Asp Ser Asp>
___d___d___d___d___d___d_FC TAG___d___d___d___d___d___d___>
```

Fig.4D.

```
         1270        1280        1290        1300
           *    *      *    *      *    *      *    *
GGC TCC TTC TTC CTC TAC AGC AAG CTC ACC GTG GAC AAG AGC AGG
Gly Ser Phe Phe Leu Tyr Ser Lys Leu Thr Val Asp Lys Ser Arg>
___d___d___d___d___d___d__FC TAG___d___d___d___d___d___d___>

1310        1320        1330        1340        1350
    *    *      *    *      *    *      *    *      *
TGG CAG CAG GGG AAC GTC TTC TCA TGC TCC GTG ATG CAT GAG GCT
Trp Gln Gln Gly Asn Val Phe Ser Cys Ser Val Met His Glu Ala>
___d___d___d___d___d___d__FC TAG___d___d___d___d___d___d___>

1360        1370        1380        1390
    *    *      *    *      *    *      *    *
CTG CAC AAC CAC TAC ACG CAG AAG AGC CTC TCC CTG TCT CCG GGT
Leu His Asn His Tyr Thr Gln Lys Ser Leu Ser Leu Ser Pro Gly>
___d___d___d___d___d___d__FC TAG___d___d___d___d___d___d___>

1400        1410        1420        1430        1440
    *    *      *    *      *    *      *    *      *
AAA GGC GGT GGC GGT TCT GGC GCG CCT AGA GAC TGT GCT GAA GTA
Lys>
___>
        Gly Gly Gly Gly Ser Gly Ala Pro>
        ___e___GGGGSGAP BRIDGE_e___e___>
                            Arg Asp Cys Ala Glu Val>
                            ___ANG2 FIBRINOGEN-____>

1450        1460        1470        1480
           *    *      *    *      *    *      *    *
TTC AAA TCA GGA CAC ACC ACA AAT GGC ATC TAC ACG TTA ACA TTC
Phe Lys Ser Gly His Thr Thr Asn Gly Ile Tyr Thr Leu Thr Phe>
___f___f___f___ANG2 FIBRINOGEN-LIKE DOMAIN_f___f___f___f___>

1490        1500        1510        1520        1530
    *    *      *    *      *    *      *    *      *
CCT AAT TCT ACA GAA GAG ATC AAG GCC TAC TGT GAC ATG GAA GCT
Pro Asn Ser Thr Glu Glu Ile Lys Ala Tyr Cys Asp Met Glu Ala>
___f___f___f___ANG2 FIBRINOGEN-LIKE DOMAIN_f___f___f___f___>

1540        1550        1560        1570
    *    *      *    *      *    *      *    *
GGA GGA GGC GGG TGG ACA ATT ATT CAG CGA CGT GAG GAT GGC AGC
Gly Gly Gly Gly Trp Thr Ile Ile Gln Arg Arg Glu Asp Gly Ser>
___f___f___f___ANG2 FIBRINOGEN-LIKE DOMAIN_f___f___f___f___>

1580        1590        1600        1610        1620
    *    *      *    *      *    *      *    *      *
GTT GAT TTT CAG AGG ACT TGG AAA GAA TAT AAA GTG GGA TTT GGT
Val Asp Phe Gln Arg Thr Trp Lys Glu Tyr Lys Val Gly Phe Gly>
___f___f___f___ANG2 FIBRINOGEN-LIKE DOMAIN_f___f___f___f___>

1630        1640        1650        1660
    *    *      *    *      *    *      *    *
AAC CCT TCA GGA GAA TAT TGG CTG GGA AAT GAG TTT GTT TCG CAA
Asn Pro Ser Gly Glu Tyr Trp Leu Gly Asn Glu Phe Val Ser Gln>
___f___f___f___ANG2 FIBRINOGEN-LIKE DOMAIN_f___f___f___f___>
```

Fig.4E.

```
        1670         1680         1690         1700         1710
          *       *    *       *    *       *    *       *    *
      CTG ACT AAT CAG CAA CGC TAT GTG CTT AAA ATA CAC CTT AAA GAC
      Leu Thr Asn Gln Gln Arg Tyr Val Leu Lys Ile His Leu Lys Asp>
      ___f___f___f___ANG2 FIBRINOGEN-LIKE DOMAIN_f___f___f___f___>

1720         1730        1740         1750
                *       *    *       *    *       *    *       *    *
      TGG GAA GGG AAT GAG GCT TAC TCA TTG TAT GAA CAT TTC TAT CTC
      Trp Glu Gly Asn Glu Ala Tyr Ser Leu Tyr Glu His Phe Tyr Leu>
      ___f___f___f___ANG2 FIBRINOGEN-LIKE DOMAIN_f___f___f___f___>

1760         1770        1780         1790         1800
          *       *    *       *    *       *    *       *    *
      TCA AGT GAA GAA CTC AAT TAT AGG ATT CAC CTT AAA GGA CTT ACA
      Ser Ser Glu Glu Leu Asn Tyr Arg Ile His Leu Lys Gly Leu Thr>
      ___f___f___f___ANG2 FIBRINOGEN-LIKE DOMAIN_f___f___f___f___>

1810         1820        1830         1840
                *       *    *       *    *       *    *       *    *
      GGG ACA GCC GGC AAA ATA AGC AGC ATC AGC CAA CCA GGA AAT GAT
      Gly Thr Ala Gly Lys Ile Ser Ser Ile Ser Gln Pro Gly Asn Asp>
      ___f___f___f___ANG2 FIBRINOGEN-LIKE DOMAIN_f___f___f___f___>

1850         1860        1870         1880         1890
          *       *    *       *    *       *    *       *    *
      TTT AGC ACA AAG GAT GGA GAC AAC GAC AAA TGT ATT TGC AAA TGT
      Phe Ser Thr Lys Asp Gly Asp Asn Asp Lys Cys Ile Cys Lys Cys>
      ___f___f___f___ANG2 FIBRINOGEN-LIKE DOMAIN_f___f___f___f___>

1900         1910        1920         1930
                *       *    *       *    *       *    *       *    *
      TCA CAA ATG CTA ACA GGA GGC TGG TGG TTT GAT GCA TGT GGT CCT
      Ser Gln Met Leu Thr Gly Gly Trp Trp Phe Asp Ala Cys Gly Pro>
      ___f___f___f___ANG2 FIBRINOGEN-LIKE DOMAIN_f___f___f___f___>

1940         1950        1960         1970         1980
          *       *    *       *    *       *    *       *    *
      TCC AAC TTG AAC GGA ATG TAC TAT CCA CAG AGG CAG AAC ACA AAT
      Ser Asn Leu Asn Gly Met Tyr Tyr Pro Gln Arg Gln Asn Thr Asn>
      ___f___f___f___ANG2 FIBRINOGEN-LIKE DOMAIN_f___f___f___f___>

1990         2000        2010         2020
                *       *    *       *    *       *    *       *    *
      AAG TTC AAC GGC ATT AAA TGG TAC TAC TGG AAA GGC TCA GGC TAT
      Lys Phe Asn Gly Ile Lys Trp Tyr Tyr Trp Lys Gly Ser Gly Tyr>
      ___f___f___f___ANG2 FIBRINOGEN-LIKE DOMAIN_f___f___f___f___>

2030         2040        2050         2060         2070
          *       *    *       *    *       *    *       *    *
      TCG CTC AAG GCC ACA ACC ATG ATG ATC CGA CCA GCA GAT TTC TGA
      Ser Leu Lys Ala Thr Thr Met Met Ile Arg Pro Ala Asp Phe>
      ___f___f___f_ANG2 FIBRINOGEN-LIKE DOMAIN___f___f___f___>
```

Ang1-FD-Fc-FD

Ang2-FD-Fc-FD

Fig.14A.

```
             10           20           30           40
              *            *            *            *       *
ATG GCT CGG CCT GGG CAG CGT TGG CTC GGC AAG TGG CTT GTG GCG
Met Ala Arg Pro Gly Gln Arg Trp Leu Gly Lys Trp Leu Val Ala>
___a___a_ELK-L ECTODOMAIN 1 (WITH SIGNAL PEPTIDE)__a___a___>

50           60           70           80           90
      *            *    *       *            *            *
ATG GTC GTG TGG GCG CTG TGC CGG CTC GCC ACA CCG CTG GCC AAG
Met Val Val Trp Ala Leu Cys Arg Leu Ala Thr Pro Leu Ala Lys>
___a___a_ELK-L ECTODOMAIN 1 (WITH SIGNAL PEPTIDE)__a___a___>

100          110          120          130
         *            *            *            *        *
AAC CTG GAG CCC GTA TCC TGG AGC TCC CTC AAC CCC AAG TTC CTG
Asn Leu Glu Pro Val Ser Trp Ser Ser Leu Asn Pro Lys Phe Leu>
___a___a_ELK-L ECTODOMAIN 1 (WITH SIGNAL PEPTIDE)__a___a___>

140          150          160          170          180
      *            *            *            *            *
AGT GGG AAG GGC TTG GTG ATC TAT CCG AAA ATT GGA GAC AAG CTG
Ser Gly Lys Gly Leu Val Ile Tyr Pro Lys Ile Gly Asp Lys Leu>
___a___a_ELK-L ECTODOMAIN 1 (WITH SIGNAL PEPTIDE)__a___a___>

190          200          210          220
         *            *    *       *            *        *
GAC ATC ATC TGC CCC CGA GCA GAA GCA GGG CGG CCC TAT GAG TAC
Asp Ile Ile Cys Pro Arg Ala Glu Ala Gly Arg Pro Tyr Glu Tyr>
___a___a_ELK-L ECTODOMAIN 1 (WITH SIGNAL PEPTIDE)__a___a___>

230          240          250          260          270
      *            *            *            *            *
TAC AAG CTG TAC CTG GTG CGG CCT GAG CAG GCA GCT GCC TGT AGC
Tyr Lys Leu Tyr Leu Val Arg Pro Glu Gln Ala Ala Ala Cys Ser>
___a___a_ELK-L ECTODOMAIN 1 (WITH SIGNAL PEPTIDE)__a___a___>

280          290          300          310
         *            *    *       *            *        *
ACA GTT CTC GAC CCC AAC GTG TTG GTC ACC TGC AAT AGG CCA GAG
Thr Val Leu Asp Pro Asn Val Leu Val Thr Cys Asn Arg Pro Glu>
___a___a_ELK-L ECTODOMAIN 1 (WITH SIGNAL PEPTIDE)__a___a___>

320          330          340          350          360
      *            *            *            *            *
CAG GAA ATA CGC TTT ACC ATC AAG TTC CAG GAG TTC AGC CCC AAC
Gln Glu Ile Arg Phe Thr Ile Lys Phe Gln Glu Phe Ser Pro Asn>
___a___a_ELK-L ECTODOMAIN 1 (WITH SIGNAL PEPTIDE)__a___a___>

370          380          390          400
         *            *            *            *        *
TAC ATG GGC CTG GAG TTC AAG AAG CAC CAT GAT TAC TAC ATT ACC
Tyr Met Gly Leu Glu Phe Lys Lys His His Asp Tyr Tyr Ile Thr>
___a___a_ELK-L ECTODOMAIN 1 (WITH SIGNAL PEPTIDE)__a___a___>
```

Fig.14B.

```
           410         420         430         440         450
            *     *     *     *     *     *     *     *     *
          TCA ACA TCC AAT GGA AGC CTG GAG GGG CTG GAA AAC CGG GAG GGC
          Ser Thr Ser Asn Gly Ser Leu Glu Gly Leu Glu Asn Arg Glu Gly>
          ___a___a_ELK-L ECTODOMAIN 1 (WITH SIGNAL PEPTIDE)__a___a___>

460         470         480         490
            *     *     *     *     *     *     *     *     *
          GGT GTG TGC CGC ACA CGC ACC ATG AAG ATC ATC ATG AAG GTT GGG
          Gly Val Cys Arg Thr Arg Thr Met Lys Ile Ile Met Lys Val Gly>
          ___a___a_ELK-L ECTODOMAIN 1 (WITH SIGNAL PEPTIDE)__a___a___>

500         510         520         530         540
            *     *     *     *     *     *     *     *     *
          CAA GAT CCC AAT GCT GTG ACG CCT GAG CAG CTG ACT ACC AGC AGG
          Gln Asp Pro Asn Ala Val Thr Pro Glu Gln Leu Thr Thr Ser Arg>
          ___a___a_ELK-L ECTODOMAIN 1 (WITH SIGNAL PEPTIDE)__a___a___>

550         560         570         580
            *     *     *     *     *     *     *     *     *
          CCC AGC AAG GAG GCA GAC AAC ACT GTC AAG ATG GCC ACA CAG GCC
          Pro Ser Lys Glu Ala Asp Asn Thr Val Lys Met Ala Thr Gln Ala>
          ___a___a_ELK-L ECTODOMAIN 1 (WITH SIGNAL PEPTIDE)__a___a___>

590         600         610         620         630
            *     *     *     *     *     *     *     *     *
          CCT GGT AGT CGG GGC TCC CTG GGT GAC TCT GAT GGC AAG CAT GAG
          Pro Gly Ser Arg Gly Ser Leu Gly Asp Ser Asp Gly Lys His Glu>
          ___a___a_ELK-L ECTODOMAIN 1 (WITH SIGNAL PEPTIDE)__a___a___>

640         650         660         670
            *     *     *     *     *     *     *     *     *
          ACT GTG AAC CAG GAA GAG AAG AGT GGC CCA GGT GCA AGT GGG GGC
          Thr Val Asn Gln Glu Glu Lys Ser Gly Pro Gly Ala Ser Gly Gly>
          ___a___a_ELK-L ECTODOMAIN 1 (WITH SIGNAL PEPTIDE)__a___a___>

680         690         700         710         720
            *     *     *     *     *     *     *     *     *
          AGC AGC GGG GAC CCT GAT GGC TTC TTC AAC TCC AAG GGC CCG GGT
          Ser Ser Gly Asp Pro Asp Gly Phe Phe Asn Ser Lys>
          ___ELK-L ECTODOMAIN 1 (WITH SIGNAL PEPTIDE)____>
                                                    Gly Pro Gly>
                                                    ___b___b___>

730         740         750         760
            *     *     *     *     *     *     *     *     *
          AAG AAC CTG GAG CCC GTA TCC TGG AGC TCC CTC AAC CCC AAG TTC
          Lys Asn Leu Glu Pro Val Ser Trp Ser Ser Leu Asn Pro Lys Phe>
          ___c___c___c__ELK-L ECTODOMAIN 2 (NO SIGNAL)___c___c___c___>

770         780         790         800         810
            *     *     *     *     *     *     *     *     *
          CTG AGT GGG AAG GGC TTG GTG ATC TAT CCG AAA ATT GGA GAC AAG
          Leu Ser Gly Lys Gly Leu Val Ile Tyr Pro Lys Ile Gly Asp Lys>
          ___c___c___c__ELK-L ECTODOMAIN 2 (NO SIGNAL)___c___c___c___>
```

Fig.14C.

```
              820         830         840         850
               *           *           *           *
        CTG GAC ATC ATC TGC CCC CGA GCA GAA GCA GGG CGG CCC TAT GAG
        Leu Asp Ile Ile Cys Pro Arg Ala Glu Ala Gly Arg Pro Tyr Glu>
        ___c___c___c__ELK-L ECTODOMAIN 2 (NO SIGNAL)___c___c___c___>

860         870         880         890         900
               *           *           *           *           *
        TAC TAC AAG CTG TAC CTG GTG CGG CCT GAG CAG GCA GCT GCC TGT
        Tyr Tyr Lys Leu Tyr Leu Val Arg Pro Glu Gln Ala Ala Ala Cys>
        ___c___c___c__ELK-L ECTODOMAIN 2 (NO SIGNAL)___c___c___c___>

910         920         930         940
               *           *           *           *
        AGC ACA GTT CTC GAC CCC AAC GTG TTG GTC ACC TGC AAT AGG CCA
        Ser Thr Val Leu Asp Pro Asn Val Leu Val Thr Cys Asn Arg Pro>
        ___c___c___c__ELK-L ECTODOMAIN 2 (NO SIGNAL)___c___c___c___>

950         960         970         980         990
               *           *           *           *           *
        GAG CAG GAA ATA CGC TTT ACC ATC AAG TTC CAG GAG TTC AGC CCC
        Glu Gln Glu Ile Arg Phe Thr Ile Lys Phe Gln Glu Phe Ser Pro>
        ___c___c___c__ELK-L ECTODOMAIN 2 (NO SIGNAL)___c___c___c___>

1000        1010        1020        1030
               *           *           *           *
        AAC TAC ATG GGC CTG GAG TTC AAG AAG CAC CAT GAT TAC TAC ATT
        Asn Tyr Met Gly Leu Glu Phe Lys Lys His His Asp Tyr Tyr Ile>
        ___c___c___c__ELK-L ECTODOMAIN 2 (NO SIGNAL)___c___c___c___>

1040        1050        1060        1070        1080
               *           *           *           *           *
        ACC TCA ACA TCC AAT GGA AGC CTG GAG GGG CTG GAA AAC CGG GAG
        Thr Ser Thr Ser Asn Gly Ser Leu Glu Gly Leu Glu Asn Arg Glu>
        ___c___c___c__ELK-L ECTODOMAIN 2 (NO SIGNAL)___c___c___c___>

1090        1100        1110        1120
               *           *           *           *
        GGC GGT GTG TGC CGC ACA CGC ACC ATG AAG ATC ATC ATG AAG GTT
        Gly Gly Val Cys Arg Thr Arg Thr Met Lys Ile Ile Met Lys Val>
        ___c___c___c__ELK-L ECTODOMAIN 2 (NO SIGNAL)___c___c___c___>

1130        1140        1150        1160        1170
               *           *           *           *           *
        GGG CAA GAT CCC AAT GCT GTG ACG CCT GAG CAG CTG ACT ACC AGC
        Gly Gln Asp Pro Asn Ala Val Thr Pro Glu Gln Leu Thr Thr Ser>
        ___c___c___c__ELK-L ECTODOMAIN 2 (NO SIGNAL)___c___c___c___>

1180        1190        1200        1210
               *           *           *           *
        AGG CCC AGC AAG GAG GCA GAC AAC ACT GTC AAG ATG GCC ACA CAG
        Arg Pro Ser Lys Glu Ala Asp Asn Thr Val Lys Met Ala Thr Gln>
        ___c___c___c__ELK-L ECTODOMAIN 2 (NO SIGNAL)___c___c___c___>

1220        1230        1240        1250        1260
               *           *           *           *           *
        GCC CCT GGT AGT CGG GGC TCC CTG GGT GAC TCT GAT GGC AAG CAT
        Ala Pro Gly Ser Arg Gly Ser Leu Gly Asp Ser Asp Gly Lys His>
        ___c___c___c__ELK-L ECTODOMAIN 2 (NO SIGNAL)___c___c___c___>
```

Fig.14D.

```
           1270      1280      1290      1300
            *    *    *    *    *    *    *    *    *
          GAG ACT GTG AAC CAG GAA GAG AAG AGT GGC CCA GGT GCA AGT GGG
          Glu Thr Val Asn Gln Glu Glu Lys Ser Gly Pro Gly Ala Ser Gly>
          ___c___c___c__ELK-L ECTODOMAIN 2 (NO SIGNAL)___c___c___c___>

1310      1320      1330      1340      1350
            *    *    *    *    *    *    *    *    *    *
          GGC AGC AGC GGG GAC CCT GAT GGC TTC TTC AAC TCC AAA GGC CCG
          Gly Ser Ser Gly Asp Pro Asp Gly Phe Phe Asn Ser Lys>
          ___c___c__ELK-L ECTODOMAIN 2 (NO SIGNAL)___c___c___>
                                                          Gly Pro>
                                                          ___d___>

1360      1370      1380      1390
            *    *    *    *    *    *    *    *    *
          GGC GAG CCC AAA TCT TGT GAC AAA ACT CAC ACA TGC CCA CCG TGC
          Gly>
          ___>
               Glu Pro Lys Ser Cys Asp Lys Thr His Thr Cys Pro Pro Cys>
               ___e___e___e___e__HUMAN IGG1 FC TAG____e___e___e___e___>

1400      1410      1420      1430      1440
            *    *    *    *    *    *    *    *    *    *
          CCA GCA CCT GAA CTC CTG GGG GGA CCG TCA GTC TTC CTC TTC CCC
          Pro Ala Pro Glu Leu Leu Gly Gly Pro Ser Val Phe Leu Phe Pro>
          ___e___e___e___e____HUMAN IGG1 FC TAG__e___e___e___e___e___>

1450      1460      1470      1480
            *    *    *    *    *    *    *    *    *
          CCA AAA CCC AAG GAC ACC CTC ATG ATC TCC CGG ACC CCT GAG GTC
          Pro Lys Pro Lys Asp Thr Leu Met Ile Ser Arg Thr Pro Glu Val>
          ___e___e___e___e____HUMAN IGG1 FC TAG__e___e___e___e___e___>

1490      1500      1510      1520      1530
            *    *    *    *    *    *    *    *    *    *
          ACA TGC GTG GTG GTG GAC GTG AGC CAC GAA GAC CCT GAG GTC AAG
          Thr Cys Val Val Val Asp Val Ser His Glu Asp Pro Glu Val Lys>
          ___e___e___e___e____HUMAN IGG1 FC TAG__e___e___e___e___e___>

1540      1550      1560      1570
            *    *    *    *    *    *    *    *    *
          TTC AAC TGG TAC GTG GAC GGC GTG GAG GTG CAT AAT GCC AAG ACA
          Phe Asn Trp Tyr Val Asp Gly Val Glu Val His Asn Ala Lys Thr>
          ___e___e___e___e____HUMAN IGG1 FC TAG__e___e___e___e___e___>

1580      1590      1600      1610      1620
            *    *    *    *    *    *    *    *    *    *
          AAG CCG CGG GAG GAG CAG TAC AAC AGC ACG TAC CGT GTG GTC AGC
          Lys Pro Arg Glu Glu Gln Tyr Asn Ser Thr Tyr Arg Val Val Ser>
          ___e___e___e___e____HUMAN IGG1 FC TAG__e___e___e___e___e___>

1630      1640      1650      1660
            *    *    *    *    *    *    *    *    *
          GTC CTC ACC GTC CTG CAC CAG GAC TGG CTG AAT GGC AAG GAG TAC
          Val Leu Thr Val Leu His Gln Asp Trp Leu Asn Gly Lys Glu Tyr>
          ___e___e___e___e____HUMAN IGG1 FC TAG__e___e___e___e___e___>
```

Fig.14E.

```
        1670          1680          1690          1700          1710
         *     *      *     *      *     *      *     *      *
       AAG TGC AAG GTC TCC AAC AAA GCC CTC CCA GCC CCC ATC GAG AAA
       Lys Cys Lys Val Ser Asn Lys Ala Leu Pro Ala Pro Ile Glu Lys>
       ___e___e___e___e____HUMAN IGG1 FC TAG__e___e___e___e___e___>

1720          1730          1740          1750
               *     *      *     *      *     *      *     *
            ACC ATC TCC AAA GCC AAA GGG CAG CCC CGA GAA CCA CAG GTG TAC
            Thr Ile Ser Lys Ala Lys Gly Gln Pro Arg Glu Pro Gln Val Tyr>
            ___e___e___e___e____HUMAN IGG1 FC TAG__e___e___e___e___e___>

1760          1770          1780          1790          1800
         *     *      *     *      *     *      *     *      *
       ACC CTG CCC CCA TCC CGG GAT GAG CTG ACC AAG AAC CAG GTC AGC
       Thr Leu Pro Pro Ser Arg Asp Glu Leu Thr Lys Asn Gln Val Ser>
       ___e___e___e___e____HUMAN IGG1 FC TAG__e___e___e___e___e___>

1810          1820          1830          1840
               *     *      *     *      *     *      *     *
            CTG ACC TGC CTG GTC AAA GGC TTC TAT CCC AGC GAC ATC GCC GTG
            Leu Thr Cys Leu Val Lys Gly Phe Tyr Pro Ser Asp Ile Ala Val>
            ___e___e___e___e____HUMAN IGG1 FC TAG__e___e___e___e___e___>

1850          1860          1870          1880          1890
         *     *      *     *      *     *      *     *      *
       GAG TGG GAG AGC AAT GGG CAG CCG GAG AAC AAC TAC AAG ACC ACG
       Glu Trp Glu Ser Asn Gly Gln Pro Glu Asn Asn Tyr Lys Thr Thr>
       ___e___e___e___e____HUMAN IGG1 FC TAG__e___e___e___e___e___>

1900          1910          1920          1930
               *     *      *     *      *     *      *     *
            CCT CCC GTG CTG GAC TCC GAC GGC TCC TTC TTC CTC TAC AGC AAG
            Pro Pro Val Leu Asp Ser Asp Gly Ser Phe Phe Leu Tyr Ser Lys>
            ___e___e___e___e____HUMAN IGG1 FC TAG__e___e___e___e___e___>

1940          1950          1960          1970          1980
         *     *      *     *      *     *      *     *      *
       CTC ACC GTG GAC AAG AGC AGG TGG CAG CAG GGG AAC GTC TTC TCA
       Leu Thr Val Asp Lys Ser Arg Trp Gln Gln Gly Asn Val Phe Ser>
       ___e___e___e___e____HUMAN IGG1 FC TAG__e___e___e___e___e___>

1990          2000          2010          2020
               *     *      *     *      *     *      *     *
            TGC TCC GTG ATG CAT GAG GCT CTG CAC AAC CAC TAC ACG CAG AAG
            Cys Ser Val Met His Glu Ala Leu His Asn His Tyr Thr Gln Lys>
            ___e___e___e___e____HUMAN IGG1 FC TAG__e___e___e___e___e___>

2030          2040          2050
         *     *      *     *      *
       AGC CTC TCC CTG TCT CCG GGT AAA TGA
       Ser Leu Ser Leu Ser Pro Gly Lys ***>
       ___e____HUMAN IGG1 FC TAG__e___e___>
```

Fig.15A.

```
         10             20             30             40
          *    *         *    *         *    *         *    *    *
ATG GCC ATG GCC CGG TCC AGG AGG GAC TCT GTG TGG AAG TAC TGT
Met Ala Met Ala Arg Ser Arg Arg Asp Ser Val Trp Lys Tyr Cys>
___a__EPHRIN-B2  ECTO DOMAIN 1 (WITH SIGNAL PEPTIDE)___a___>

50             60             70             80             90
          *    *         *    *         *    *         *    *         *
TGG GGA CTT TTG ATG GTT TTG TGC AGA ACT GCG ATC TCC AGA TCG
Trp Gly Leu Leu Met Val Leu Cys Arg Thr Ala Ile Ser Arg Ser>
___a__EPHRIN-B2  ECTO DOMAIN 1 (WITH SIGNAL PEPTIDE)___a___>

100            110            120            130
          *    *         *    *         *    *         *    *    *
ATA GTT TTA GAG CCT ATC TAC TGG AAT TCC TCG AAC TCC AAA TTT
Ile Val Leu Glu Pro Ile Tyr Trp Asn Ser Ser Asn Ser Lys Phe>
___a__EPHRIN-B2  ECTO DOMAIN 1 (WITH SIGNAL PEPTIDE)___a___>

140            150            160            170            180
          *    *         *    *         *    *         *    *         *
CTA CCC GGA CAA GGC CTG GTA CTA TAC CCA CAG ATA GGA GAC AAA
Leu Pro Gly Gln Gly Leu Val Leu Tyr Pro Gln Ile Gly Asp Lys>
___a__EPHRIN-B2  ECTO DOMAIN 1 (WITH SIGNAL PEPTIDE)___a___>

190            200            210            220
          *    *         *    *         *    *         *    *    *
TTG GAT ATT ATT TGC CCC AAA GTG GAC TCT AAA ACT GTT GGC CAG
Leu Asp Ile Ile Cys Pro Lys Val Asp Ser Lys Thr Val Gly Gln>
___a__EPHRIN-B2  ECTO DOMAIN 1 (WITH SIGNAL PEPTIDE)___a___>

230            240            250            260            270
          *    *         *    *         *    *         *    *         *
TAT GAA TAT TAT AAA GTT TAT ATG GTT GAT AAA GAC CAA GCA GAC
Tyr Glu Tyr Tyr Lys Val Tyr Met Val Asp Lys Asp Gln Ala Asp>
___a__EPHRIN-B2  ECTO DOMAIN 1 (WITH SIGNAL PEPTIDE)___a___>

280            290            300            310
          *    *         *    *         *    *         *    *    *
AGA TGC ACA ATT AAG AAG GAG AAT ACC CCG CTG CTC AAC TGT GCC
Arg Cys Thr Ile Lys Lys Glu Asn Thr Pro Leu Leu Asn Cys Ala>
___a__EPHRIN-B2  ECTO DOMAIN 1 (WITH SIGNAL PEPTIDE)___a___>

320            330            340            350            360
          *    *         *    *         *    *         *    *         *
AGA CCA GAC CAA GAT GTG AAA TTC ACC ATC AAG TTT CAA GAA TTC
Arg Pro Asp Gln Asp Val Lys Phe Thr Ile Lys Phe Gln Glu Phe>
___a__EPHRIN-B2  ECTO DOMAIN 1 (WITH SIGNAL PEPTIDE)___a___>

370            380            390            400
          *    *         *    *         *    *         *    *    *
AGC CCT AAC CTC TGG GGT CTA GAA TTT CAG AAG AAC AAA GAT TAC
Ser Pro Asn Leu Trp Gly Leu Glu Phe Gln Lys Asn Lys Asp Tyr>
___a__EPHRIN-B2  ECTO DOMAIN 1 (WITH SIGNAL PEPTIDE)___a___>
```

Fig.15B.

```
         410         420         430         440         450
          *           *           *           *           *
TAC ATT ATA TCT ACA TCA AAT GGG TCT TTG GAG GGC CTG GAT AAC
Tyr Ile Ile Ser Thr Ser Asn Gly Ser Leu Glu Gly Leu Asp Asn>
___a__EPHRIN-B2  ECTO DOMAIN 1 (WITH SIGNAL PEPTIDE)___a___>

460         470         480         490
          *           *           *           *
CAG GAG GGA GGG GTG TGC CAG ACA AGA GCC ATG AAG ATC CTC ATG
Gln Glu Gly Gly Val Cys Gln Thr Arg Ala Met Lys Ile Leu Met>
___a__EPHRIN-B2  ECTO DOMAIN 1 (WITH SIGNAL PEPTIDE)___a___>

500         510         520         530         540
          *           *           *           *           *
AAA GTT GGA CAA GAT GCA AGT TCT GCT GGA TCA GCC AGG AAT CAC
Lys Val Gly Gln Asp Ala Ser Ser Ala Gly Ser Ala Arg Asn His>
___a__EPHRIN-B2  ECTO DOMAIN 1 (WITH SIGNAL PEPTIDE)___a___>

550         560         570         580
          *           *           *           *
GGT CCA ACA AGA CGT CCA GAG CTA GAA GCT GGT ACA AAT GGG AGA
Gly Pro Thr Arg Arg Pro Glu Leu Glu Ala Gly Thr Asn Gly Arg>
___a__EPHRIN-B2  ECTO DOMAIN 1 (WITH SIGNAL PEPTIDE)___a___>

590         600         610         620         630
          *           *           *           *           *
AGT TCA ACA ACA AGT CCC TTT GTG AAG CCA AAT CCA GGT TCT AGC
Ser Ser Thr Thr Ser Pro Phe Val Lys Pro Asn Pro Gly Ser Ser>
___a__EPHRIN-B2  ECTO DOMAIN 1 (WITH SIGNAL PEPTIDE)___a___>

640         650         660         670
          *           *           *           *
ACC GAT GGC AAC AGC GCG GGG CAT TCC GGG AAC AAT CTC CTG GGG
Thr Asp Gly Asn Ser Ala Gly His Ser Gly Asn Asn Leu Leu Gly>
___a__EPHRIN-B2  ECTO DOMAIN 1 (WITH SIGNAL PEPTIDE)___a___>

680         690         700         710         720
          *           *           *           *           *
GGC CCG GGA ATA GTT TTA GAG CCT ATC TAC TGG AAT TCC TCG AAC
Gly Pro Gly>
___b___b___>
              Ile Val Leu Glu Pro Ile Tyr Trp Asn Ser Ser Asn>
              ___EPHRIN-B2  ECTO DOMAIN 2 ( WITHOUT SIGNA_____>

730         740         750         760
          *           *           *           *
TCC AAA TTT CTA CCC GGA CAA GGC CTG GTA CTA TAC CCA CAG ATA
Ser Lys Phe Leu Pro Gly Gln Gly Leu Val Leu Tyr Pro Gln Ile>
_____EPHRIN-B2  ECTO DOMAIN 2 ( WITHOUT SIGNAL PEPTIDE)_e___>

770         780         790         800         810
          *           *           *           *           *
GGA GAC AAA TTG GAT ATT ATT TGC CCC AAA GTG GAC TCT AAA ACT
Gly Asp Lys Leu Asp Ile Ile Cys Pro Lys Val Asp Ser Lys Thr>
_____EPHRIN-B2  ECTO DOMAIN 2 ( WITHOUT SIGNAL PEPTIDE)_e___>
```

Fig. 15C.

```
         820         830         840         850
          *           *           *           *
GTT GGC CAG TAT GAA TAT TAT AAA GTT TAT ATG GTT GAT AAA GAC
Val Gly Gln Tyr Glu Tyr Tyr Lys Val Tyr Met Val Asp Lys Asp>
____EPHRIN-B2  ECTO DOMAIN 2 ( WITHOUT SIGNAL PEPTIDE)_e___>

860         870         880         890         900
     *           *           *           *           *
CAA GCA GAC AGA TGC ACA ATT AAG AAG GAG AAT ACC CCG CTG CTC
Gln Ala Asp Arg Cys Thr Ile Lys Lys Glu Asn Thr Pro Leu Leu>
____EPHRIN-B2  ECTO DOMAIN 2 ( WITHOUT SIGNAL PEPTIDE)_e___>

910         920         930         940
          *           *           *           *
AAC TGT GCC AGA CCA GAC CAA GAT GTG AAA TTC ACC ATC AAG TTT
Asn Cys Ala Arg Pro Asp Gln Asp Val Lys Phe Thr Ile Lys Phe>
____EPHRIN-B2  ECTO DOMAIN 2 ( WITHOUT SIGNAL PEPTIDE)_e___>

950         960         970         980         990
     *           *           *           *           *
CAA GAA TTC AGC CCT AAC CTC TGG GGT CTA GAA TTT CAG AAG AAC
Gln Glu Phe Ser Pro Asn Leu Trp Gly Leu Glu Phe Gln Lys Asn>
____EPHRIN-B2  ECTO DOMAIN 2 ( WITHOUT SIGNAL PEPTIDE)_e___>

1000        1010        1020        1030
          *           *           *           *
AAA GAT TAC TAC ATT ATA TCT ACA TCA AAT GGG TCT TTG GAG GGC
Lys Asp Tyr Tyr Ile Ile Ser Thr Ser Asn Gly Ser Leu Glu Gly>
____EPHRIN-B2  ECTO DOMAIN 2 ( WITHOUT SIGNAL PEPTIDE)_e___>

1040        1050        1060        1070        1080
     *           *           *           *           *
CTG GAT AAC CAG GAG GGA GGG GTG TGC CAG ACA AGA GCC ATG AAG
Leu Asp Asn Gln Glu Gly Gly Val Cys Gln Thr Arg Ala Met Lys>
____EPHRIN-B2  ECTO DOMAIN 2 ( WITHOUT SIGNAL PEPTIDE)_e___>

1090        1100        1110        1120
          *           *           *           *
ATC CTC ATG AAA GTT GGA CAA GAT GCA AGT TCT GCT GGA TCA GCC
Ile Leu Met Lys Val Gly Gln Asp Ala Ser Ser Ala Gly Ser Ala>
____EPHRIN-B2  ECTO DOMAIN 2 ( WITHOUT SIGNAL PEPTIDE)_e___>

1130        1140        1150        1160        1170
     *           *           *           *           *
AGG AAT CAC GGT CCA ACA AGA CGC CCA GAG CTA GAA GCT GGT ACA
Arg Asn His Gly Pro Thr Arg Arg Pro Glu Leu Glu Ala Gly Thr>
____EPHRIN-B2  ECTO DOMAIN 2 ( WITHOUT SIGNAL PEPTIDE)_e___>

1180        1190        1200        1210
          *           *           *           *
AAT GGG AGA AGT TCA ACA ACA AGT CCC TTT GTG AAG CCA AAT CCA
Asn Gly Arg Ser Ser Thr Thr Ser Pro Phe Val Lys Pro Asn Pro>
____EPHRIN-B2  ECTO DOMAIN 2 ( WITHOUT SIGNAL PEPTIDE)_e___>

1220        1230        1240        1250        1260
     *           *           *           *           *
GGT TCT AGC ACC GAT GGC AAC AGC GCG GGG CAT TCC GGG AAC AAT
Gly Ser Ser Thr Asp Gly Asn Ser Ala Gly His Ser Gly Asn Asn>
____ EPHRIN-B2  ECTO DOMAIN 2 ( WITHOUT SIGNAL PEPTIDE)_e___>
```

Fig. 15D.

```
            1270         1280         1290         1300
             *       *    *       *    *       *    *       *    *
            CTC CTG GGG G GC CCG GGC GAG CCC AAA TCT TGT GAC AAA ACT CAC
                                     Glu Pro Lys Ser Cys Asp Lys Thr His>
                                        c    HUMAN IGG1 FC TAG c    c   >
                         Gly Pro Gly>
                         _d__d___d___>
            Leu Leu Gly Xxx>
              e    e    e_>

1310         1320         1330         1340         1350
             *       *    *       *    *       *    *       *    *
            ACA TGC CCA CCG TGC CCA GCA CCT GAA CTC CTG GGG GGA CCG TCA
            Thr Cys Pro Pro Cys Pro Ala Pro Glu Leu Leu Gly Gly Pro Ser>
              c    c    c    c    HUMAN IGG1 FC TAG c    c    c    c    c    >

1360         1370         1380         1390
             *       *    *       *    *       *    *       *    *
            GTC TTC CTC TTC CCC CCA AAA CCC AAG GAC ACC CTC ATG ATC TCC
            Val Phe Leu Phe Pro Pro Lys Pro Lys Asp Thr Leu Met Ile Ser>
              c    c    c    c    HUMAN IGG1 FC TAG c    c    c    c    c    >

1400         1410         1420         1430         1440
             *       *    *       *    *       *    *       *    *
            CGG ACC CCT GAG GTC ACA TGC GTG GTG GTG GAC GTG AGC CAC GAA
            Arg Thr Pro Glu Val Thr Cys Val Val Val Asp Val Ser His Glu>
              c    c    c    c    HUMAN IGG1 FC TAG c    c    c    c    c    >

1450         1460         1470         1480
             *       *    *       *    *       *    *       *    *
            GAC CCT GAG GTC AAG TTC AAC TGG TAC GTG GAC GGC GTG GAG GTG
            Asp Pro Glu Val Lys Phe Asn Trp Tyr Val Asp Gly Val Glu Val>
              c    c    c    c    HUMAN IGG1 FC TAG c    c    c    c    c    >

1490         1500         1510         1520         1530
             *       *    *       *    *       *    *       *    *
            CAT AAT GCC AAG ACA AAG CCG CGG GAG GAG CAG TAC AAC AGC ACG
            His Asn Ala Lys Thr Lys Pro Arg Glu Glu Gln Tyr Asn Ser Thr>
              c    c    c    c    HUMAN IGG1 FC TAG c    c    c    c    c    >

1540         1550         1560         1570
             *       *    *       *    *       *    *       *    *
            TAC CGT GTG GTC AGC GTC CTC ACC GTC CTG CAC CAG GAC TGG CTG
            Tyr Arg Val Val Ser Val Leu Thr Val Leu His Gln Asp Trp Leu>
              c    c    c    c    HUMAN IGG1 FC TAG c    c    c    c    c    >

1580         1590         1600         1610         1620
             *       *    *       *    *       *    *       *    *
            AAT GGC AAG GAG TAC AAG TGC AAG GTC TCC AAC AAA GCC CTC CCA
            Asn Gly Lys Glu Tyr Lys Cys Lys Val Ser Asn Lys Ala Leu Pro>
              c    c    c    c    HUMAN IGG1 FC TAG c    c    c    c    c    >

1630         1640         1650         1660
             *       *    *       *    *       *    *       *    *
            GCC CCC ATC GAG AAA ACC ATC TCC AAA GCC AAA GGG CAG CCC CGA
            Ala Pro Ile Glu Lys Thr Ile Ser Lys Ala Lys Gly Gln Pro Arg>
              c    c   _c   _c    HUMAN IGG1 FC TAG c    c    c    c    c    >
```

Fig.15E.

```
         1670         1680         1690         1700         1710
          *    *    *    *    *    *    *    *    *
        GAA  CCA  CAG  GTG  TAC  ACC  CTG  CCC  CCA  TCC  CGG  GAT  GAG  CTG  ACC
        Glu  Pro  Gln  Val  Tyr  Thr  Leu  Pro  Pro  Ser  Arg  Asp  Glu  Leu  Thr>
        ___c___c___c___c____HUMAN IGG1 FC TAG__c___c___c___c___c___>

1720         1730         1740         1750
               *    *    *    *    *    *    *    *    *
        AAG  AAC  CAG  GTC  AGC  CTG  ACC  TGC  CTG  GTC  AAA  GGC  TTC  TAT  CCC
        Lys  Asn  Gln  Val  Ser  Leu  Thr  Cys  Leu  Val  Lys  Gly  Phe  Tyr  Pro>
        ___c___c___c___c____HUMAN IGG1 FC TAG__c___c___c___c___c___>

1760         1770         1780         1790         1800
          *    *    *    *    *    *    *    *    *    *
        AGC  GAC  ATC  GCC  GTG  GAG  TGG  GAG  AGC  AAT  GGG  CAG  CCG  GAG  AAC
        Ser  Asp  Ile  Ala  Val  Glu  Trp  Glu  Ser  Asn  Gly  Gln  Pro  Glu  Asn>
        ___c___c___c___c____HUMAN IGG1 FC TAG__c___c___c___c___c___>

1810         1820         1830         1840
               *    *    *    *    *    *    *    *    *
        AAC  TAC  AAG  ACC  ACG  CCT  CCC  GTG  CTG  GAC  TCC  GAC  GGC  TCC  TTC
        Asn  Tyr  Lys  Thr  Thr  Pro  Pro  Val  Leu  Asp  Ser  Asp  Gly  Ser  Phe>
        ___c___c___c___c____HUMAN IGG1 FC TAG__c___c___c___c___c___>

1850         1860         1870         1880         1890
          *    *    *    *    *    *    *    *    *    *
        TTC  CTC  TAC  AGC  AAG  CTC  ACC  GTG  GAC  AAG  AGC  AGG  TGG  CAG  CAG
        Phe  Leu  Tyr  Ser  Lys  Leu  Thr  Val  Asp  Lys  Ser  Arg  Trp  Gln  Gln>
        ___c___c___c___c____HUMAN IGG1 FC TAG__c___c___c___c___c___>

1900         1910         1920         1930
               *    *    *    *    *    *    *    *    *
        GGG  AAC  GTC  TTC  TCA  TGC  TCC  GTG  ATG  CAT  GAG  GCT  CTG  CAC  AAC
        Gly  Asn  Val  Phe  Ser  Cys  Ser  Val  Met  His  Glu  Ala  Leu  His  Asn>
        ___c___c___c___c____HUMAN IGG1 FC TAG__c___c___c___c___c___>

1940         1950         1960         1970
          *    *    *    *    *    *    *    *
        CAC  TAC  ACG  CAG  AAG  AGC  CTC  TCC  CTG  TCT  CCG  GGT  AAA  TGA
        His  Tyr  Thr  Gln  Lys  Ser  Leu  Ser  Leu  Ser  Pro  Gly  Lys  ***>
        ___c___c___c___c__HUMAN IGG1 FC TAG____c___c___c___c___>
```

METHOD OF ENHANCING THE BIOLOGICAL ACTIVITY OF LIGANDS

This application is a National Stage of International Application No. PCT/US99/30900, filed Dec. 23, 1999, which claims the benefit under 35 U.S.C. § 119 (e) of U.S. Provisional Application No. 60/113,387, filed Dec. 23, 1998.

The present invention provides for novel methods for producing novel fusion polypeptide ligands that have enhanced biological activity as compared to the polypeptide ligands in their native form. The invention also provides for nucleic acids useful for producing biologically active fusion polypeptide ligands, and the fusion polypeptide ligands themselves.

BACKGROUND OF THE INVENTION

The ability of polypeptide ligands to bind cells and thereby elicit a phenotypic response such as cell growth, survival or differentiation is often mediated through transmembrane tyrosine kinases. The extracellular portion of each receptor tyrosine kinase (RTK) is generally the most distinctive portion of the molecule, as it provides the protein with its ligand-recognizing characteristic. Binding of a ligand to the extracellular domain results in signal transduction via an intracellular tyrosine kinase catalytic domain which transmits a biological signal to intracellular target proteins. The particular array of sequence motifs of this cytoplasmic, catalytic domain determines its access to potential kinase substrates (Mohammadi, et al., 1990, Mol. Cell. Biol., 11: 5068–5078; Fantl, et al., 1992, Cell, 69:413–413).

RTKs appear to undergo dimerization or some related conformational change following ligand binding (Schlessinger, J., 1988, Trend Biochem. Sci. 13:443–447; Ullrich and Schlessinger, 1990, Cell, 61:203–212; Schlessinger and Ullrich, 1992, Neuron 9:383–391); molecular interactions between dimerizing cytoplasmic domains lead to activation of kinase function. In some instances, such as the growth factor platelet derived growth factor (PDGF), the ligand is a dimer that binds two receptor molecules (Hart, et al., 1988, Science, 240: 1529–1531; Heldin, 1989, J. Biol. Chem. 264:8905–8912) while, for example, in the case of EGF, the ligand is a monomer (Weber, et al., 1984, J. Biol. Chem., 259:14631–14636).

Throughout the history of the biotechnology industry, many novel genes and associated proteins have been identified by virtue of their sequence homology with known genes. Many such proteins are purported to be receptors, but since their cognate ligands have not been identified, they are referred to as orphan receptors. The screening of many of these orphan receptors often leads to the identification of ligands that are capable of binding to the receptor, although the binding is often not associated with activation of any intracellular kinases or any other phenotypic change. Such was the case for members of the Eph receptor family. For sake of clarity, applicants incorporate by reference herein a letter cited as Eph Nomenclature Committee, 1997, published in Cell vol. 90: 403–403 (1997) which sets forth a nomenclature for the Eph Receptor and Eph Ligand Families.

Little, if any, biological activity had been observed in response to binding of a ligand to an Eph family receptor prior to the discovery as set forth in U.S. Pat. No. 5,747,033 issued May 5, 1998. That patent describes the concept of "clustering" whereby the soluble domains of ligands were combined to create multimers capable of activating the cognate receptors. Applicants have now extended the concept of clustering to additional ligands outside the Eph family, for example, the Tie-2 receptor ligands known as the angiopoietins, and have also discovered that this method for production of homogeneous forms of clustered ligands is broadly applicable to improve the affinity and/or increase the activity of a ligand as compared to the native form of the ligand.

Angiopoietin-1 (Ang) is one of two known ligands for the Tie-2 receptor and has been shown to be an agonist for Tie-2 (Davis, et al, 1996, Cell 87:1161–1169), whereas the second known ligand, angiopoietin-2, has been shown to be a naturally occurring antagonist of the Tie-2 receptor (Maisonpierre, et al., 1997, Science 277:55–60). Ang1* is a mutant form of angiopoietin-1 that comprises the N-terminal domain of angiopoietin-2 fused to the coiled-coil domain and the fibrinogen domain of angiopoietin-1 and that has a Cys to Ser mutation at amino acid 245. Ang1* has been shown to be a potent agonist for the Tie-2 receptor.

Experiments with mutants of angiopoietin-1 and angiopoietin-2 have demonstrated that the fibrinogen domains (FD) are the receptor-binding domains, and that dimerized versions of, for example Ang-1-FD-Fc, (i.e., the fibrinogen domain of Ang-1 fused to an Fc domain), can bind to the Tie-2 receptor with much higher affinity than monomeric Ang-1-FD (dimerization occurs due to the interaction between the Fc components of adjacent molecules). However, Ang-1-FD-Fc is not able to induce phosphorylation (activate) the Tie-2 receptor on endothelial cells unless it is further clustered with goat anti-human Fc antibodies (Jackson Immunoresearch). For this reason, mutant versions of Ang-1-FD and Ang-2-FD (i.e., the fibrinogen domain of Ang-2) were designed that were intrinsically more highly clustered.

SUMMARY OF THE INVENTION

The present invention provides for novel, biologically active, soluble forms of polypeptide ligands that bind to receptors on cells. Such polypeptide ligands are useful in promoting a differential function and/or influencing the phenotype, such as growth and/or proliferation, of receptor-bearing cells. The invention also provides for nucleic acids encoding such polypeptide ligands, and both prokaryotic and eukaryotic expression systems for producing such polypeptide ligands. According to the invention, soluble forms of the polypeptide ligands described herein may be used to promote biological responses in receptor-expressing cells. In particular, a general method is described herein which produces fusion polypeptide ligands that may then be clustered, which functions to make otherwise inactive soluble polypeptide ligands biologically active, or which enhances the biological activity of polypeptide ligands that, absent such clustering, would have lower levels of biological activity. This method may be used to cluster a plurality of (more than one) receptor binding domains from any ligand which has improved affinity and/or increased activity (i.e. signaling ability) when clustered as compared to the native form of the ligand.

DESCRIPTION OF THE FIGURES

FIGS. 1A–1E (SEQ ID NOS: 1 and 2)—Nucleic acid sequence (SEQ ID NO: 1) and deduced amino acid sequence (SEQ ID NO: 2) of Ang-1-FD-FD-Fc.

FIGS. 2A–2E (SEQ ID NOS: 3 and 4)—Nucleic acid sequence (SEQ ID NO: 3) and deduced amino acid sequence (SEQ ID NO: 4) of Ang-2-FD-FD-Fc.

FIGS. 3A–3E (SEQ ID NOS: 5 and 6)—Nucleic acid sequence (SEQ ID NO: 5) and deduced amino acid sequence (SEQ ID NO: 6) of Ang-1-FD-Fc-FD.

FIGS. 4A–4E (SEQ ID NOS: 7 and 8)—Nucleic acid sequence (SEQ ID NO: 7) and deduced amino acid sequence (SEQ ID NO: 8) of Ang-2-FD-Fc-FD.

FIGS. 14A–14E (SEQ ID NOS: 9 and 10)—Nucleic acid sequence (SEQ ID NO: 9) and deduced amino acid sequence (SEQ ID NO: 10) of Ephrin-B1-Ephrin-B1-Fc.

FIGS. 15A–15E (SEQ ID NOS: 11 and 12)—Nucleic acid sequence (SEQ ID NO: 11) and deduced amino acid sequence (SEQ ID NO: 12) of Ephrin-B2-Ephrin-B2-Fc.

DETAILED DESCRIPTION OF THE INVENTION

Figure 5:
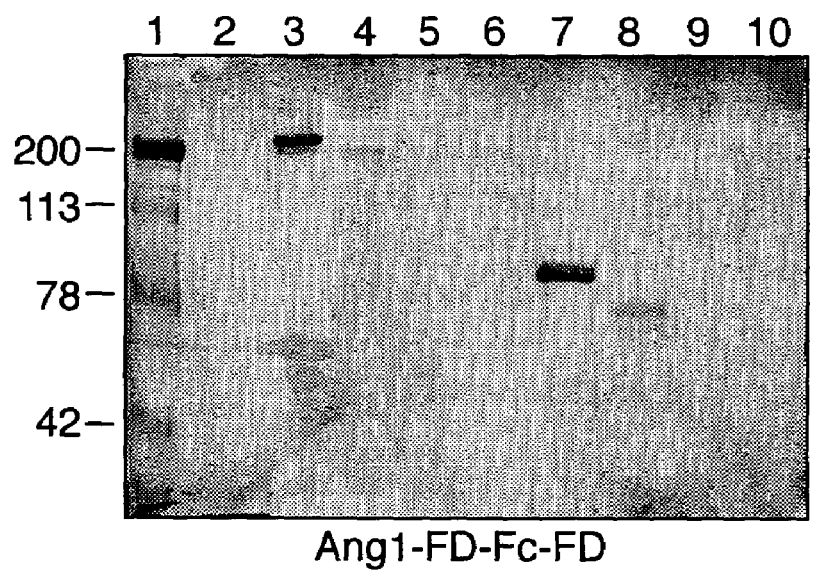
FIG. 5—Molecular Weight Analysis of Ang-1-FD-Fc-FD protein. SDS PAGE analyses showing a band running at about 210 kD under non-reducing conditions (lane 3) and a band running at about 85 kD under reducing conditions (lane 7).

As described in greater detail below, applicants have discovered a method for "clustering" polypeptide ligands, which functions to make otherwise inactive soluble polypeptide ligands biologically active, or which enhances the biological activity of polypeptide ligands that, absent such clustering, would have lower levels of biological activity. This method may be used to cluster a plurality of (more than one) receptor binding domains from any ligand which has improved affinity and/or increased activity (i.e. signaling ability) when clustered as compared to the native form of the ligand.

The present invention provides for a nucleic acid encoding a fusion polypeptide wherein the fusion polypeptide comprises a first subunit comprising at least one copy of the receptor binding domain of a ligand, the first subunit being fused to the N-terminal end of a multimerizing component, said multimerizing component being fused at its C-terminal end to a second subunit comprising at least one copy of the receptor binding domain of a ligand.

In one embodiment of the invention, the receptor binding domains of the first and second subunits are copies of the receptor binding domain of the same ligand. The first and second subunits may each have one or more than one copy of the receptor binding domain of the ligand. In specific embodiments of the invention, the receptor binding domain is the fibrinogen domain of angiopoietin-1 or angiopoietin-2. Alternatively, the receptor binding domain is from a ligand selected from the group consisting of the EPH family of ligands (i.e., the ephrins).

In another embodiment of the invention, the receptor binding domains of the first subunit are copies of the receptor binding domain of a different ligand from the receptor binding domains of the second subunit. For example, the first subunit may comprise the receptor binding domain of an angiopoietin and the second subunit may comprise the receptor binding domain of vascular endothelial growth factor (VEGF). Alternatively, the first subunit may comprise the receptor binding domain of VEGF and the second subunit may comprise the receptor binding domain an angiopoietin. Still further, the first and second subunits may each have one or more than one copy of the receptor binding domain of their respective ligand.

By "receptor binding domain" what is meant is the minimal portion of the ligand that is necessary to bind its receptor.

In preferred embodiments of the invention, the multimerizing component comprises an immunoglobulin derived domain. More specifically, the immunoglobulin derived domain may be selected from the group consisting of the Fc domain of IgG, the heavy chain of IgG, and the light chain of IgG. In another embodiment, the multimerizing component may be an Fc domain from which the first five amino acids (including a cysteine) have been removed to produce a multimerizing component referred to as Fc(ΔC1).

The present invention also provides for fusion polypeptides encoded by the nucleic acid molecules of the invention. Preferably, the fusion polypeptides are in multimeric form, due to the function of the multimerizing component. In a preferred embodiment, the multimer is a dimer. Suitable multimerizing components are described in European Patent Application of ZymoGenetics, Inc., Publication No. EP 0 721 983 A1 published 17 Jul. 1996 and, include *S. cerevisiae* repressible acid phosphatase (Mizunaga et al., 1988, J. Biochem. (Tokyo) 103:321–326); the *S. cerevisiae* type 1 killer preprotoxin (Sturley et al., 1986, EMBO J. 5:3381–3390); the *S. calsbergensis* alpha galactosidase melibiase (Sumner-Smith, et al., 1985, Gene 36:333–340); and the *Neurospora crassa* ornithine decarboxylase (Digangi, et al., 1987, J. Biol. Chem. 262:7889–7893). Sequences encoding an immunoglobulin heavy chain hinge region (Takahashi et al., 1982, Cell 29:671–679); the *S. cerevisiae* SUC2 gene (Carlson et al., 1983, Mol. Cell. Biol. 3:439–447); immunoglobulin gene sequences, and portions thereof. In a preferred embodiment of the invention, immunoglobulin gene sequences, especially one encoding the Fc domain, are used to encode the multimerizing component.

The present invention also contemplates a vector which comprises the nucleic acid molecule of the invention as described herein.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector systems described herein, under conditions permitting production of the fusion polypeptide and recovering the fusion polypeptide so produced.

The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pCP110.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The present invention also provides for a nucleic acid encoding a fusion polypeptide wherein the fusion polypeptide comprises more than one copy of the receptor binding domain of a ligand in tandem, and wherein either the N-terminal or the C-terminal receptor binding domain is also fused to a multimerizing component. In one embodiment of the invention, the receptor binding domains are fused contiguously. In another embodiment of the invention, the receptor binding domains are from a ligand that is not a member of the EPH family of ligands (i.e., not an ephrin). In specific embodiments of the invention, the receptor binding domain is the fibrinogen domain of angiopoietin-1 or angiopoietin-2. In an alternative embodiment, the receptor binding domain is from vascular endothelial growth factor (VEGF). In another embodiment, the receptor binding domain is from an ephrin.

By "receptor binding domain" what is meant is the minimal portion of the ligand that is necessary to bind its receptor.

In preferred embodiments of the invention, the multimerizing component comprises an immunoglobulin derived domain. More specifically, the immunoglobulin derived domain may be selected from the group consisting of the Fc domain of IgG, the heavy chain of IgG, and the light chain of IgG. In another embodiment, the multimerizing component may be an Fc domain from which the first five amino acids (including a cysteine) have been removed to produce a multimerizing component referred to as Fc(ΔC1).

The present invention also provides for fusion polypeptides encoded by the nucleic acid molecules of the invention. Preferably, the fusion polypeptides are in multimeric form, due to the function of the multimerizing component. In a preferred embodiment, the multimer is a dimer. Suitable multimerizing components are described in European Patent Application of ZymoGenetics, Inc., Publication No. EP 0 721 983 A1 published 17 Jul. 1996 and include *S. cerevisiae* repressible acid phosphatase (Mizunaga et al., 1988, J. Biochem. (Tokyo) 103:321–326); the *S. cerevisiae* type 1 killer preprotoxin (Sturley et al., 1986, EMBO J. 5:3381–3390); the *S. calsbergensis* alpha galactosidase melibiase (Sumner-Smith, et al., 1985, Gene 36:333–340); and the *Neurospora crassa* ornithine decarboxylase (Digangi, et al., 1987, J. Biol. Chem. 262:7889–7893). Sequences encoding an immunoglobulin heavy chain hinge region (Takahashi et al., 1982, Cell 29:671–679); the *S. cerevisiae* SUC2 gene (Carlson et al., 1983, Mol. Cell. Biol. 3:439–447); immunoglobulin gene sequences, and portions thereof. In a preferred embodiment of the invention, immunoglobulin gene sequences, especially one encoding the Fc domain, are used to encode the multimerizing component.

The present invention also contemplates a vector which comprises the nucleic acid molecule of the invention as described herein.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector systems described herein, under conditions permitting production of the fusion polypeptide and recovering the fusion polypeptide so produced.

The fusion polypeptides useful for practicing the present invention may be prepared by expression in a prokaryotic or eukaryotic expression system. The recombinant gene may be expressed and the polypeptide purified utilizing any number of methods. The gene may be subcloned into a bacterial expression vector, such as for example, but not by way of limitation, pCP110.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The Examples describe the preparation of novel polypeptide ligands that comprise a receptor binding domain of a member of the Eph (Eph transmembrane tyrosine kinase family ligands) family of ligands or of a member of the angiopoietin family of ligands that can bind the Tie-2 receptor.

For a description of novel Eph family ligands, methods of making and using them, as well as the sequences of EHK-1L, B61 and ELK-L, together with a description of a method of enhancing the biological activity of EPH family ligands by clustering them, applicants refer to U.S. Pat. No. 5,747,033 issued on May 5, 1998 which is hereby incorporated by reference in its entirety. Applicants further refer to International Application PCT/US93/10879, published as WO 94/11020 on May 26, 1994; and International Application PCT/US96/17201 published as WO 97/15667 entitled "Biologically Active EPH Family Ligands" each of which is hereby incorporated by reference in its entirety.

As has been previously reported, a family of ligands for the TIE-2 receptor has been discovered and named the Angiopoietins. This family, consisting of TIE-2 ligand 1' (Ang-1); TIE-2 ligand 2 (Ang-2); TIE ligand 3 (Ang-3); and TIE ligand 4 (Ang-4) has been extensively characterized. For a description of the cloning, sequencing and characterization of the angiopoietins, as well as for methods of making and uses thereof, including the production and characterization of modified and chimeric ligands thereof, reference is hereby made to the following publications, each of which is incorporated by reference herein in its entirety: U.S. Pat. No. 5,521,073 issued May 28, 1996; U.S. Pat. No. 5,643,755 issued Jul. 1, 1997; U.S. Pat. No. 5,650,490 issued Jul. 22, 1997; U.S. Pat. No. 5,814,464 issued Sep. 29, 1998; U.S. Pat. No. 5,879,672 issued Mar. 9, 1999; U.S. Pat. No. 5,851,797 issued Dec. 22, 1998; PCT International Application entitled "TIE-2 Ligands Methods of Making and Uses Thereof," published as WO 96/11269 on 18 Apr. 1996 in the name of Regeneron Pharmaceuticals, Inc.; PCT International Application entitled "TIE-2 Ligands Methods of Making and Uses Thereof,"published as WO 96/31598 on 10 Oct. 1996 in the name of Regeneron Pharmaceuticals, Inc.; PCT International Application entitled "TIE-2 Receptor Ligands (TIE Ligand-3. TIE Ligand-4) And Their Uses," published as WO 97/48804 on 24 Dec. 1997 in the name of Regeneron Pharmaceuticals, Inc; and PCT International Application entitled "Modified TIE-2 Receptor Ligands," published as WO 98/05779 on 12 Feb. 1998 in the name of Regeneron Pharmaceuticals, Inc.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electroporation, or microinjection.

The present invention encompasses the nucleic acid sequences encoding the fusion polypeptides of the invention, as well as sequences that hybridize under stringent conditions to nucleic acid sequences that are complementary to the nucleic acid sequences of the invention. Stringent conditions are set forth in, for example, Sambrook, et al. Molecular Cloning: A Laboratory Manual, 2 ed. Vol. 1, pp. 101–104, Cold Spring Harbor Laboratory Press (1989). In addition, the present invention encompasses nucleic acid sequences that are different from the nucleic acid sequences of the invention but which nevertheless encode the fusion polypeptides of the invention due to the degeneracy of the genetic code.

In addition, the present invention contemplates use of the fusion polypeptides described herein in tagged forms.

Any of the methods known to one skilled in the art for the insertion of DNA fragments into a vector may be used to construct expression vectors encoding the fusion polypeptides of the invention using appropriate transcriptional/translational control signals and the protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionein gene (Brinster et al., 1982, Nature 296:39–42); prokaryotic expression vectors such as the b-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK, (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring. Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et. al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378).

Thus, according to the invention, expression vectors capable of being replicated in a bacterial or eukaryotic host comprising Eph fusion polypeptide encoding or angiopoietin fusion polypeptide encoding nucleic acids as described herein, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor. Such biologically active forms would, for example, induce phosphorylation of the tyrosine kinase domain of the Ehk-1, Elk, or Tie2 receptor, or stimulation of synthesis of cellular DNA.

Expression vectors containing the nucleic acid inserts can be identified by three general approaches: (a) DNA—DNA hybridization, (b) presence or absence of "marker" gene functions, and (c) expression of inserted sequences. In the first approach, the presence of a foreign nucleic acids inserted in an expression vector can be detected by DNA—DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

Cells of the present invention may transiently or, preferably, constitutively and permanently express the ephrin or angiopoietin fusion polypeptide as described herein.

The ephrin fusion polypeptides of the invention may be useful in methods of treating a patient suffering from a neurological disorder comprising treating the patient with an effective amount of the ephrin fusion polypeptide.

For example, the Elk receptor is expressed primarily in brain. Accordingly, it is believed that an Elk binding ephrin fusion polypeptide ligand will support the induction of a differential function and/or influence the phenotype, such as growth and/or survival of neural cells that express this receptor.

The present invention also provides for pharmaceutical compositions comprising the ephrin fusion polypeptide in a suitable pharmacologic carrier. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understanding of neurodegenerative disease/neurotrauma becomes clearer, it may become apparent that it would be beneficial to decrease the effect of endogenous Efl-6. Therefore, in areas of nervous system trauma, it may be desirable to provide Efl-6 antagonists, including, but not limited to, fusion polypeptide forms of Efl-6 which may compete with cell-bound ligand for interaction with Elk receptor. It may be desirable to provide such antagonists locally at the injury site rather than systemically. Use of an Efl-6 antagonist providing implant may be desirable.

Alternatively, certain conditions may benefit from an increase in Efl-6 responsiveness. It may therefore be beneficial to increase the number or binding affinity of Efl-6 in patients suffering from such conditions.

The invention herein further provides for the development of a fusion polypeptide, as a therapeutic for the treatment of patients suffering from disorders involving cells, tissues or organs which express the TIE-2 receptor. Such molecules may be used in a method of treatment of the human or animal body, or in a method of diagnosis.

Because TIE-2 receptor has been identified in association with, endothelial cells and, as was previously demonstrated, blocking of agonists of the receptor such as TIE-2 ligand 1 (Ang-1) has been shown to prevent vascularization, applicants expect that TIE-2 agonist fusion polypeptides of the invention may be useful for the induction of vascularization in diseases or disorders where such vascularization is indicated. Such diseases or disorders would include wound healing, ischemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671 issued Jul. 26, 1994'. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al., European Patent Application 0 550 296 A2 published Jul. 7, 1993; Banai, et al. Circulation 89:2183–2189 (1994); Unger, et al. Am. J. Physiol. 266:H1588–H1595 (1994); Lazarous, et al. Circulation 91:145–153 (1995)]. According to the invention, the agonist fusion polypeptides may be used alone or in combination with one or more additional pharmaceutically active compounds such as, for example, VEGF or basic fibroblast growth factor (bFGF).

Conversely, antagonists of the TIE-2 receptor, such as TIE-2 receptorbodies or TIE-2 ligand 2 (Ang-2) as described in Example 9 in International Publication No. WO 96/31598 published 10 Oct. 1996, have been shown to prevent or attenuate vascularization, and are thus expected to be useful in preventing or attenuating, for example, tumor growth. Similarly then, TIE-2 antagonist fusion polypeptides of the invention would also be useful for those purposes. These antagonists may be used alone or in combination with other compositions, such as anti-VEGF antibodies, that have been shown to be useful in treating conditions in which the therapeutic intent is to block angiogenesis.

For example, applicants have determined that TIE-2 ligands are expressed in cells within, or closely associated with, tumors. For example, TIE-2 ligand 2 (Ang-2) appears to be tightly associated with tumor endothelial cells. Accordingly, TIE-2 antagonist fusion polypeptides of the invention may also be useful in preventing or attenuating, for example, tumor growth.

In other embodiments, the TIE-2 agonist fusion polypeptides of the invention described herein may be used as hematopoietic factors. A variety of hematopoietic factors and their receptors are involved in the proliferation and/or differentiation and/or migration of the various cells types contained within blood. Because the TIE-2 receptors are expressed in early hematopoietic cells, the TIE-2 ligands are expected to play a comparable role in the proliferation or differentiation or migration of these cells. Thus, for example, TIE-2 agonist fusion polypeptide compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. Natl. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly, the fusion polypeptides may be used to diagnose or treat conditions in which normal hematopoiesis is suppressed, including, but not limited to anemia, thrombocytopenia, leukopenia and granulocytopenia. In a preferred embodiment, the fusion polypeptides may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The fusion polypeptides of the present invention may be used alone, or in combination with another pharmaceutically active agents such as, for example, cytokines, neurotrophins, interleukins, etc. In a preferred embodiment, the fusion polypeptides may be used in conjunction with any of a number of factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE-2 receptor antagonist fusion polypeptides are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the fusion polypeptides as described herein.

Effective doses useful for treating these or other diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

EXAMPLES

Angiopoietin Ligands:

As described supra, experiments with mutants of Ang-1 and Ang-2 have demonstrated that the fibrinogen domains (FD) are the receptor-binding domains, and that dimerized versions (dimerization occurs due to the interaction between the Fc components of adjacent molecules), for example Ang-1-FD-Fc, can bind to the Tie-2 receptor with much higher affinity than monomeric Ang-1-FD. However, Ang-1-FD-Fc is not able to induce phosphorylation (activate) the Tie-2 receptor on endothelial cells unless it is further clustered with goat anti-human Fc antibodies (Jackson Immunoresearch). For this reason, mutant versions of Ang-1-FD and Ang-2-FD were designed that were intrinsically more highly clustered.

Two general types of nucleic acid molecules were constructed. The first type consisted of two tandem copies of Ang-1-FD fused to an Fc tag, thus leading to a secreted polypeptide molecule that is dimeric with respect to the Fc tag but tetrameric with respect to Ang-1-FD. Similarly, two tandem copies of Ang-2-FD fused to an Fc tag constituted the angiopoietin-2 version of this type of construct. These molecules were designated Ang-1-FD-FD-Fc and Ang-2-FD-FD-Fc, respectively.

In the second type of nucleic acid molecule constructed, two copies of Ang-1-FD were connected by an Fc tag bridging between them, thus creating the structure Ang-1-FD-Fc-FD that is still dimeric with respect to the Fc, as well as tetrameric with respect to Ang-1-FD. An angiopoietin-2 version was also constructed and these two molecules were designated Ang-1-FD-Fc-FD and Ang-2-FD-Fc-FD, respectively.

For either type of construct, similar properties were observed: unlike dimeric Ang-1-FD-Fc, which fails to activate Tie-2 in endothelial cells, both Ang-1-FD-FD-Fc and Ang-1-FD-Fc-FD could readily activate Tie-2 in endothelial cells, with a potency comparable to that of the native ligand. Also, like native angiopoietin-2, Ang-2-FD-Fc-FD could antagonize angiopoietin-1 activity with a potency that is comparable to that of native angiopoietin-2, and with much greater potency than the marginally antagonistic activity of the Ang-2-FD-Fc dimer.

Construction of Mutant Angiopoietin Nucleic Acid Molecules.

All of the following nucleic acid molecules were constructed by standard recombinant DNA techniques (See e.g., Molecular Cloning, A Laboratory Manual (Sambrook, et al., Cold Spring Harbor Laboratory, Cold Spring Harbor, N.Y.), Current Protocols in Molecular Biology (Eds. Ausubel, et al., Greene Publ. Assoc., Wiley-Interscience, NY), sequence-verified by standard techniques using an ABI 373A DNA sequencer and Taq Dideoxy Terminator Cycle Sequencing Kit (Applied Biosystems, Inc., Foster City, Calif.), and subcloned into the mammalian expression vector pMT21 (Genetics Institute, Inc.) with a Kozak sequence (Kozak, M., 1987, Nucleic Acids Res. 15:8125–8148) at the 5' end to promote protein translation. The bridging sequences described infra were introduced to provide convenient restriction sites and to give flexibility to the junctions between the domains, but there is no indication that there is a very critical nature to these bridging sequences (though varying the length of the linker in some of these constructs led to some variation in the amount of protein produced).

Example 1

Construction of the Ang-1-FD-FD-Fc, Ang-2-FD-FD-Fc, Ang-1-FD-Fc-FD, and Ang-2-FD-Fc-FD Nucleic Acid Molecules Ang-1-FD-FD-Fc: Ang-1-FD-FD-Fc consists of a trypsin signal sequence at its amino terminus to allow for secretion (bases 1–45 of FIG. 1A [SEQ ID NO: 1]) followed by the angiopoietin-1 fibrinogen domain (FD) (bases 46–690 of FIG. 1A–FIG. 1B [SEQ ID NO: 1]), a short bridging sequence consisting of the amino acids Gly-Pro Ala-Pro (SEQ ID NO: 13) (bases 691–702 of FIG. 1B [SEQ ID NO: 1]), a second angiopoietin-1 FD (bases 703–1750 of FIG. 1B–FIG. 1D [SEQ ID NO: 1])), another bridging sequence consisting of the amino acids Gly-Pro-Gly (bases 1351–1359 of FIG. 1D [SEQ ID NO: 1]), and the coding sequence for the Fc portion of human IgG1 (bases 1360–2058 of FIG. 1D–FIG. 1E [SEQ ID NO: 1]).

Ang-2-FD-FD-Fc: The Ang-2-FD-FD-Fc nucleic acid molecule was similarly constructed. It consists of a trypsin signal sequence (bases 1–45 of FIG. 2A [SEQ ID NO: 3]), an angiopoietin-2 FD (bases 46–690 of FIG. 2A–FIG. 2B [SEQ ID NO: 3]), a bridging amino acid sequence Gly-Gly-Pro-Ala-Pro (SEQ ID NO: 14) (bases 691–705 of FIG. 2B [SEQ ID NO: 3]), a second angiopoietin-2 FD (bases 706–1353 of FIG. 2B–FIG. 2D [SEQ ID NO: 3]), another bridging amino acid sequence Gly-Pro-Gly (bases 1354–1362 of FIG. 2D [SEQ ID NO: 3]), and the coding sequence for the Fc portion of human IgG1 (bases 1363–2061 of FIG. 2D–FIG. 2E [SEQ ID NO: 3]).

Ang-1-FD-Fc-FD: The Ang-1-FD-Fc-FD consists of a trypsin signal sequence (bases 1–45 of FIG. 3A [SEQ ID NO: 5]), an angiopoietin-1 FD (bases 46–690 of FIGS. 3A–3B [SEQ ID NO: 5]), the bridging amino acid sequence Gly-Pro-Gly (bases 691–699 of FIG. 3B [SEQ ID NO: 5]), the coding sequence for the Fc portion of human IgG1 (bases 700–1395 of FIGS. 3B–3D [SEQ ID NO: 5]), another bridging amino acid sequence Gly-Gly-Gly-Gly-Ser-Gly-Ala-Pro (SEQ ID NO: 15) (bases 1396–1419 of FIG. 3D [SEQ ID NO: 5]), and a second angiopoietin-1 FD (bases 1420–2067 of FIG. 3D–FIG. 3E [SEQ ID NO: 5]).

Ang-2-FD-Fc-FD: The Ang-2-FD-Fc-FD nucleic acid molecule consists of a trypsin signal sequence (bases 1–45 of FIG. 4A [SEQ ID NO: 7]), an angiopoietin-2 FD domain (bases 46–690 of FIG. 4A–FIG. 4B [SEQ ID NO: 7]), the bridging amino acid sequence Gly-Gly-Pro-Gly (SEQ ID NO: 16) (bases 691–702 of FIG. 4B [SEQ ID NO: 7]), the coding sequence for the Fc portion of human IgG1 (bases 703–1398 of FIG. 4B–FIG. 4D [SEQ ID NO: 7), the bridging amino acid sequence Gly-Gly-Gly-Gly-Ser-Gly-Ala-Pro (SEQ ID NO: 15) bases 1399–1422 of FIG. 4D [SEQ ID NO: 7]), and a second angiopoietin-2 FD (bases 1423–2067 of FIG. 4D–FIG. 4E [SEQ ID NO: 7]).

Example 2

Characterization of Ang-1 FD-Fc-FD Protein

Figure 6:
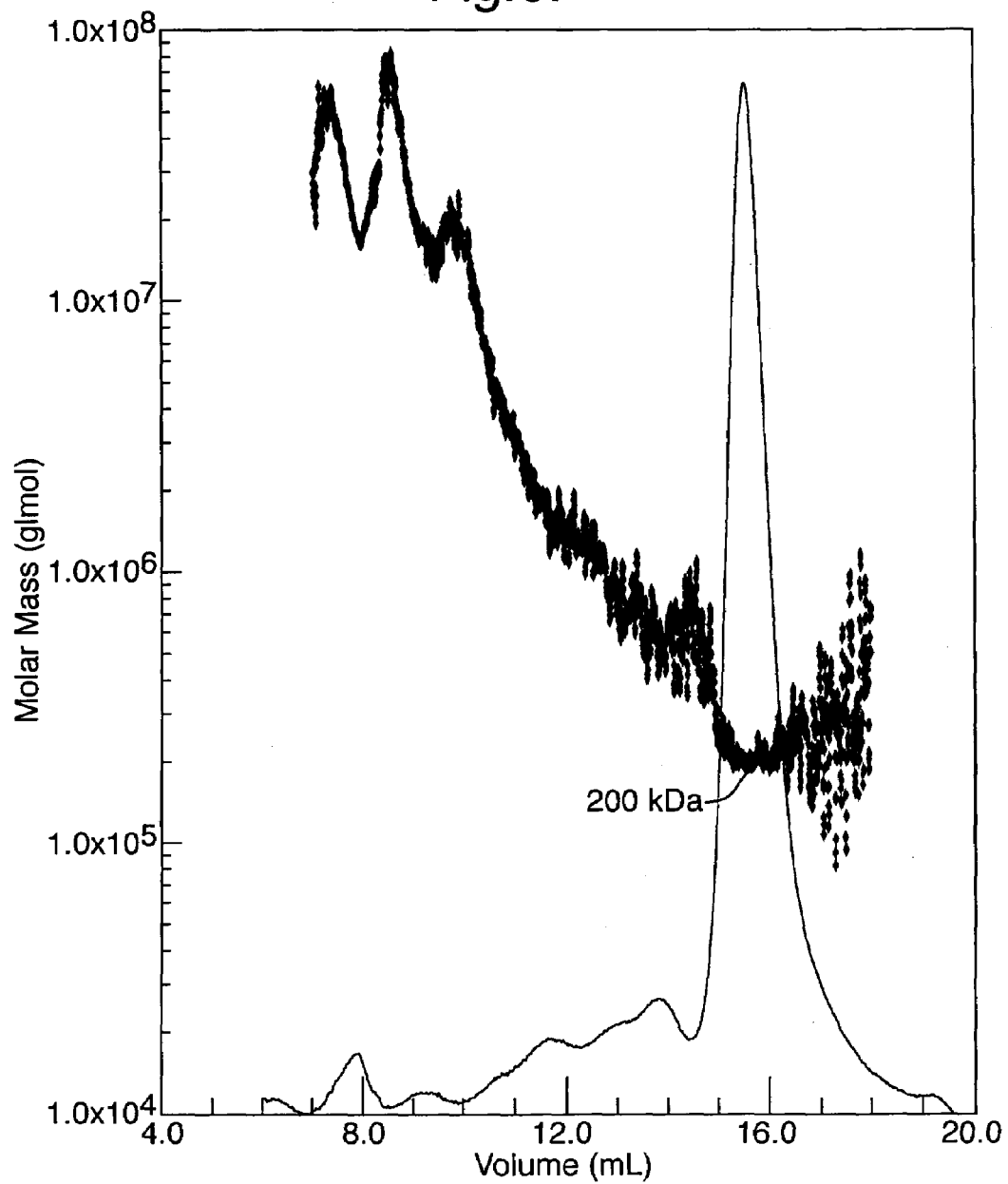
FIG. 6—Light scatter analysis to confirm the molecular weight of Ang-1-FD-Fc-FD and to determine whether or not the protein is a homogeneous species. Light scattering is a function of mass and concentration of a macromolecule. To determine molecular weight, the protein sample was injected onto a gel filtration column and the effluent is monitored with an on line light scattering detector and a refractive index and/or a UV detector. The on line refractive index detector or UV detector serve to measure protein concentration. Astra 4.7 Software (Wyatt Technology Corporation, Santa Barbara, Calif.) is used to calculate the protein concentration. The molecular weight of protein is then calculated from the angular dependence of light scattering. The molecular weight of the dimeric protein appears to be approximately 200 kD and presence of a single peak implies that the protein solution is homogenous.

Molecular Weight Analysis: The predicted molecular weight for Ang-1-FD-Fc-FD protein was determined using the MacVector Program (Kodak, Scientific Imaging Systems, New Haven, Conn.) The monomeric form (with respect to the Fc) has a predicted weight of 76,349. In addition, there are three predicted N-linked glycosylation sites, approximately 2500 MW/site, that could potentially increase the molecular weight of the monomeric protein to 83,849. Due to the interaction between the Fc components of adjacent molecules, the protein actually exists as a dimer with a predicted molecular weight, including possible N-linked glycosylation, of 167,698. Subsequent SDS PAGE analyses of COS cell-derived protein described infra confirmed these approximate molecular weights, with a band running at about 210 kD under non-reducing conditions and a band running at about 85 kD under reducing conditions (FIG. 5). Light scatter analysis was performed to further confirm the molecular weight and, more importantly, determine whether or not the protein was a homogeneous species. Light scattering is a function of mass and concentration of a macromolecule. To determine molecular weight, the protein sample was injected onto a gel filtration column and the effluent was monitored with an on line light scattering detector and a refractive index and/or a UV detector. The light scattering detector is a MiniDawn laser light scattering detector was from Wyatt Technology Corporation (Santa Barbara, CA). This instrument measures static light at three different angles. The on line refractive index detector or UV detector serve to measure protein concentration. Astra 4.7 Software (Wyatt Technology Corporation, Santa Barbara, Calif.) was used to, calculate the protein concentration based on either dn/dc (dn=change of refractive index; dc=concentration) or the extinction coefficient of the protein. The molecular weight of protein is then calculated from the angular dependence of light scattering. FIG. 6 shows the results of this analysis using COS cell-derived protein. The molecular weight of the dimeric protein appears to be approximately 200 kD and presence of a single peak implies that the protein solution is, in fact, homogenous.

Expression Level in COS Cells: COS cell supernatant containing recombinant Ang-1-FD-Fc-FD protein was generated by transiently transfecting COS cells with the Ang1-FD-Fc-FD DNA construct described supra. All transfections were performed using standard techniques known in the art. The COS cell supernatant was analyzed using Biacore technology (Pharmacia, Inc.) to quantitate the amount of Ang-1-FD-Fc-FD protein present in the supernatant. This analysis resulted in an RU value of 765, which is equivalent to 0.9 mg of recombinant protein/liter of COS cell supernatant. These values represent very high levels of expression.

Purification of COS Supernatants: Because the Ang-1-FD-Fc-FD protein contains an Fc domain, purification is relatively simple and straight forward using standard Protein A column chromatography (Pharmacia, Inc.) followed by standard size exclusion chromatography (Pharmacia, Inc.). In fact, the relative ease of purification of the Ang-1-FD-Fc-FD protein gives it a distinct advantage over the parent protein, angiopoietin-1, from which it is derived, and the mutant version of angiopoietin-1 called Ang1* that consists of the N-terminal of angiopoietin-2 fused to the coiled-coil domain and fibrinogen domain of angiopoietin-1 and that has a Cys to Ser mutation at amino acid 245. (See PCT International Application entitled "Modified TIE-2 Receptor Ligands," published as WO 98/05779 on 12 Feb. 1998 in the name of Regeneron Pharmaceuticals, Inc., especially FIG. 27, which is hereby incorporated by reference).

Both angiopoietin-1 and Ang1* require extensive, expensive and labor-intensive purification schemes that result in relatively poor yields of recombinant protein. The need for cost-effective, simple purification schemes for biologicals intended for clinical use can not be over-emphasized.

The COS cell supernatant was purified as described supra and yielded approximately 1 mg of purified Ang-1-FD-Fc-FD protein that was used in the studies described infra to further characterize the protein.

N-terminal sequencing of COS cell-derived Ang-1-FD-Fc-FD protein: Purified Ang-1-FD-Fc-FD protein was subjected to standard N-terminal sequence analysis to determine if any truncated species of the protein were being generated. This was of concern because the mutant molecule, Ang1*, has a history of containing between 10–20% N-terminally truncated species. The analysis revealed only one N-terminal sequence, Arg-Asp-X-Ala-Asp, wherein X is Cys (SEQ ID NO: 17). This sequence can be found at amino acids 16–20 of FIG. 3A (SEQ ID NO: 6), and immediately follows the protein's signal sequence corresponding to amino acids 1–15 FIG. 3A (SEQ ID NO: 6).

Receptor binding analysis of COS cell-derived Ang-1-FD-Fc-FD: Previous studies have determined that the fibrinogen domain (FD) of the angiopoietin molecules is necessary for ligand/receptor interaction. Furthermore, in order for high affinity binding to the Tie-2 receptor to occur, native angiopoietin-1, angiopoietin-2, and the mutant Ang1* must form at least tetrameric, and possibly higher order, multimers. To determine whether the COS cell-derived Ang-1-FD-Fc-FD protein, which is tetrameric with respect to the FD domain, could bind to Tie-2 with high affinity, standard Biacore analysis was performed. Briefly, Tie-2-Fc receptor body protein, which is a fusion protein comprising the ectodomain of Tie-2 fused to the Fc domain of human IgG1, was immobilized on a Biacore chip. Ang-1-FD-Fc-FD-containing solution was passed over the chip and binding between Tie-2 ectodomain and Ang-1-FD-Fc-FD was allowed to occur. The binding step was followed by a 0.5 M NaCl high salt wash. The high salt wash was not able to disrupt the interaction between the Ang-1-FD-Fc-FD protein and the Tie-2 receptor ectodomain, implying that there is a strong interaction between the mutant ligand and receptor. This result is consistent with earlier Biacore results in which both Ang-1-FD-Fc-FD parent molecule, angiopoietin-1 and the mutant Ang1* molecule, have been shown to interact strongly with the Tie-2-Fc receptor and that this interaction is not disrupted by high salt. In contrast, several mutant molecules derived from the parent angiopoietin-1 molecule are readily dissociated from the Tie-2-Fc receptor when treated with high salt. The mutant molecules, designated Ang-1/FD (a monomer with respect to the FD), Ang-1/FD-Fc (also a monomer with respect to the FD, but which is able to form a dimer due to the presence of the Fc domain), and Ang-1/C/FD (a monomer with respect to the FD, but which also contains the coiled-coil domain of angiopoietin-1), do not exist in multimeric forms sufficient for high affinity binding to the Tie-2 receptor.

Example 3

Characterization of COS Cell-Derived Ang-2-FD-Fc-FD Protein

Figure 7:
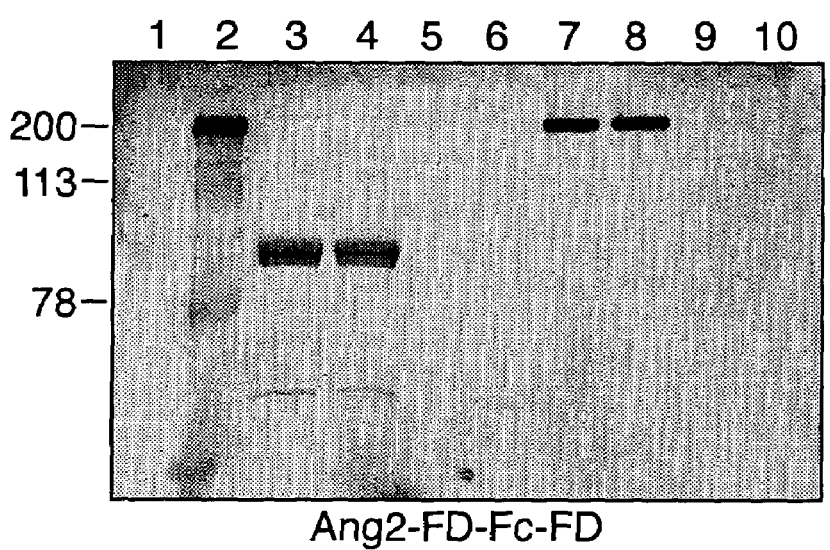
FIG. 7—Molecular Weight Analysis of Ang-2-FD-Fc-FD. SDS PAGE analyses showing a band running at about 200 kD under non-reducing conditions (lanes 7 and 8) and a band running at about 88 kD under reducing conditions (lanes 3 and 4).
Figure 8:
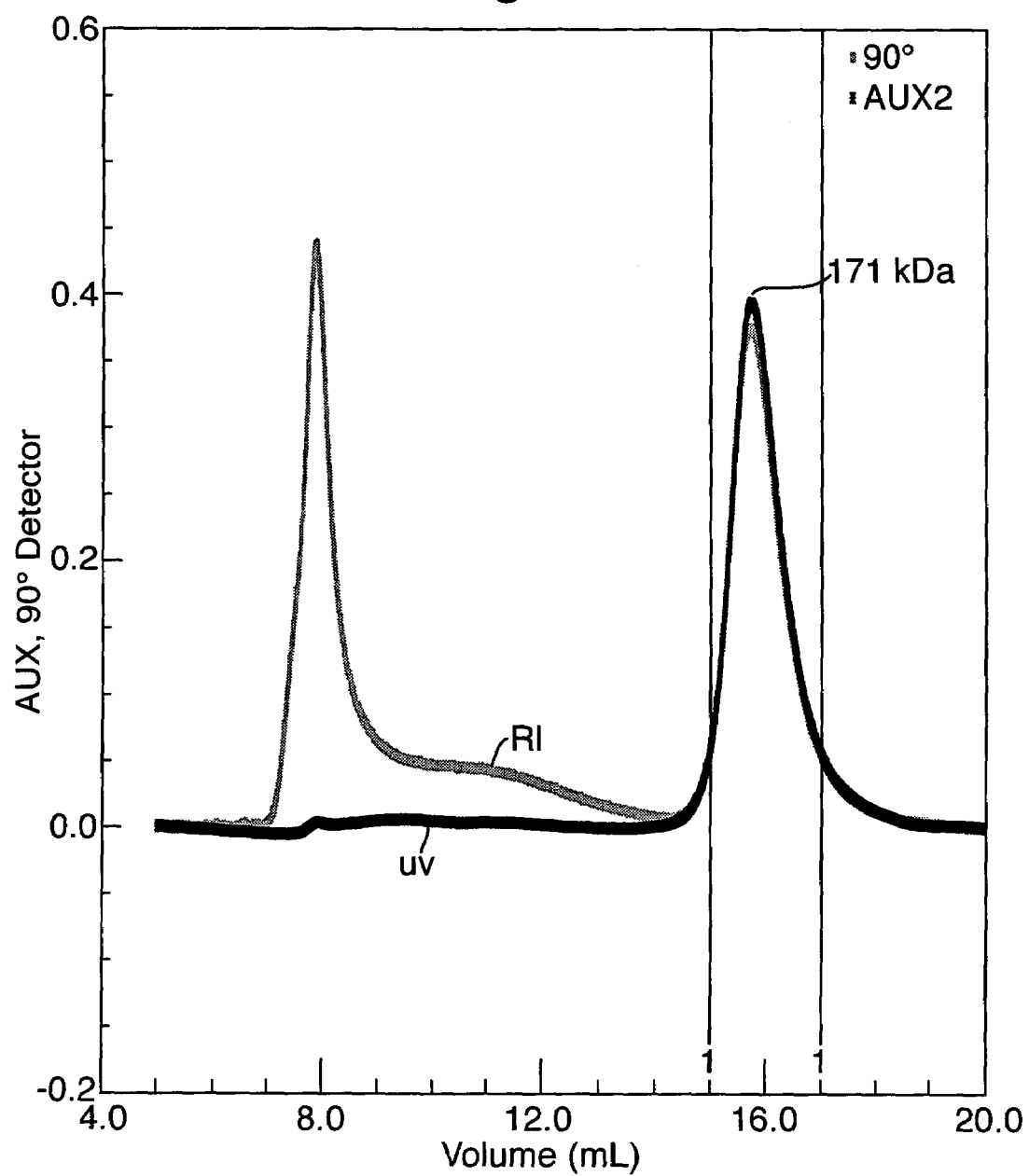
FIG. 8—Light scatter analysis to confirm the molecular weight of Ang-2-FD-Fc-FD and to determine whether or not the protein is a homogeneous species. Light scattering is a function of mass and concentration of a macromolecule. To determine molecular weight, the protein sample was injected onto a gel filtration column and the effluent is monitored with an on line light scattering detector and a refractive index and/or a UV detector. The on line refractive index detector or UV detector serve to measure protein concentration. Astra 4.7 Software (Wyatt Technology Corporation, Santa Barbara, Calif.) is used to calculate the protein concentration. The molecular weight of protein is then calculated from the angular dependence of light scattering. The molecular weight of the dimeric protein appears to be approximately 171 kD and presence of a single peak implies that the protein solution is homogenous.

Molecular Weight Analysis: As described for Ang-1-FD-Fc-FD supra, the predicted molecular weight for Ang-2-FD-Fc-FD protein was determined using the MacVector Program (Kodak, Scientific Imaging Systems, New Haven, Conn.) The monomeric form of Ang-2-FD-Fc-FD has a predicted weight of 76,052, with three predicted N-linked glycosylation sites that could potentially increase the molecular weight of the monomeric protein to 83,552. Like Ang-1-FD-Fc-FD, the protein exists as a dimer with a predicted molecular weight, including possible N-linked glycosylation, of 167,104. SDS PAGE analyses of COS cell-derived protein confirmed these approximate molecular weights, with a band running at about 200 kD under non-reducing conditions and a band running at about 88 kD under reducing conditions (FIG. 7). Light scatter analysis confirmed the molecular weight (171 kD) and revealed that the Ang-2-FD-Fc-FD protein, like Ang-1-FD-Fc-FD, exists as a homogeneous species (FIG. 8).

Expression Level in COS Cells: COS cell supernatant containing recombinant Ang-2-FD-Fc-FD protein was generated by transiently transfecting COS cells with the Ang-2-FD-Fc-FD DNA construct described supra. The COS cell supernatant was analyzed by Biacore to quantitate the amount of Ang-2-FD-Fc-FD protein present in the supernatant. This analysis resulted in an RU value of 606, which is equivalent to 0.7 mg of recombinant protein/liter of COS cell supernatant. These values represent relatively high levels of expression.

Purification of COS Supernatants: As with Ang-1-FD-Fc-FD, Ang-2-FD-Fc-FD protein contains an Fc domain, so purification is relatively simple and straight forward using standard Protein A column chromatography followed by standard size exclusion chromatography. The COS cell supernatant was purified as described for Ang-1-FD-Fc-FD supra and yielded approximately 2 mg of purified Ang-2-FD-Fc-FD protein that was used in the studies described infra to further characterize this protein.

N-terminal sequencing: Purified COS cell-derived Ang-2-FD-Fc-FD protein was subjected to standard N-terminal sequence analysis to determine if any truncated species of the protein were being generated. The analysis revealed only one N-terminal sequence, Arg-Asp-X-Ala-Glu, wherein X is Cys (SEQ ID NO: 18). This sequence can be found at amino acids 16–20 of FIG. 4A (SEQ ID NO: 8), and immediately follows the protein's signal sequence corresponding to amino acids 1–15 of FIG. 4A (SEQ ID NO: 8).

Receptor binding analysis of COS cell-derived protein: To determine whether the COS cell-derived Ang-2-FD-Fc-FD protein could bind to the Tie-2 receptor, standard Biacore analysis was performed as described for Ang-1-FD-Fc-FD supra. As with Ang-1-FD-Fc-FD, a high salt wash was not able to disrupt the interaction between the Ang-2-FD-Fc-FD protein and the Tie-2-Fc receptor, again implying that there is a strong interaction between mutant ligand and receptor.

Example 4

Effects of COS Cell-Derived Ang-1-FD-Fc-FD and Ang-2-FD-Fc-FD on Tie-2 Receptor Phosphorylation in EAhy226 Cells Because Ang-1-FD-Fc-FD is a mutant molecule derived from the agonist angiopoietin-1 and Ang-2-FD-Fc-FD is a mutant molecule derived from the antagonist angiopoietin-2, we wanted to determine whether or not these two mutant molecules would retain the activity associated with the parent molecule from which it was derived.

Assay system: All of the experiments described infra utilized the cell line EAhy926 (Edgell, C. J., et al., (1983) Proc. Natl. Acad. Sci. USA 80:3734–3737) and standard phosphorylation assays and reagents familiar to those of skill in the art.

Figure 9:
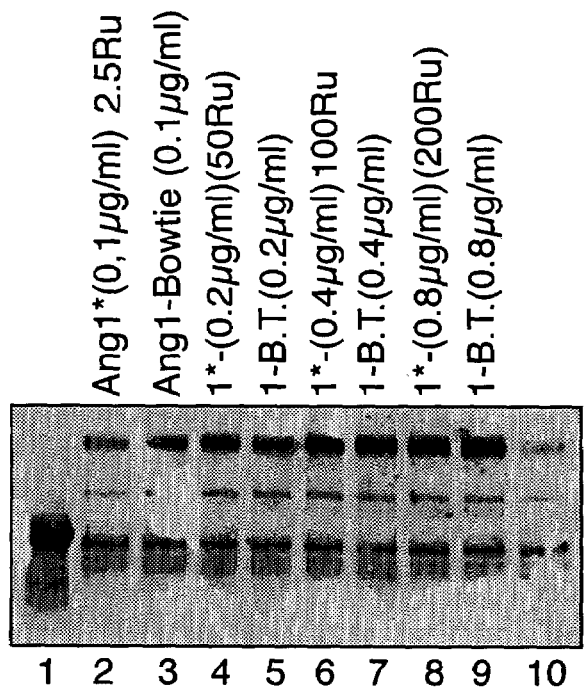
FIG. 9—Ang1*-mediated vs. Ang-1-FD-Fc-FD-mediated Tie-2 receptor phosphorylation in EAhy926 cells. A standard phosphorylation assay revealed that Ang-1-FD-Fc-FD was equivalent to Ang1* in its ability to stimulate phosphorylation of the Tie-2 receptor in EAhy926.

(A) Ang1*-mediated vs. Ang-1-FD-Fc-FD-mediated Tie-2 receptor phosphorylation in EAhy926 cells: EAhy926 cells were stimulated with either 0.1 µg/ml, 0.2 µg/ml, or 0.8 µg/ml Ang1* or Ang-1-FD-Fc-FD protein. A standard phosphorylation assay revealed that Ang-1-FD-Fc-FD was equivalent to Ang1* in its ability to stimulate phosphorylation of the Tie-2 receptor in EAhy926 cells (FIG. 9).

Figure 10:
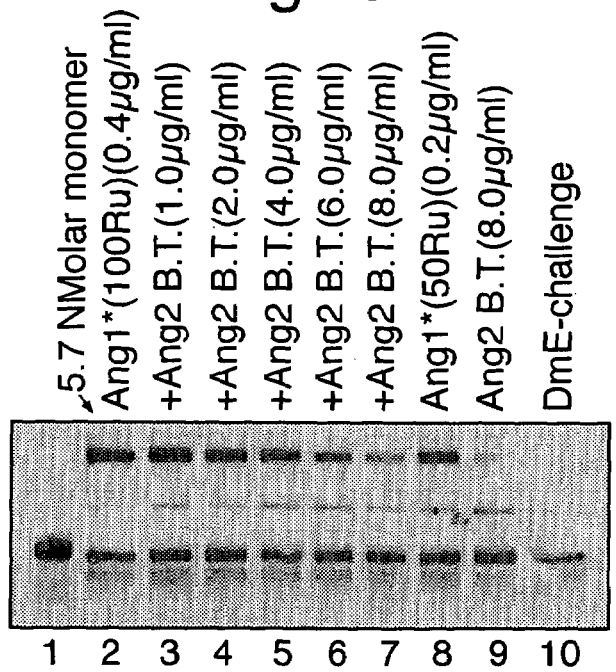
FIG. 10—Ability of Ang-2-FD-Fc-FD to block Ang1*-mediated Tie-2 receptor phosphorylation in EAhy926 cells. In a standard phosphorylation assay, Ang-2-FD-Fc-FD is able to block Ang1* stimulation of the Tie-2 receptor when it is present in at least a 10–15 fold molar excess of Ang1*.

(B) Ability of Ang-2-FD-Fc-FD to block Ang1*-mediated Tie-2 receptor phosphorylation in EAhy926 cells: EAhy926 cells were treated with 0.4 µg/ml of the Tie-2 agonist Ang1* and 1 µg/ml, 2 µg/ml, 4 µg/ml. 6 µg/ml, or 8 µg/ml of Ang-2-FD-Fc-FD. As shown in FIG. 10, Ang-2-FD-Fc-FD is able to block Ang1* stimulation of the Tie-2 receptor when it is present in at least a 10–15 fold molar excess of Ang1*.

Figure 11:
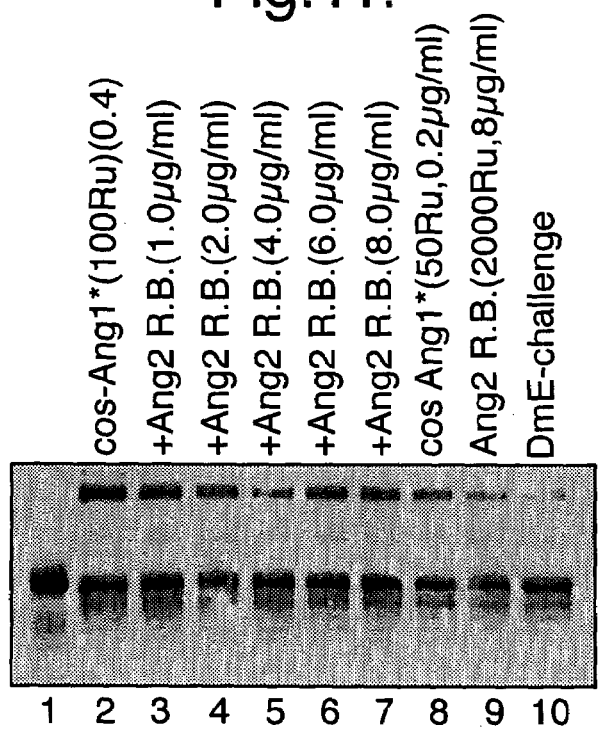
FIG. 11—Ability of angiopoietin-2 to block Ang1*-mediated Tie-2 receptor phosphorylation in EAhy926 cells. In a standard phosphorylation assay, at 20 fold molar excess, angiopoietin-2 is not able to reduce the Ang1*-mediated phosphorylation level to 50%. This result, coupled with the results described in FIG. 10 implies that Ang-2-FD-Fc-FD is a more potent inhibitor of Ang1*-mediated Tie-2 receptor phosphorylation than angiopoietin-2.

(C) Ability of angiopoietin-2 to block Ang1*-mediated Tie-2 receptor phosphorylation in EAhy926 cells: To compare the blocking effects of the naturally occurring antagonist angiopoietin-2 with that of Ang-2-FD-Fc-FD, the same experiment described in (B) supra was performed, substituting angiopoietin-2 for Ang-2-FD-Fc-FD. The results of this experiment are shown in FIG. 11. At a 20 fold molar excess, the angiopoietin-2 has not reduced the phosphorylation level to 50%. This result, coupled with the results described in (B) supra implies that Ang-2-FD-Fc-FD is a more potent inhibitor or Ang1*-mediated Tie-2 receptor phosphorylation than angiopoietin-2.

Figure 12:
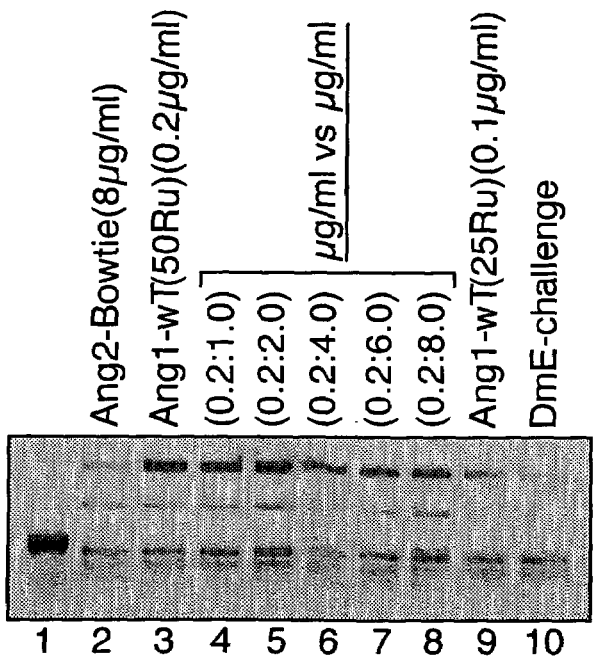
FIG. 12—Ability of Ang-2-FD-Fc-FD to block angiopoietin-1-mediated phosphorylation of the Tie-2 receptor in EAhy926 cells. In a standard phosphorylation assay, it is shown that while there is a trend toward blocking angiopoietin-1-mediated phosphorylation of the Tie-2 receptor in these cells, Ang-2-FD-Fc-FD seems to be more effective at blocking Ang1*-mediated phosphorylation of Tie-2, as shown in FIG. 10.

(D) Ability of Ang-2-FD-Fc-FD to block angiopoietin-1-mediated phosphorylation of the Tie-2 receptor in EAhy926 cells: EAhy926 cells were treated with 0.2 µg/ml of the naturally occurring Tie-2 agonist angiopoietin-1 and 1 µg/ml, 2 µg/ml, 4 µg/ml. 6 µg/ml, or 8 µg/ml of Ang-2-FD-Fc-FD. The results of this experiment, shown in FIG. 12, show that while there is a trend toward blocking angiopoietin-1-mediated phosphorylation of the Tie-2 receptor in these cells, Ang-2-FD-Fc-FD seems to be more effective at blocking Ang1*-mediated phosphorylation of Tie-2, as shown in FIG. 10 and described in (B) supra.

Figure 13:
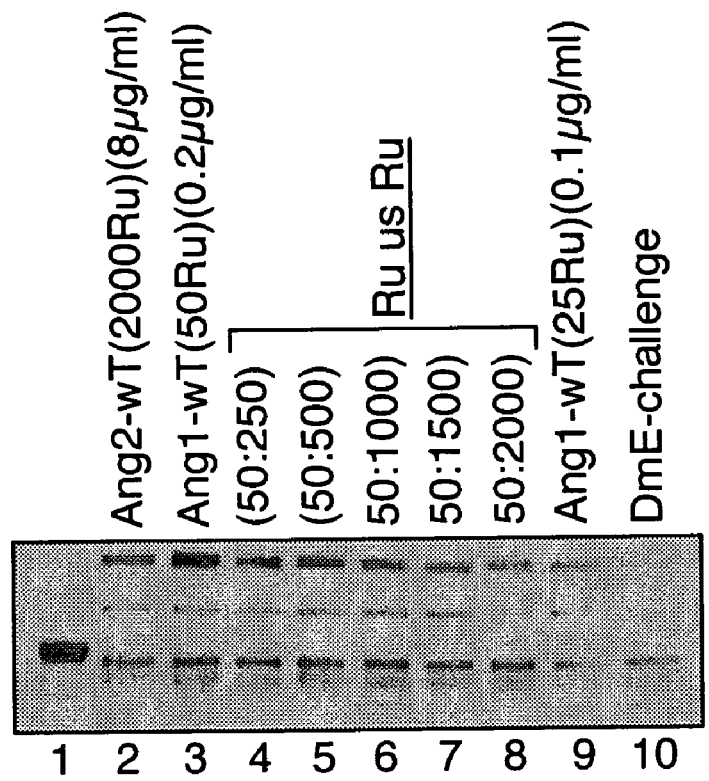
FIG. 13—Ability of angiopoietin-2 to block angiopoietin-1-mediated phosphorylation of the Tie-2 receptor in EAhy926 cells. In a standard phosphorylation assay, it is shown that there is a trend toward blocking angiopoietin-1-mediated phosphorylation of the Tie-2 receptor in these cells, but, like Ang-2-FD-Fc-FD, angiopoietin-2 seems to be more effective at blocking Ang1*-mediated phosphorylation of Tie-2, as shown in FIG. 11.

(E) Ability of angiopoietin-2 to block angiopoietin-1-mediated phosphorylation of the Tie-2 receptor in EAhy926 cells: EAhy926 cells were treated with 0.2 μg/ml of the angiopoietin-1 and 1 μg/ml, 2 μg/ml, 4 μg/ml, 6 μg/ml, or 8 μg/ml of angiopoietin-2. The results of this experiment, shown in FIG. 13, show that there is a trend toward blocking angiopoietin-1-mediated phosphorylation of the Tie-2 receptor in these cells, but, like Ang-2-FD-Fc-FD, angiopoietin-2 seems to be more effective at blocking Ang1*-mediated phosphorylation of Tie-2, as shown FIG. 11 and described in (C) supra.

Example 5

Construction of Ang-1-FD-Fc-FD CHO Cell Expression Vector pRG763/Ang-1-FD-Fc-FD The pRG763/Ang-1-FD-Fc-FD CHO cell expression vector was constructed by isolating from the plasmid pCDNA3.1/Ang1-FD-Fc-FD a 2115 base pair EcoRI-NotI fragment containing Ang1-FD-Fc-FD and ligating this fragment into pRG763 vector digested with EcoRI and NotI. A large scale (2 L) culture of *E. coli* DH10B cells carrying the pRG763/Ang-1-FD-Fc-FD plasmid was grown overnight in TB+ampicillin and the plasmid DNA was extracted using a Promega Wizard Plus Maxiprep kit; following the manufacturer's protocol. The concentration of the purified plasmid DNA was determined in a UV spectrophotometer and fluorometer. The plasmid DNA was verified by digestion of aliquots with NcoI and HincII restriction enzymes. All restriction enzyme digest fragments corresponded to the predicted sizes in a 1% agarose gel.

Example 6

Expression of Ang-1-FD-Fc-FD in CHO Cells

Forty 15 cm petri plates were seeded with CHO-K1/E1A cells at a density of $4 \times 10^6$ cells/plate. Plating media was Gibco Ham's F-12 w/10% Hyclone Fetal Bovine Serum (FBS)+penicillin/streptomycin and supplemented with glutamine. The following day each plate was transfected with 6 μg of pRG763/Ang-1-FD-Fc-FD using Gibco Optimem and Gibco Lipofectamine in 12 ml volume, following the manufacturer's protocol. Four hours after adding the transfection mix to the cells 12 ml/plate of Optimem w/10% FBS was added. Plates were incubated at 37° C. in a 5% $CO_2$ incubator overnight. The following day the media was removed from each plate and 25 ml expression media (Gibco CHO-S-SFM II w/glutamine+1 mM sodium butyrate) was added. The plates were incubated at 37° C. for 3 days. After 3 days of incubation the media was aspirated from each plate and centrifuged at 400 rpm in a swinging bucket rotor to pellet cells. The supernatant was decanted into sterile 1 L bottles and purified as described infra.

Example 7

Construction of Ang-2-FD-Fc-FD CHO Cell Expression Vector pRG763/Ang-2-FD-Fc-FD The plasmid pRG763/Ang-2-FD-Fc-FD was constructed by isolating from the plasmid pCDNA3.1/Ang-2-FD-Fc-FD a 2097 base pair EcoRI-NotI fragment containing Ang-2-FD-Fc-FD and ligating this fragment into the pRG763 vector digested with EcoRI and NotI. A large scale (1 L) culture of *E. coli* DH10B cells carrying the pRG763/Ang-2-FD-Fc-FD plasmid was grown overnight in TB+ampicillin and the plasmid DNA was extracted using a Promega Wizard Plus Maxiprep kit, following the manufacturer's protocol. The concentration of the purified plasmid DNA was determined in a UV spectrophotometer and fluorometer. The plasmid DNA was also verified by digestion of plasmid DNA with NcoI and Ppu10I restriction enzymes. All restriction enzyme digest fragments corresponded to the predicted sizes in a 1% agarose gel.

Example 8

Expression of Ang-2-FD-Fc-FD in CHO Cells

Forty 15 cm petri plates were seeded with CHO-K1/E1A cells at a density of $4 \times 10^6$ cells/plate. Plating media was Gibco Ham's F-12 w/10% Hyclone Fetal Bovine Serum (FBS)+penicillin/streptomycin and supplemented with glutamine. The following day each plate was transfected with 6 μg of pRG763/Ang-2-FD-Fc-FD using Gibco Optimem and Gibco Lipofectamine in 12 ml volume, following the manufacturer's protocol. Four hours after adding the transfection mix to the cells 12 ml/plate of Optimem w/10% FBS was added. Plates were incubated at 37° C. in a 5% $CO_2$ incubator overnight. The following day the media was removed from each plate and 25 ml expression media (Gibco CHO-S-SFM II w/glutamine+1 mM sodium butyrate) was added. The plates were incubated at 37° C. for 3 days. After 3 days of incubation the media was aspirated from each plate and centrifuged at 400 rpm in a swinging bucket rotor to pellet cells. The supernatant was decanted into sterile 1 L bottles purified as described infra.

Example 9

Characterization of Stable CHO Clone-Derived Ang-1-FD-Fc-FD Protein

Molecular Weight Analysis: The predicted molecular weight for stable CHO clone-derived Ang-1-FD-Fc-FD protein was determined using the MacVector Program (Kodak, Scientific Imaging Systems, New Haven, Conn.) The monomeric form (with respect to the Fc) has a predicted weight of 76,349. In addition, there are three predicted N-linked glycosylation sites, approximately 2500 MW/site, that could potentially increase the molecular weight of the monomeric protein to 83,849. Due to the interaction between the Fc components of adjacent molecules, the protein actually exists as a dimer with a predicted molecular weight, including possible N-linked glycosylation, of 167,698. Subsequent SDS PAGE analyses confirmed these approximate molecular weights, with a band running at about 210 kD under non-reducing conditions and a band running at about 85 kD under reducing conditions. Light scatter analysis was performed to further confirm the molecular weight and, more importantly, determine whether or not the protein was a homogeneous species. Light scattering is a function of mass and concentration of a macromolecule. To determine molecular weight, the protein sample was injected onto a gel filtration column and the effluent was monitored with an on line light scattering detector and a refractive index and/or a UV detector. The light scattering detector is a MiniDawn laser light scattering detector was from Wyatt Technology Corporation (Santa Barbara, Calif.). This instrument measures static light at three different angles. The on line refractive index detector or UV detector serve to measure protein concentration. Astra 4.7 Software (Wyatt Technology Corporation, Santa Barbara, Calif.) was used to calculate the protein concentration based on either dn/dc (dn change of refractive index; dc=concentration) or the extinction coefficient of the protein. The molecular weight of protein is then calculated from the angular dependence of light scattering. The results of this analysis show that the dimeric-protein appears to be approximately 173.9 kD and the presence of a single peak implies that the protein solution is homogenous.

Expression level of Ang-1-FD-Fc-FD in stable CHO clones: CHO cell supernatant containing recombinant Ang-1-FD-Fc-FD protein was generated by stably transfecting CHO cells with the Ang-1-FD-Fc-FD DNA construct described supra. The CHO cell supernatant was analyzed by standard ELISA using an anti-human IgG antibody as a capture antibody and an anti-human IgG antibody conjugated to alkaline phosphatase as a reporter antibody to quantitate the amount of Ang-1-FD-Fc-FD protein present in the supernatant. This analysis revealed expression levels of 2–3 pg/cell/day.

Purification of Ang-1-FD-Fc-FD protein derived from stable CHO clone supernatants: Because the Ang-1-FD-Fc-FD protein contains an Fc domain, purification is relatively simple and straight forward using standard Protein A column chromatography (Pharmacia, Inc.) followed by standard size exclusion chromatography (Pharmacia, Inc.). The CHO cell supernatant was purified as described supra and the purified ANG-1-FD-Fc-FD protein was used in the studies described infra to further characterize the protein.

N-terminal sequencing of stable CHO clone-derived Ang-1-FD-Fc-FD protein: Purified Ang-1-FD-Fc-FD protein was subjected to standard N-terminal sequence A analysis to determine if any truncated species of the protein were being generated. The analysis revealed only one N-terminal sequence, Arg-Asp-X-Ala-Asp, wherein X is Cys (SEQ ID NO: 17). This sequence can be found at amino acids 16–20 of FIG. 3A (SEQ ID NO: 6) and immediately follows the protein's signal sequence corresponding to amino acids 1–15 FIG. 3A (SEQ ID NO: 6).

Example 10

Characterization of Stable CHO Clone-Derived Ang-2-FD-Fc-FD Protein

Molecular Weight Analysis: As described for stable CHO clone-derived Ang-1-FD-Fc-FD supra, the predicted molecular weight for stable CHO clone-derived Ang-2-FD-Fc-FD protein was determined using the MacVector Program (Kodak, Scientific Imaging Systems, New Haven, Conn.). The monomeric form of Ang-2-FD-Fc-FD has a predicted weight of 76,052, with three predicted N-linked glycosylation sites that could potentially increase the molecular weight of the monomeric protein to 83,552. Like Ang-1-FD-Fc-FD, the protein exists as a dimer with a predicted molecular weight, including possible N-linked glycosylation, of 167,104. SDS PAGE analyses confirmed these approximate molecular weights, with a band running at about 200 kD under non-reducing conditions and a band running at about 85 kD under reducing conditions. Light scatter analysis confirmed the molecular weight (176.6 kD) and revealed that the stable CHO clone-derived Ang-2-FD-Fc-FD protein, like stable CHO clone-derived Ang-1-FD-Fc-FD, exists as a homogeneous species.

Expression level of Ang-2-FD-Fc-FD derived from stable CHO clones: CHO cell supernatant containing recombinant Ang-2-FD-Fc-FD protein was generated by stably transfecting CHO cells with the Ang-2-FD-Fc-FD DNA construct described supra. The CHO cell supernatant was analyzed by standard ELISA using an anti-human IgG antibody as a capture antibody and an anti-human IgG antibody conjugated to alkaline phosphatase as a reporter antibody to quantitate the amount of Ang-2-FD-Fc-FD protein present in the supernatant. This analysis revealed expression levels of approximately 1–2 pg/cell/day.

Purification of stable CHO clone-derived Ang-2-FD-Fc-FD from cell supernatants: As with Ang-1-FD-Fc-FD, Ang-2-FD-Fc-FD protein contains an Fc domain, so purification is relatively simple and straight forward using standard Protein A column chromatography followed by standard size exclusion chromatography. The CHO cell supernatant was purified as described for stable CHO clone-derived Ang-1-FD-Fc-FD supra and was used in the studies described infra to further characterize this protein.

N-terminal sequencing of stable CHO clone-derived Ang-2-FD-Fc-FD protein: Purified stable CHO clone-derived Ang-2-FD-Fc-FD protein was subjected to standard N-terminal sequence analysis to determine if any truncated species of the protein were being generated. The analysis revealed only one N-terminal sequence, Asp-X-Ala-Glu-Val, wherein X is Cys (SEQ ID NO: 19). This sequence can be found at amino acids 17–21 of FIG. 4A (SEQ ID NO: 8), and immediately follows the protein's signal sequence corresponding to amino acids 1–15 of FIG. 4A (SEQ ID NO: 8).

Example 11

Effects of Stable CHO Clone-Derived Ang-1-FD-Fc-FD and Ang-2-FD-Fc-FD on Tie-2 Receptor Phosphorylation in EAhy926 Cells Assay system: All of the experiments described infra utilized the cell line EAhy926 (Edgell, C. J., et al., (1983) Proc. Natl. Acad. Sci. USA 80:3734–3737) and standard phosphorylation assays and reagents familiar to those of skill in the art.

Figure 17:
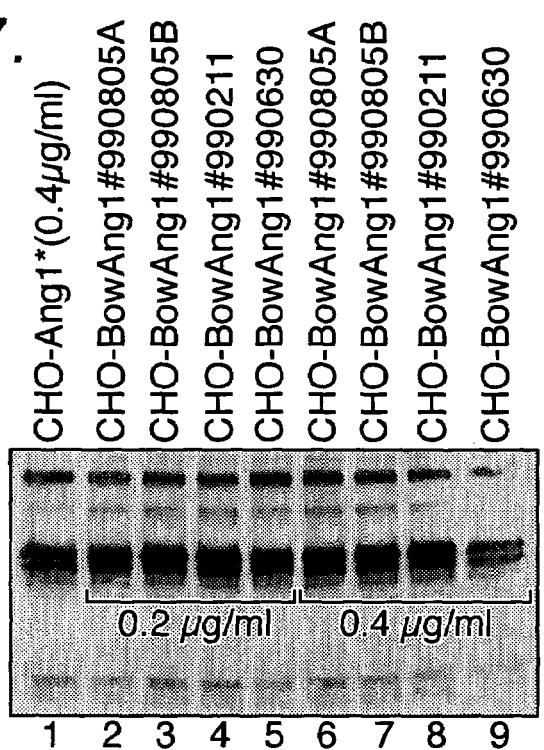
FIG. 17—Ang1*-mediated vs. stable CHO clone-derived Ang-1-FD-Fc-FD-mediated Tie-2 receptor phosphorylation in EAhy926 cells. EAhy926 cells were stimulated with 0.4 μg/ml Ang1* or 0.2 μg/ml or 0.4 μg/ml stable CHO clone-derived Ang-1-FD-Fc-FD protein. A standard phosphorylation assay revealed that stable CHO clone-derived Ang-1-FD-Fc-FD was equivalent to Ang1* in its ability to stimulate phosphorylation of the Tie-2 receptor in EAhy926 cells.

(A) Ang1*-mediated vs. stable CHO clone-derived Ang-1-FD-Fc-FD-mediated Tie-2 receptor phosphorylation in EAhy926 cells: EAhy926 cells were stimulated with 0.4 µg/ml Ang1* or 0.2 µg/ml or 0.4 µg/ml stable CHO clone-derived Ang-1-FD-Fc-FD protein. A standard phosphorylation assay revealed that or stable CHO clone-derived Ang-1-FD-Fc-FD was equivalent to Ang1* in its ability to stimulate phosphorylation of the Tie-2 receptor in EAhy926 cells (FIG. 17).

Figure 18:
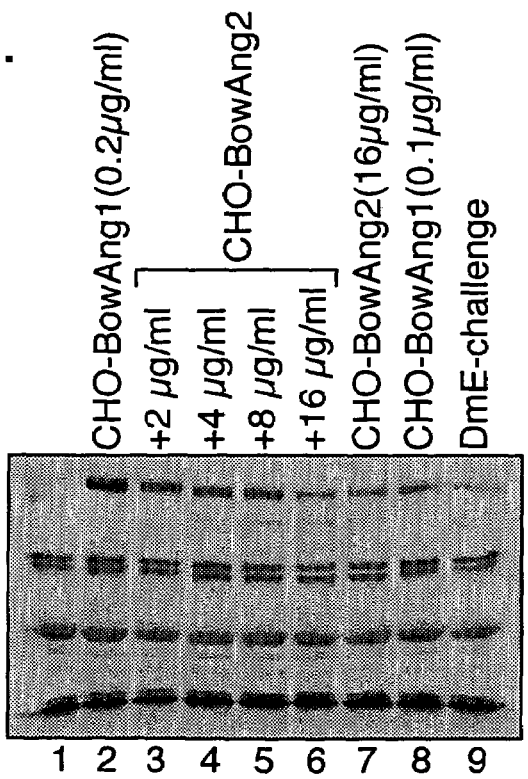
FIG. 18—Ability of stable CHO clone-derived Ang-2-FD-Fc-FD to block stable CHO clone-derived Ang-1-FD-Fc-FD-mediated Tie-2 receptor phosphorylation in EAhy926 cells. EAhy926 cells were treated with 0.2 μg/ml of the Tie-2 agonist Ang-1-FD-Fc-FD and 2 μg/ml, 4 μg/ml, 8 μg/ml or 16 μg/ml of stable CHO clone-derived Ang-2-FD-Fc-FD. Ang-2-FD-Fc-FD is able to block or stable CHO clone-derived Ang-1-FD-Fc-FD stimulation of the Tie-2 receptor when it is present in at least a 40 fold molar excess of stable CHO clone-derived Ang-1-FD-Fc-FD.

(B) Ability of stable CHO clone-derived Ang-2-FD-Fc-FD to block stable CHO clone-derived Ang-1-FD-Fc-FD-mediated Tie-2 receptor phosphorylation in EAhy926 cells: EAhy926 cells were treated with 0.2 µg/ml of the Tie-2 agonist Ang-1-FD-Fc-FD and 2 µg/ml, 4 µg/ml, 8 µg/ml or 16 µg/ml of stable CHO clone-derived Ang-2-FD-Fc-FD. As shown in FIG. 18, Ang-2-FD-Fc-FD is able to block stable CHO clone-derived Ang-1-FD-Fc-FD stimulation of the Tie-2 receptor when it is present in at least a 40 fold molar excess of stable CHO clone-derived Ang-1-FD-Fc-FD.

Ephrin Ligands:

In previous experiments (Davis et al., 1994, Science, 266:816–819; Gale et al., 1996, Neuron 17:9–19, Gale and Yancopoulos, 1997, Cell Tissue Research 290:227–241), soluble, unclustered Ephrin-B1-Fc and Ephrin-B2-Fc, which dimerize at their respective Fc domains and therefore are dimeric with respect to either the Ephrin-B1 or Ephrin-B2 ectodomain, failed to induce EphB2 receptor phosphorylation. However, when either molecule was multimerized by pre-clustering with an anti-Fc antibody, they became potent agonists for the EphB2 receptor, as judged by tyrosine phosphorylation of the EphB2 receptor in a COS cell reporter assay. Because multimerization, of both Ephrin-B1 and Ephrin-B2 appears to be necessary for induction of receptor phosphorylation, we theorized that a molecule that contained tandem repeats of either Ephrin-B1 or Ephrin-B2 ectodomains fused to an Fc domain, which would be dimeric, with respect to the Fc domain but which would be tetrameric with respect to Ephrin ectodomains, might be sufficiently clustered to induce receptor phosphorylation. To test this hypothesis, the following, DNA constructs were constructed, recombinant proteins produced, and reporter assays performed.

Construction of Tandem Ephrin Ectodomain/Fc Domain Nucleic Acid Molecules.

All of the following nucleic acid molecules were constructed by standard recombinant DNA techniques (See e.g., Molecular Cloning, A Laboratory Manual (Sambrook, et al., Cold Spring Harbor Laboratory, Cold Spring Harbor, N.Y.), Current Protocols in Molecular Biology (Eds. Ausubel, et al., Greene Publ. Assoc., Wiley-Interscience, NY), sequence-verified by standard techniques using an ABI 373A DNA sequencer and Taq Dideoxy Terminator Cycle Sequencing Kit (Applied Biosystems, Inc., Foster City, Calif.), and subcloned into either the mammalian expression pJFE14 (Ephrin-B1-Ephrin-B1-Fc) or pMT21 (Ephrin-B2-Ephrin-B2-Fc), each with a Kozak sequence (Kozak, M., 1987, Nucleic Acids Res. 15:8125–8148) at the 5' end to promote protein translation. The bridging sequences described infra were introduced to provide convenient restriction sites and to give flexibility to the junctions between the domains, but there is no indication that there is a very critical nature to these bridging sequences (though varying the length of the linker in some of these constructs led to some variation in the amount of protein produced).

Example 12

Construction of Ephrin-B1-Ephrin-B1-Fc and Ephrin-B2-Ephrin-B2-Fc Nucleic Acid Molecules (A) Ephrin-B1-Ephrin-B1-Fc: The Ephrin-B1-Ephrin-B1-Fc DNA molecule consists of the coding sequence of the ectodomain of Ephrin-B1 (Davis et al., ibid.), which corresponds to nucleotides 1–711 of FIG. 14A–FIG. 14B (SEQ ID NO: 9), followed by a bridging sequence consisting of the amino acids Gly-Pro-Gly (nucleotides 712–720 of FIG. 14B [SEQ ID NO: 9), followed by a second copy of the ectodomain of Ephrin-B1 (corresponding to nucleotides 721–1344 of FIG. 14B–FIG. 14D [SEQ ID NO: 9]), except that in this copy of the Ephrin-B1 ectodomain the signal sequence has been removed. This second copy is followed by a second Gly-Pro-Gly amino acid bridge (nucleotides 1345–1353 of FIG. 14D [SEQ ID NO: 9]), followed by the coding sequence for the Fc portion of human IgG1 (nucleotides 1354–2049 of FIG. 14D–FIG. 14E [SEQ ID NO: 9]).

(B) Ephrin-B2-Ephrin-B2-Fc: The Ephrin-B2-Ephrin-B2-Fc DNA molecule consists of the coding sequence of the ectodomain of Ephrin-B2 (Bergemann et al., 1995, Mol. Cell Biol. 15:4821–4929), which corresponds to nucleotides 1–675 of FIG. 15A–FIG. 15B (SEQ ID NO: 11), followed by a bridging sequence consisting of the amino acids Gly-Pro-Gly (nucleotides 676–684 of FIG. 15B [SEQ ID NO: 11), followed by a second copy of the ectodomain of Ephrin-B2 (corresponding to nucleotides 685–1270 of FIG. 15B–FIG. 15D [SEQ ID NO: 11]), except that in this copy the signal sequence has been removed. This second copy is followed by a second Gly-Pro-Gly amino acid bridge (nucleotides 1270–1278 of FIG. 15D [SEQ ID NO: 11]), followed by the coding sequence for the Fc portion of human IgG1 (nucleotides 1279–1977 of FIG. 15D–FIG. 15E [SEQ ID NO: 11]).

As with the angiopoietin nucleic acid molecules described supra, the bridging sequences were introduced to provide convenient restriction sites and to give flexibility to the junctions between the domains.

Example 13

Expression of Tandem Ephrin Recombinant Proteins in COS Cells

COS cells were transiently transfected with either the Ephrin-B1-Ephrin-B1-Fc or Ephrin-B2-Ephrin-B2-Fc nucleic acid molecules described supra using standard transfection techniques known in the art. Two days subsequent to transfection, the growth medium (DMEM supplemented with 100 U/ml penicillin, 100 μg/ml streptomycin, 2 mM glutamine, and 10%, calf serum) was aspirated and replaced with serum-free medium (DMEM supplemented with 100 U/ml penicillin, 100 μg/ml streptomycin, 2 mM glutamine). Cell were grown for an additional three days and then the serum-free medium containing the recombinant proteins was collected. Recombinant protein concentration was determined by performing dot blots and comparing the signal obtained to a standard curve. Once approximate protein concentrations were determined, the Ephrin-B1-Ephrin-B1-Fc and Ephrin-B2-Ephrin-B2-Fc recombinant proteins were used in the cell reporter assays described infra.

Example 14

Characterization of the COS Cell-Derived Tandem Ephrin Ectodomain/Fc Domain Recombinant Proteins Reporter Assay: COS cells, which endogenously express the Eph family receptor EphB2 (Gale et al., 1996; Neuron 17:9–19), were used in reporter assays to evaluate the ability of Ephrin-B1-Ephrin-B1-Fc and Ephrin-B2-Ephrin-B2-Fc to induce receptor phosphorylation. The assays were performed as previously described (Davis et al., ibid.; Gale et al., ibid.). Briefly, COS cells were grown to 80–90% confluency in standard growth medium described supra. After growth, the medium was aspirated, and replaced with serum-free medium (described supra) for 1–2 hours prior to treatment with either Ephrin-B1-Ephrin-B1-Fc or Ephrin-B2-Ephrin B2-Fc recombinant protein. The cells were stimulated with 500 ng/ml Ephrin-B1-Ephrin-B1-Fc or Ephrin-B2-Ephrin-B2-Fc for 30 minutes at 37° C., with or without affinity purified human IgG1 Fc-specific goat anti-human antibody (Jackson Immunoresearch, West Grove, Pa.) at a final concentration of 17 μg/ml. This antibody is capable of clustering the Fc tagged fusion. Subsequent to treatment, the COS cells were harvested and cell lysates were prepared as described in Davis, et al. and Gale, et al., supra. The EphB2 receptor protein was immunoprecipitated from the cell lysates using an anti-EphB2 antisera (Henkemeyer et al., 1994, Oncogene 9:1001–1014). Immunoprecipitates were resolved by standard SDS PAGE and transferred to PVDF membranes (Millipore) for western blot analysis. The membranes were probed with either anti-phosphotyrosine antibody 4G10 (Upstate Biotechnology Institute, Lake Placid, N.Y.) or anti-EphB2 antibodies (Henkemeyer, et al., ibid.) to determine the extent of EphB2 phosphorylation and the relative quantities of EphB2 in the experimental conditions described supra.

Figure 16:
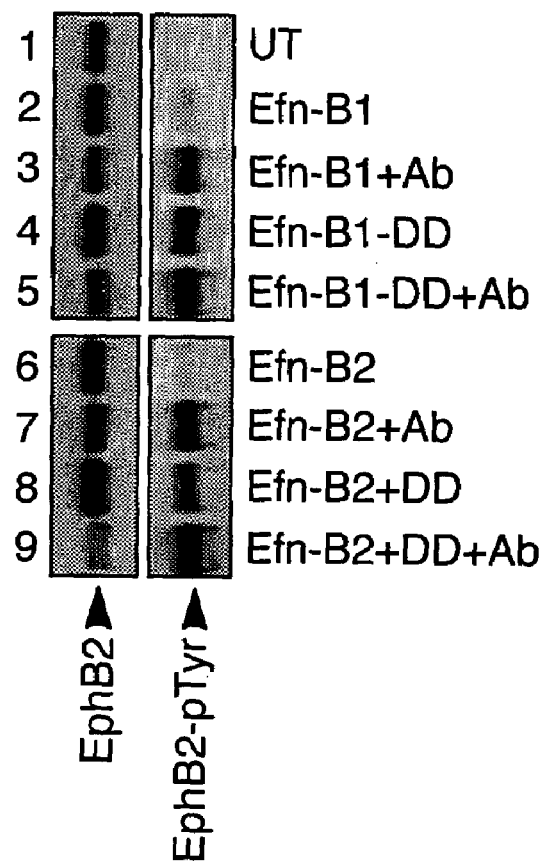
FIG. 16—Comparison of Ephrin-B1-Fc, Ephrin-B1-Ephrin-B1-Fc, Ephrin-B2-Fc and Ephrin-B2-Ephrin-B2-Fc in standard EphB2 phosphorylation assays. COS cells were serum-starved and then left untreated (UT), lane 1, or were treated with unclustered and clustered Ephrin-B1-Fc (Efn-B1), lanes 2 and 3. COS cells were also treated with unclustered and clustered Ephrin-B1-Ephrin-B1-Fc (Efn-B1 DD), lanes 4 and 5. In addition cells were likewise treated with unclustered and clustered Ephrin-B2-Fc (Efn-B2), lanes 6 and 7 and with unclustered and clustered Ephrin-B2-Ephrin-B2-Fc (Efn-B2 DD), lanes 8 and 9. The extent of EphB2 phosphorylation was assessed by anti-phosphotyrosine western blotting (upper panels) and the relative amounts of EphB2 in each lane was determined by anti-EphB2 western blotting (lower panels).

Results: Both Ephrin-B1-Ephrin-B1-Fc and Ephrin-B2-Ephrin-B2-Fc were shown to be approximately as active as anti-Fc antibody-clustered Ephrin-B1-Fc in their ability to induce EphB2 receptor, phosphorylation in the COS cell reporter assay. Furthermore, if either of the proteins were further clustered with the goat anti-human Fc antibody, they became even more potent in their ability to induce EphB2 receptor phosphorylation. FIG. 16 shows the results of this phosphorylation assay.

Example 15

Construction of Ephrin-B2-Ephrin-B2-Fc CHO Expression Vector

The Ephrin-B2-Ephrin-B2-Fc DNA molecule consists of the coding sequence of the ectodomain of Ephrin-B2 (Bergemann et al., 1995, Mol. Cell Biol. 15:4821–4929), which corresponds to nucleotides 1–675 of FIG. 15A–FIG. 15B (SEQ ID NO: 11), followed by a bridging sequence consisting of the amino acids Gly-Pro-Gly (nucleotides 676–684 of FIG. 15B [SEQ ID NO: 11]), followed by a second copy of the ectodomain of Ephrin-B2 (corresponding to nucleotides 685–1270 of FIG. 15B–FIG. 15D [SEQ ID NO: 11]), except that in this copy the signal sequence has been removed. This second copy is followed by a second Gly-Pro-Gly amino acid bridge (nucleotides 1270–1278 of FIG. 15D [SEQ ID NO: 11]), followed by the coding sequence for the Fc portion of human IgG1 (nucleotides 1279–1977 of FIG. 15D–FIG. 15E [SEQ ID NO: 11]). This molecule was subcloned into the HindIII and NotI polylinker sites in the expression vector pRG763 and was designated pRG763-m(Ephrin-B2)2-Fc. As with the angiopoietin nucleic acid molecules described supra, the bridging sequences were introduced to provide convenient restriction sites and to give flexibility to the junctions between the domains.

Example 16

Expression of Ephrin-B2-Ephrin-B2-Fc in CHO-K1 (E1A) Cells

Forty 15 cm petri plates were seeded with CHO-K1/E1A cells at a density of $4 \times 10^6$ cells/plate. Plating media was Gibco Ham's F-12 w/10% Hyclone Fetal Bovine Serum (FBS)+penicillin/streptomycin and supplemented with glutamine. The following day each plate was transfected with 6 μg of pRG763-m(Ephrin-B2)2-Fc using Gibco Optimem and Gibco Lipofectamine in 12 ml volume, following the manufacturer's protocol. Four hours after adding the transfection mix to the cells 12 ml/plate of Optimem w/10% FBS was added. Plates were incubated at 37° C. in a 5% $CO_2$ incubator overnight. The following day the media was removed from each plate and 25 ml expression media (Gibco CHO-S-SFM II w/glutamine+1 mM sodium butyrate) was added. The plates were incubated at 37° C. for 3 days. After 3 days of incubation the media was aspirated from each plate and centrifuged at 400 rpm in a swinging bucket rotor to pellet cells. The supernatant was decanted into sterile 1 L bottles and purified as described supra.

What is claimed is:

1. An isolated nucleic acid molecule encoding a fusion polypeptide, wherein the fusion polypeptide consists of a first subunit comprising a receptor binding domain of angiopoietin-1, fused to an N-terminal end of a multimerizing component, and the multimerizing component fused at its C-terminal end to a second receptor binding domain of angiopoietin-1, wherein the multimerizing component is an immunoglobulin derived domain selected from the group consisting of the Fc domain of IgG and the heavy chain of IgG.

2. A fusion polypeptide encoded by the isolated nucleic acid molecule of claim 1.

3. The fusion polypeptide of claim 2, wherein the fusion polypeptide is multimerized.

4. A composition comprising the multimerized fusion polypeptide of claim 3.

5. The composition of claim 4, wherein the multimer is a dimer formed by interaction between the multimerizing components of two adjacent fusion polypeptide molecules.

6. The composition of claim 4 wherein the multimer is tetrameric with respect to Ang1-fibrinogen domain (FD).

7. A vector which comprises the isolated nucleic acid molecule of claim 1.

8. An expression vector comprising an isolated nucleic acid molecule of claim 1, wherein the nucleic acid molecule is operatively linked to an expression control sequence.

9. A host-vector system for the production of a fusion polypeptide which comprises the expression vector of claim 8, in a suitable host cell.

10. The host-vector system of claim 9, wherein the suitable host cell is a bacterial cell, yeast cell, insect cell or mammalian cell.

11. The host-vector system of claim 10, wherein the suitable host cell is *E. coli*.

12. The host-vector system of claim 10, wherein the suitable host cell is a COS cell.

13. The host-vector system of claim 10, wherein the suitable host cell is a CHO cell.

14. A method of producing a fusion polypeptide which comprises growing cells of the host-vector system of claim 10, under conditions permitting production of the fusion polypeptide and recovering the polypeptide so produced.

15. The nucleic acid molecule of claim 1, comprising SEQ ID NO:5.

* * * * *

SEQUENCE LISTING

```
<160> NUMBER OF SEQ ID NOS: 19

<210> SEQ ID NO 1
<211> LENGTH: 2058
<212> TYPE: DNA
<213> ORGANISM: Homo sapiens
<220> FEATURE:
<221> NAME/KEY: CDS
<222> LOCATION: (1)...(2055)

<400> SEQUENCE: 1 atg tct gca ctt ctg atc cta gct ctt gtt gga gct gca gtt gct aga        48
Met Ser Ala Leu Leu Ile Leu Ala Leu Val Gly Ala Ala Val Ala Arg
 1               5                  10                  15 gac tgt gca gat gta tat caa gct ggt ttt aat aaa agt gga atc tac        96
Asp Cys Ala Asp Val Tyr Gln Ala Gly Phe Asn Lys Ser Gly Ile Tyr
                20                  25                  30 act att tat att aat aat atg cca gaa ccc aaa aag gtg ttt tgc aat       144
Thr Ile Tyr Ile Asn Asn Met Pro Glu Pro Lys Lys Val Phe Cys Asn
            35                  40                  45 atg gat gtc aat ggg gga ggt tgg act gta ata caa cat cgt gaa gat       192
Met Asp Val Asn Gly Gly Gly Trp Thr Val Ile Gln His Arg Glu Asp
        50                  55                  60 gga agt cta gat ttc caa aga ggc tgg aag gaa tat aaa atg ggt ttt       240
Gly Ser Leu Asp Phe Gln Arg Gly Trp Lys Glu Tyr Lys Met Gly Phe
    65                  70                  75                  80 gga aat ccc tcc ggt gaa tat tgg ctg ggg aat gag ttt att ttt gcc       288
```

```
                                            -continued

Gly Asn Pro Ser Gly Glu Tyr Trp Leu Gly Asn Glu Phe Ile Phe Ala
                85                  90                  95 att acc agt cag agg cag tac atg cta aga att gag tta atg gac tgg      336
Ile Thr Ser Gln Arg Gln Tyr Met Leu Arg Ile Glu Leu Met Asp Trp
            100                 105                 110 gaa ggg aac cga gcc tat tca cag tat gac aga ttc cac ata gga aat      384
Glu Gly Asn Arg Ala Tyr Ser Gln Tyr Asp Arg Phe His Ile Gly Asn
        115                 120                 125 gaa aag caa aac tat agg ttg tat tta aaa ggt cac act ggg aca gca      432
Glu Lys Gln Asn Tyr Arg Leu Tyr Leu Lys Gly His Thr Gly Thr Ala
    130                 135                 140 gga aaa cag agc agc ctg atc tta cac ggt gct gat ttc agc act aaa      480
Gly Lys Gln Ser Ser Leu Ile Leu His Gly Ala Asp Phe Ser Thr Lys
145                 150                 155                 160 gat gct gat aat gac aac tgt atg tgc aaa tgt gcc ctc atg tta aca      528
Asp Ala Asp Asn Asp Asn Cys Met Cys Lys Cys Ala Leu Met Leu Thr
                165                 170                 175 gga gga tgg tgg ttt gat gct tgt ggc ccc tcc aat cta aat gga atg      576
Gly Gly Trp Trp Phe Asp Ala Cys Gly Pro Ser Asn Leu Asn Gly Met
            180                 185                 190 ttc tat act gcg gga caa aac cat gga aaa ctg aat ggg ata aag tgg      624
Phe Tyr Thr Ala Gly Gln Asn His Gly Lys Leu Asn Gly Ile Lys Trp
        195                 200                 205 cac tac ttc aaa ggg ccc agt tac tcc tta cgt tcc aca act atg atg      672
His Tyr Phe Lys Gly Pro Ser Tyr Ser Leu Arg Ser Thr Thr Met Met
    210                 215                 220 att cga cct tta gat ttt ggc ccc gcg cct ttt aga gac tgt gca gat      720
Ile Arg Pro Leu Asp Phe Gly Pro Ala Pro Phe Arg Asp Cys Ala Asp
225                 230                 235                 240 gta tat caa gct ggt ttt aat aaa agt gga atc tac act att tat att      768
Val Tyr Gln Ala Gly Phe Asn Lys Ser Gly Ile Tyr Thr Ile Tyr Ile
                245                 250                 255 aat aat atg cca gaa ccc aaa aag gtg ttt tgc aat atg gat gtc aat      816
Asn Asn Met Pro Glu Pro Lys Lys Val Phe Cys Asn Met Asp Val Asn
            260                 265                 270 ggg gga ggt tgg act gta ata caa cat cgt gaa gat gga agt cta gat      864
Gly Gly Gly Trp Thr Val Ile Gln His Arg Glu Asp Gly Ser Leu Asp
        275                 280                 285 ttc caa aga ggc tgg aag gaa tat aaa atg ggt ttt gga aat ccc tcc      912
Phe Gln Arg Gly Trp Lys Glu Tyr Lys Met Gly Phe Gly Asn Pro Ser
    290                 295                 300 ggt gaa tat tgg ctg ggg aat gag ttt att ttt gcc att acc agt cag      960
Gly Glu Tyr Trp Leu Gly Asn Glu Phe Ile Phe Ala Ile Thr Ser Gln
305                 310                 315                 320 agg cag tac atg cta aga att gag tta atg gac tgg gaa ggg aac cga     1008
Arg Gln Tyr Met Leu Arg Ile Glu Leu Met Asp Trp Glu Gly Asn Arg
                325                 330                 335 gcc tat tca cag tat gac aga ttc cac ata gga aat gaa aag caa aac     1056
Ala Tyr Ser Gln Tyr Asp Arg Phe His Ile Gly Asn Glu Lys Gln Asn
            340                 345                 350 tat agg ttg tat tta aaa ggt cac act ggg aca gca gga aaa cag agc     1104
Tyr Arg Leu Tyr Leu Lys Gly His Thr Gly Thr Ala Gly Lys Gln Ser
        355                 360                 365 agc ctg atc tta cac ggt gct gat ttc agc act aaa gat gct gat aat     1152
Ser Leu Ile Leu His Gly Ala Asp Phe Ser Thr Lys Asp Ala Asp Asn
    370                 375                 380 gac aac tgt atg tgc aaa tgt gcc ctc atg tta aca gga gga tgg tgg     1200
Asp Asn Cys Met Cys Lys Cys Ala Leu Met Leu Thr Gly Gly Trp Trp
385                 390                 395                 400
```

-continued

```
ttt gat gct tgt ggc ccc tcc aat cta aat gga atg ttc tat act gcg      1248
Phe Asp Ala Cys Gly Pro Ser Asn Leu Asn Gly Met Phe Tyr Thr Ala
                405                 410                 415 gga caa aac cat gga aaa ctg aat ggg ata aag tgg cac tac ttc aaa      1296
Gly Gln Asn His Gly Lys Leu Asn Gly Ile Lys Trp His Tyr Phe Lys
        420                 425                 430 ggg ccc agt tac tcc tta cgt tcc aca act atg atg att cga cct tta      1344
Gly Pro Ser Tyr Ser Leu Arg Ser Thr Thr Met Met Ile Arg Pro Leu
    435                 440                 445 gat ttt gga ccg ggc gag ccc aaa tct tgt gac aaa act cac aca tgc      1392
Asp Phe Gly Pro Gly Glu Pro Lys Ser Cys Asp Lys Thr His Thr Cys
450                 455                 460 cca ccg tgc cca gca cct gaa ctc ctg ggg gga cca tca gtc ttc ctc      1440
Pro Pro Cys Pro Ala Pro Glu Leu Leu Gly Gly Pro Ser Val Phe Leu
465                 470                 475                 480 ttc ccc cca aaa ccc aag gac acc ctc atg atc tcc cgg acc cct gag      1488
Phe Pro Pro Lys Pro Lys Asp Thr Leu Met Ile Ser Arg Thr Pro Glu
            485                 490                 495 gtc aca tgc gtg gtg gtg gac gtg agc cac gaa gac cct gag gtc aag      1536
Val Thr Cys Val Val Val Asp Val Ser His Glu Asp Pro Glu Val Lys
        500                 505                 510 ttc aac tgg tac gtg gac ggc gtg gag gtg cat aat gcc aag aca aag      1584
Phe Asn Trp Tyr Val Asp Gly Val Glu Val His Asn Ala Lys Thr Lys
    515                 520                 525 ccg cgg gag gag cag tac aac agc acg tac cgt gtg gtc agc gtc ctc      1632
Pro Arg Glu Glu Gln Tyr Asn Ser Thr Tyr Arg Val Val Ser Val Leu
530                 535                 540 acc gtc ctg cac cag gac tgg ctg aat ggc aag gag tac aag tgc aag      1680
Thr Val Leu His Gln Asp Trp Leu Asn Gly Lys Glu Tyr Lys Cys Lys
545                 550                 555                 560 gtc tcc aac aaa gcc ctc cca gcc ccc atc gag aaa acc atc tcc aaa      1728
Val Ser Asn Lys Ala Leu Pro Ala Pro Ile Glu Lys Thr Ile Ser Lys
            565                 570                 575 gcc aaa ggg cag ccc cga gaa cca cag gtg tac acc ctg ccc cca tcc      1776
Ala Lys Gly Gln Pro Arg Glu Pro Gln Val Tyr Thr Leu Pro Pro Ser
        580                 585                 590 cgg gat gag ctg acc aag aac cag gtc agc ctg acc tgc ctg gtc aaa      1824
Arg Asp Glu Leu Thr Lys Asn Gln Val Ser Leu Thr Cys Leu Val Lys
    595                 600                 605 ggc ttc tat ccc agc gac atc gcc gtg gag tgg gag agc aat ggg cag      1872
Gly Phe Tyr Pro Ser Asp Ile Ala Val Glu Trp Glu Ser Asn Gly Gln
610                 615                 620 ccg gag aac aac tac aag acc acg cct ccc gtg ctg gac tcc gac ggc      1920
Pro Glu Asn Asn Tyr Lys Thr Thr Pro Pro Val Leu Asp Ser Asp Gly
625                 630                 635                 640 tcc ttc ttc ctc tac agc aag ctc acc gtg gac aag agc agg tgg cag      1968
Ser Phe Phe Leu Tyr Ser Lys Leu Thr Val Asp Lys Ser Arg Trp Gln
            645                 650                 655 cag ggg aac gtc ttc tca tgc tcc gtg atg cat gag gct ctg cac aac      2016
Gln Gly Asn Val Phe Ser Cys Ser Val Met His Glu Ala Leu His Asn
        660                 665                 670 cac tac acg cag aag agc ctc tcc ctg tct ccg ggt aaa tga              2058
His Tyr Thr Gln Lys Ser Leu Ser Leu Ser Pro Gly Lys
    675                 680                 685
```

<210> SEQ ID NO 2
<211> LENGTH: 685
<212> TYPE: PRT
<213> ORGANISM: Homo sapiens

<400> SEQUENCE: 2

```
Met Ser Ala Leu Leu Ile Leu Ala Leu Val Gly Ala Ala Val Ala Arg
 1               5                  10                  15

Asp Cys Ala Asp Val Tyr Gln Ala Gly Phe Asn Lys Ser Gly Ile Tyr
             20                  25                  30

Thr Ile Tyr Ile Asn Asn Met Pro Glu Pro Lys Lys Val Phe Cys Asn
             35                  40                  45

Met Asp Val Asn Gly Gly Gly Trp Thr Val Ile Gln His Arg Glu Asp
 50                  55                  60

Gly Ser Leu Asp Phe Gln Arg Gly Trp Lys Glu Tyr Lys Met Gly Phe
 65                  70                  75                  80

Gly Asn Pro Ser Gly Glu Tyr Trp Leu Gly Asn Glu Phe Ile Phe Ala
             85                  90                  95

Ile Thr Ser Gln Arg Gln Tyr Met Leu Arg Ile Glu Leu Met Asp Trp
            100                 105                 110

Glu Gly Asn Arg Ala Tyr Ser Gln Tyr Asp Arg Phe His Ile Gly Asn
            115                 120                 125

Glu Lys Gln Asn Tyr Arg Leu Tyr Leu Lys Gly His Thr Gly Thr Ala
130                 135                 140

Gly Lys Gln Ser Ser Leu Ile Leu His Gly Ala Asp Phe Ser Thr Lys
145                 150                 155                 160

Asp Ala Asp Asn Asp Asn Cys Met Cys Lys Cys Ala Leu Met Leu Thr
            165                 170                 175

Gly Gly Trp Trp Phe Asp Ala Cys Gly Pro Ser Asn Leu Asn Gly Met
            180                 185                 190

Phe Tyr Thr Ala Gly Gln Asn His Gly Lys Leu Asn Gly Ile Lys Trp
            195                 200                 205

His Tyr Phe Lys Gly Pro Ser Tyr Ser Leu Arg Ser Thr Thr Met Met
            210                 215                 220

Ile Arg Pro Leu Asp Phe Gly Pro Ala Pro Phe Arg Asp Cys Ala Asp
225                 230                 235                 240

Val Tyr Gln Ala Gly Phe Asn Lys Ser Gly Ile Tyr Thr Ile Tyr Ile
            245                 250                 255

Asn Asn Met Pro Glu Pro Lys Lys Val Phe Cys Asn Met Asp Val Asn
            260                 265                 270

Gly Gly Gly Trp Thr Val Ile Gln His Arg Glu Asp Gly Ser Leu Asp
            275                 280                 285

Phe Gln Arg Gly Trp Lys Glu Tyr Lys Met Gly Phe Gly Asn Pro Ser
            290                 295                 300

Gly Glu Tyr Trp Leu Gly Asn Glu Phe Ile Phe Ala Ile Thr Ser Gln
305                 310                 315                 320

Arg Gln Tyr Met Leu Arg Ile Glu Leu Met Asp Trp Glu Gly Asn Arg
            325                 330                 335

Ala Tyr Ser Gln Tyr Asp Arg Phe His Ile Gly Asn Glu Lys Gln Asn
            340                 345                 350

Tyr Arg Leu Tyr Leu Lys Gly His Thr Gly Thr Ala Gly Lys Gln Ser
            355                 360                 365

Ser Leu Ile Leu His Gly Ala Asp Phe Ser Thr Lys Asp Ala Asp Asn
370                 375                 380

Asp Asn Cys Met Cys Lys Cys Ala Leu Met Leu Thr Gly Gly Trp Trp
385                 390                 395                 400

Phe Asp Ala Cys Gly Pro Ser Asn Leu Asn Gly Met Phe Tyr Thr Ala
            405                 410                 415
```

-continued

```
Gly Gln Asn His Gly Lys Leu Asn Gly Ile Lys Trp His Tyr Phe Lys
            420                 425                 430
Gly Pro Ser Tyr Ser Leu Arg Ser Thr Thr Met Met Ile Arg Pro Leu
            435                 440                 445
Asp Phe Gly Pro Gly Glu Pro Lys Ser Cys Asp Lys Thr His Thr Cys
            450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                485                 490                 495
Val Thr Cys Val Val Val Asp Val Ser His Glu Asp Pro Glu Val Lys
            500                 505                 510
Phe Asn Trp Tyr Val Asp Gly Val Glu Val His Asn Ala Lys Thr Lys
            515                 520                 525
Pro Arg Glu Glu Gln Tyr Asn Ser Thr Tyr Arg Val Val Ser Val Leu
            530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                565                 570                 575
Ala Lys Gly Gln Pro Arg Glu Pro Gln Val Tyr Thr Leu Pro Pro Ser
            580                 585                 590
Arg Asp Glu Leu Thr Lys Asn Gln Val Ser Leu Thr Cys Leu Val Lys
            595                 600                 605
Gly Phe Tyr Pro Ser Asp Ile Ala Val Glu Trp Glu Ser Asn Gly Gln
            610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
            675                 680                 685

<210> SEQ ID NO 3
<211> LENGTH: 2061
<212> TYPE: DNA
<213> ORGANISM: Homo sapiens
<220> FEATURE:
<221> NAME/KEY: CDS
<222> LOCATION: (1)...(2058)

<400> SEQUENCE: 3 atg tct gca ctt ctg atc cta gct ctt gtt gga gct gca gtt gct aga    48
Met Ser Ala Leu Leu Ile Leu Ala Leu Val Gly Ala Ala Val Ala Arg
 1               5                  10                  15 gac tgt gct gaa gta ttc aaa tca gga cac acc aca aat ggc atc tac    96
Asp Cys Ala Glu Val Phe Lys Ser Gly His Thr Thr Asn Gly Ile Tyr
                20                  25                  30 acg tta aca ttc cct aat tct aca gaa gag atc aag gcc tac tgt gac   144
Thr Leu Thr Phe Pro Asn Ser Thr Glu Glu Ile Lys Ala Tyr Cys Asp
            35                  40                  45 atg gaa gct gga gga ggc ggg tgg aca att att cag cga cgt gag gat   192
Met Glu Ala Gly Gly Gly Gly Trp Thr Ile Ile Gln Arg Arg Glu Asp
        50                  55                  60 ggc agc gtt gat ttt cag agg act tgg aaa gaa tat aaa gtg gga ttt   240
```

```
Gly Ser Val Asp Phe Gln Arg Thr Trp Lys Glu Tyr Lys Val Gly Phe
 65                  70                  75                  80 ggt aac cct tca gga gaa tat tgg ctg gga aat gag ttt gtt tcg caa      288
Gly Asn Pro Ser Gly Glu Tyr Trp Leu Gly Asn Glu Phe Val Ser Gln
                 85                  90                  95 ctg act aat cag caa cgc tat gtg ctt aaa ata cac ctt aaa gac tgg      336
Leu Thr Asn Gln Gln Arg Tyr Val Leu Lys Ile His Leu Lys Asp Trp
            100                 105                 110 gaa ggg aat gag gct tac tca ttg tat gaa cat ttc tat ctc tca agt      384
Glu Gly Asn Glu Ala Tyr Ser Leu Tyr Glu His Phe Tyr Leu Ser Ser
        115                 120                 125 gaa gaa ctc aat tat agg att cac ctt aaa gga ctt aca ggg aca gcc      432
Glu Glu Leu Asn Tyr Arg Ile His Leu Lys Gly Leu Thr Gly Thr Ala
    130                 135                 140 ggc aaa ata agc agc atc agc caa cca gga aat gat ttt agc aca aag      480
Gly Lys Ile Ser Ser Ile Ser Gln Pro Gly Asn Asp Phe Ser Thr Lys
145                 150                 155                 160 gat gga gac aac gac aaa tgt att tgc aaa tgt tca caa atg cta aca      528
Asp Gly Asp Asn Asp Lys Cys Ile Cys Lys Cys Ser Gln Met Leu Thr
                165                 170                 175 gga ggc tgg tgg ttt gat gca tgt ggt cct tcc aac ttg aac gga atg      576
Gly Gly Trp Trp Phe Asp Ala Cys Gly Pro Ser Asn Leu Asn Gly Met
            180                 185                 190 tac tat cca cag agg cag aac aca aat aag ttc aac ggc att aaa tgg      624
Tyr Tyr Pro Gln Arg Gln Asn Thr Asn Lys Phe Asn Gly Ile Lys Trp
        195                 200                 205 tac tac tgg aaa ggc tca ggc tat tcg ctc aag gcc aca acc atg atg      672
Tyr Tyr Trp Lys Gly Ser Gly Tyr Ser Leu Lys Ala Thr Thr Met Met
    210                 215                 220 atc cga cca gca gat ttc ggg ggc ccc gcg cct ttc aga gac tgt gct      720
Ile Arg Pro Ala Asp Phe Gly Gly Pro Ala Pro Phe Arg Asp Cys Ala
225                 230                 235                 240 gaa gta ttc aaa tca gga cac acc aca aat ggc atc tac acg tta aca      768
Glu Val Phe Lys Ser Gly His Thr Thr Asn Gly Ile Tyr Thr Leu Thr
                245                 250                 255 ttc cct aat tct aca gaa gag atc aag gcc tac tgt gac atg gaa gct      816
Phe Pro Asn Ser Thr Glu Glu Ile Lys Ala Tyr Cys Asp Met Glu Ala
            260                 265                 270 gga gga ggc ggg tgg aca att att cag cga cgt gag gat ggc agc gtt      864
Gly Gly Gly Gly Trp Thr Ile Ile Gln Arg Arg Glu Asp Gly Ser Val
        275                 280                 285 gat ttt cag agg act tgg aaa gaa tat aaa gtg gga ttt ggt aac cct      912
Asp Phe Gln Arg Thr Trp Lys Glu Tyr Lys Val Gly Phe Gly Asn Pro
    290                 295                 300 tca gga gaa tat tgg ctg gga aat gag ttt gtt tcg caa ctg act aat      960
Ser Gly Glu Tyr Trp Leu Gly Asn Glu Phe Val Ser Gln Leu Thr Asn
305                 310                 315                 320 cag caa cgc tat gtg ctt aaa ata cac ctt aaa gac tgg gaa ggg aat     1008
Gln Gln Arg Tyr Val Leu Lys Ile His Leu Lys Asp Trp Glu Gly Asn
                325                 330                 335 gag gct tac tca ttg tat gaa cat ttc tat ctc tca agt gaa gaa ctc     1056
Glu Ala Tyr Ser Leu Tyr Glu His Phe Tyr Leu Ser Ser Glu Glu Leu
            340                 345                 350 aat tat agg att cac ctt aaa gga ctt aca ggg aca gcc ggc aaa ata     1104
Asn Tyr Arg Ile His Leu Lys Gly Leu Thr Gly Thr Ala Gly Lys Ile
        355                 360                 365 agc agc atc agc caa cca gga aat gat ttt agc aca aag gat gga gac     1152
Ser Ser Ile Ser Gln Pro Gly Asn Asp Phe Ser Thr Lys Asp Gly Asp
    370                 375                 380
```

-continued

```
aac gac aaa tgt att tgc aaa tgt tca caa atg cta aca gga ggc tgg    1200
Asn Asp Lys Cys Ile Cys Lys Cys Ser Gln Met Leu Thr Gly Gly Trp
385             390                 395                 400 tgg ttt gat gca tgt ggt cct tcc aac ttg aac gga atg tac tat cca    1248
Trp Phe Asp Ala Cys Gly Pro Ser Asn Leu Asn Gly Met Tyr Tyr Pro
                405                 410                 415 cag agg cag aac aca aat aag ttc aac ggc att aaa tgg tac tac tgg    1296
Gln Arg Gln Asn Thr Asn Lys Phe Asn Gly Ile Lys Trp Tyr Tyr Trp
            420                 425                 430 aaa ggc tca ggc tat tcg ctc aag gcc aca acc atg atg atc cga cca    1344
Lys Gly Ser Gly Tyr Ser Leu Lys Ala Thr Thr Met Met Ile Arg Pro
435                 440                 445 gca gat ttc gga ccg ggc gag ccc aaa tct tgt gac aaa act cac aca    1392
Ala Asp Phe Gly Pro Gly Glu Pro Lys Ser Cys Asp Lys Thr His Thr
        450                 455                 460 tgc cca ccg tgc cca gca cct gaa ctc ctg ggg gga ccg tca gtc ttc    1440
Cys Pro Pro Cys Pro Ala Pro Glu Leu Leu Gly Gly Pro Ser Val Phe
465                 470                 475                 480 ctc ttc ccc cca aaa ccc aag gac acc ctc atg atc tcc cgg acc cct    1488
Leu Phe Pro Pro Lys Pro Lys Asp Thr Leu Met Ile Ser Arg Thr Pro
                485                 490                 495 gag gtc aca tgc gtg gtg gtg gac gtg agc cac gaa gac cct gag gtc    1536
Glu Val Thr Cys Val Val Val Asp Val Ser His Glu Asp Pro Glu Val
            500                 505                 510 aag ttc aac tgg tac gtg gac ggc gtg gag gtg cat aat gcc aag aca    1584
Lys Phe Asn Trp Tyr Val Asp Gly Val Glu Val His Asn Ala Lys Thr
        515                 520                 525 aag ccg cgg gag gag cag tac aac agc acg tac cgt gtg gtc agc gtc    1632
Lys Pro Arg Glu Glu Gln Tyr Asn Ser Thr Tyr Arg Val Val Ser Val
530                 535                 540 ctc acc gtc ctg cac cag gac tgg ctg aat ggc aag gag tac aag tgc    1680
Leu Thr Val Leu His Gln Asp Trp Leu Asn Gly Lys Glu Tyr Lys Cys
545                 550                 555                 560 aag gtc tcc aac aaa gcc ctc cca gcc ccc atc gag aaa acc atc tcc    1728
Lys Val Ser Asn Lys Ala Leu Pro Ala Pro Ile Glu Lys Thr Ile Ser
                565                 570                 575 aaa gcc aaa ggg cag ccc cga gaa cca cag gtg tac acc ctg ccc cca    1776
Lys Ala Lys Gly Gln Pro Arg Glu Pro Gln Val Tyr Thr Leu Pro Pro
            580                 585                 590 tcc cgg gat gag ctg acc aag aac cag gtc agc ctg acc tgc ctg gtc    1824
Ser Arg Asp Glu Leu Thr Lys Asn Gln Val Ser Leu Thr Cys Leu Val
        595                 600                 605 aaa ggc ttc tat ccc agc gac atc gcc gtg gag tgg gag agc aat ggg    1872
Lys Gly Phe Tyr Pro Ser Asp Ile Ala Val Glu Trp Glu Ser Asn Gly
610                 615                 620 cag ccg gag aac aac tac aag acc acg cct ccc gtg ctg gac tcc gac    1920
Gln Pro Glu Asn Asn Tyr Lys Thr Thr Pro Pro Val Leu Asp Ser Asp
625                 630                 635                 640 ggc tcc ttc ttc ctc tac agc aag ctc acc gtg gac aag agc agg tgg    1968
Gly Ser Phe Phe Leu Tyr Ser Lys Leu Thr Val Asp Lys Ser Arg Trp
                645                 650                 655 cag cag ggg aac gtc ttc tca tgc tcc gtg atg cat gag gct ctg cac    2016
Gln Gln Gly Asn Val Phe Ser Cys Ser Val Met His Glu Ala Leu His
            660                 665                 670 aac cac tac acg cag aag agc ctc tcc ctg tct ccg ggt aaa            2058
Asn His Tyr Thr Gln Lys Ser Leu Ser Leu Ser Pro Gly Lys
        675                 680                 685 tga                                                                 2061
```

-continued

<210> SEQ ID NO 4
<211> LENGTH: 686
<212> TYPE: PRT
<213> ORGANISM: Homo sapiens

<400> SEQUENCE: 4

```
Met Ser Ala Leu Leu Ile Leu Ala Leu Val Gly Ala Ala Val Ala Arg
 1               5                  10                  15

Asp Cys Ala Glu Val Phe Lys Ser Gly His Thr Thr Asn Gly Ile Tyr
             20                  25                  30

Thr Leu Thr Phe Pro Asn Ser Thr Glu Glu Ile Lys Ala Tyr Cys Asp
         35                  40                  45

Met Glu Ala Gly Gly Gly Gly Trp Thr Ile Ile Gln Arg Arg Glu Asp
     50                  55                  60

Gly Ser Val Asp Phe Gln Arg Thr Trp Lys Glu Tyr Lys Val Gly Phe
 65                  70                  75                  80

Gly Asn Pro Ser Gly Glu Tyr Trp Leu Gly Asn Glu Phe Val Ser Gln
                 85                  90                  95

Leu Thr Asn Gln Gln Arg Tyr Val Leu Lys Ile His Leu Lys Asp Trp
            100                 105                 110

Glu Gly Asn Glu Ala Tyr Ser Leu Tyr Glu His Phe Tyr Leu Ser Ser
        115                 120                 125

Glu Glu Leu Asn Tyr Arg Ile His Leu Lys Gly Leu Thr Gly Thr Ala
    130                 135                 140

Gly Lys Ile Ser Ser Ile Ser Gln Pro Gly Asn Asp Phe Ser Thr Lys
145                 150                 155                 160

Asp Gly Asp Asn Asp Lys Cys Ile Cys Lys Cys Ser Gln Met Leu Thr
                165                 170                 175

Gly Gly Trp Trp Phe Asp Ala Cys Gly Pro Ser Asn Leu Asn Gly Met
            180                 185                 190

Tyr Tyr Pro Gln Arg Gln Asn Thr Asn Lys Phe Asn Gly Ile Lys Trp
        195                 200                 205

Tyr Tyr Trp Lys Gly Ser Gly Tyr Ser Leu Lys Ala Thr Thr Met Met
    210                 215                 220

Ile Arg Pro Ala Asp Phe Gly Pro Ala Pro Phe Arg Asp Cys Ala
225                 230                 235                 240

Glu Val Phe Lys Ser Gly His Thr Thr Asn Gly Ile Tyr Thr Leu Thr
                245                 250                 255

Phe Pro Asn Ser Thr Glu Glu Ile Lys Ala Tyr Cys Asp Met Glu Ala
            260                 265                 270

Gly Gly Gly Gly Trp Thr Ile Ile Gln Arg Arg Glu Asp Gly Ser Val
        275                 280                 285

Asp Phe Gln Arg Thr Trp Lys Glu Tyr Lys Val Gly Phe Gly Asn Pro
    290                 295                 300

Ser Gly Glu Tyr Trp Leu Gly Asn Glu Phe Val Ser Gln Leu Thr Asn
305                 310                 315                 320

Gln Gln Arg Tyr Val Leu Lys Ile His Leu Lys Asp Trp Glu Gly Asn
                325                 330                 335

Glu Ala Tyr Ser Leu Tyr Glu His Phe Tyr Leu Ser Ser Glu Glu Leu
            340                 345                 350

Asn Tyr Arg Ile His Leu Lys Gly Leu Thr Gly Thr Ala Gly Lys Ile
        355                 360                 365

Ser Ser Ile Ser Gln Pro Gly Asn Asp Phe Ser Thr Lys Asp Gly Asp
    370                 375                 380
```

```
Asn Asp Lys Cys Ile Cys Lys Cys Ser Gln Met Leu Thr Gly Gly Trp
385                 390                 395                 400

Trp Phe Asp Ala Cys Gly Pro Ser Asn Leu Asn Gly Met Tyr Tyr Pro
                405                 410                 415

Gln Arg Gln Asn Thr Asn Lys Phe Asn Gly Ile Lys Trp Tyr Tyr Trp
            420                 425                 430

Lys Gly Ser Gly Tyr Ser Leu Lys Ala Thr Thr Met Met Ile Arg Pro
        435                 440                 445

Ala Asp Phe Gly Pro Gly Glu Pro Lys Ser Cys Asp Lys Thr His Thr
    450                 455                 460

Cys Pro Pro Cys Pro Ala Pro Glu Leu Leu Gly Gly Pro Ser Val Phe
465                 470                 475                 480

Leu Phe Pro Pro Lys Pro Lys Asp Thr Leu Met Ile Ser Arg Thr Pro
                485                 490                 495

Glu Val Thr Cys Val Val Val Asp Val Ser His Glu Asp Pro Glu Val
            500                 505                 510

Lys Phe Asn Trp Tyr Val Asp Gly Val Glu Val His Asn Ala Lys Thr
        515                 520                 525

Lys Pro Arg Glu Glu Gln Tyr Asn Ser Thr Tyr Arg Val Val Ser Val
    530                 535                 540

Leu Thr Val Leu His Gln Asp Trp Leu Asn Gly Lys Glu Tyr Lys Cys
545                 550                 555                 560

Lys Val Ser Asn Lys Ala Leu Pro Ala Pro Ile Glu Lys Thr Ile Ser
                565                 570                 575

Lys Ala Lys Gly Gln Pro Arg Glu Pro Gln Val Tyr Thr Leu Pro Pro
            580                 585                 590

Ser Arg Asp Glu Leu Thr Lys Asn Gln Val Ser Leu Thr Cys Leu Val
        595                 600                 605

Lys Gly Phe Tyr Pro Ser Asp Ile Ala Val Glu Trp Glu Ser Asn Gly
    610                 615                 620

Gln Pro Glu Asn Asn Tyr Lys Thr Thr Pro Pro Val Leu Asp Ser Asp
625                 630                 635                 640

Gly Ser Phe Phe Leu Tyr Ser Lys Leu Thr Val Asp Lys Ser Arg Trp
                645                 650                 655

Gln Gln Gly Asn Val Phe Ser Cys Ser Val Met His Glu Ala Leu His
            660                 665                 670

Asn His Tyr Thr Gln Lys Ser Leu Ser Leu Ser Pro Gly Lys
        675                 680                 685

<210> SEQ ID NO 5
<211> LENGTH: 2067
<212> TYPE: DNA
<213> ORGANISM: Homo sapiens
<220> FEATURE:
<221> NAME/KEY: CDS
<222> LOCATION: (1)...(2064)

<400> SEQUENCE: 5 atg tct gca ctt ctg atc cta gct ctt gtt gga gct gca gtt gct aga      48
Met Ser Ala Leu Leu Ile Leu Ala Leu Val Gly Ala Ala Val Ala Arg
 1               5                  10                  15 gac tgt gca gat gta tat caa gct ggt ttt aat aaa agt gga atc tac      96
Asp Cys Ala Asp Val Tyr Gln Ala Gly Phe Asn Lys Ser Gly Ile Tyr
                20                  25                  30 act att tat att aat aat atg cca gaa ccc aaa aag gtg ttt tgc aat     144
Thr Ile Tyr Ile Asn Asn Met Pro Glu Pro Lys Lys Val Phe Cys Asn
        35                  40                  45
```

-continued

```
atg gat gtc aat ggg gga ggt tgg act gta ata caa cat cgt gaa gat      192
Met Asp Val Asn Gly Gly Gly Trp Thr Val Ile Gln His Arg Glu Asp
    50              55                  60 gga agt cta gat ttc caa aga ggc tgg aag gaa tat aaa atg ggt ttt      240
Gly Ser Leu Asp Phe Gln Arg Gly Trp Lys Glu Tyr Lys Met Gly Phe
 65              70                  75                  80 gga aat ccc tcc ggt gaa tat tgg ctg ggg aat gag ttt att ttt gcc      288
Gly Asn Pro Ser Gly Glu Tyr Trp Leu Gly Asn Glu Phe Ile Phe Ala
                 85                  90                  95 att acc agt cag agg cag tac atg cta aga att gag tta atg gac tgg      336
Ile Thr Ser Gln Arg Gln Tyr Met Leu Arg Ile Glu Leu Met Asp Trp
            100                 105                 110 gaa ggg aac cga gcc tat tca cag tat gac aga ttc cac ata gga aat      384
Glu Gly Asn Arg Ala Tyr Ser Gln Tyr Asp Arg Phe His Ile Gly Asn
        115                 120                 125 gaa aag caa aac tat agg ttg tat tta aaa ggt cac act ggg aca gca      432
Glu Lys Gln Asn Tyr Arg Leu Tyr Leu Lys Gly His Thr Gly Thr Ala
    130                 135                 140 gga aaa cag agc agc ctg atc tta cac ggt gct gat ttc agc act aaa      480
Gly Lys Gln Ser Ser Leu Ile Leu His Gly Ala Asp Phe Ser Thr Lys
145                 150                 155                 160 gat gct gat aat gac aac tgt atg tgc aaa tgt gcc ctc atg tta aca      528
Asp Ala Asp Asn Asp Asn Cys Met Cys Lys Cys Ala Leu Met Leu Thr
                165                 170                 175 gga gga tgg tgg ttt gat gct tgt ggc ccc tcc aat cta aat gga atg      576
Gly Gly Trp Trp Phe Asp Ala Cys Gly Pro Ser Asn Leu Asn Gly Met
            180                 185                 190 ttc tat act gcg gga caa aac cat gga aaa ctg aat ggg ata aag tgg      624
Phe Tyr Thr Ala Gly Gln Asn His Gly Lys Leu Asn Gly Ile Lys Trp
        195                 200                 205 cac tac ttc aaa ggg cca agt tac tcc tta cgt tcc aca act atg atg      672
His Tyr Phe Lys Gly Pro Ser Tyr Ser Leu Arg Ser Thr Thr Met Met
    210                 215                 220 att cga cct tta gat ttt ggc ccg ggc gag ccc aaa tct tgt gac aaa      720
Ile Arg Pro Leu Asp Phe Gly Pro Gly Glu Pro Lys Ser Cys Asp Lys
225                 230                 235                 240 act cac aca tgc cca ccg tgc cca gca cct gaa ctc ctg ggg gga ccg      768
Thr His Thr Cys Pro Pro Cys Pro Ala Pro Glu Leu Leu Gly Gly Pro
                245                 250                 255 tca gtc ttc ctc ttc ccc cca aaa ccc aag gac acc ctc atg atc tcc      816
Ser Val Phe Leu Phe Pro Pro Lys Pro Lys Asp Thr Leu Met Ile Ser
            260                 265                 270 cgg acc cct gag gtc aca tgc gtg gtg gtg gac gtg agc cac gaa gac      864
Arg Thr Pro Glu Val Thr Cys Val Val Val Asp Val Ser His Glu Asp
        275                 280                 285 cct gag gtc aag ttc aac tgg tac gtg gac ggc gtg gag gtg cat aat      912
Pro Glu Val Lys Phe Asn Trp Tyr Val Asp Gly Val Glu Val His Asn
    290                 295                 300 gcc aag aca aag ccg cgg gag gag cag tac aac agc acg tac cgt gtg      960
Ala Lys Thr Lys Pro Arg Glu Glu Gln Tyr Asn Ser Thr Tyr Arg Val
305                 310                 315                 320 gtc agc gtc ctc acc gtc ctg cac cag gac tgg ctg aat ggc aag gag     1008
Val Ser Val Leu Thr Val Leu His Gln Asp Trp Leu Asn Gly Lys Glu
                325                 330                 335 tac aag tgc aag gtc tcc aac aaa gcc ctc cca gcc ccc atc gag aaa     1056
Tyr Lys Cys Lys Val Ser Asn Lys Ala Leu Pro Ala Pro Ile Glu Lys
            340                 345                 350 acc atc tcc aaa gcc aaa ggg cag ccc cga gaa cca cag gtg tac acc     1104
Thr Ile Ser Lys Ala Lys Gly Gln Pro Arg Glu Pro Gln Val Tyr Thr
```

|   |   |   |   |   |   |   |   |   |   |   |   |   |   |   |   |      |
|---|---|---|---|---|---|---|---|---|---|---|---|---|---|---|---|------|
|   |   | 355 |   |   |   |   | 360 |   |   |   |   | 365 |   |   |   |      |
| ctg | ccc | cca | tcc | cgg | gat | gag | ctg | acc | aag | aac | cag | gtc | agc | ctg | acc | 1152 |
| Leu | Pro | Pro | Ser | Arg | Asp | Glu | Leu | Thr | Lys | Asn | Gln | Val | Ser | Leu | Thr |      |
|   | 370 |   |   |   | 375 |   |   |   |   | 380 |   |   |   |   |   |      |
| tgc | ctg | gtc | aaa | ggc | ttc | tat | ccc | agc | gac | atc | gcc | gtg | gag | tgg | gag | 1200 |
| Cys | Leu | Val | Lys | Gly | Phe | Tyr | Pro | Ser | Asp | Ile | Ala | Val | Glu | Trp | Glu |      |
| 385 |   |   |   |   | 390 |   |   |   |   | 395 |   |   |   |   | 400 |      |
| agc | aat | ggg | cag | ccg | gag | aac | aac | tac | aag | acc | acg | cct | ccc | gtg | ctg | 1248 |
| Ser | Asn | Gly | Gln | Pro | Glu | Asn | Asn | Tyr | Lys | Thr | Thr | Pro | Pro | Val | Leu |      |
|   |   |   |   | 405 |   |   |   |   | 410 |   |   |   |   | 415 |   |      |
| gac | tcc | gac | ggc | tcc | ttc | ttc | ctc | tac | agc | aag | ctc | acc | gtg | gac | aag | 1296 |
| Asp | Ser | Asp | Gly | Ser | Phe | Phe | Leu | Tyr | Ser | Lys | Leu | Thr | Val | Asp | Lys |      |
|   |   |   | 420 |   |   |   |   | 425 |   |   |   |   | 430 |   |   |      |
| agc | agg | tgg | cag | cag | ggg | aac | gtc | ttc | tca | tgc | tcc | gtg | atg | cat | gag | 1344 |
| Ser | Arg | Trp | Gln | Gln | Gly | Asn | Val | Phe | Ser | Cys | Ser | Val | Met | His | Glu |      |
|   |   |   | 435 |   |   |   |   | 440 |   |   |   |   | 445 |   |   |      |
| gct | ctg | cac | aac | cac | tac | acg | cag | aag | agc | ctc | tcc | ctg | tct | ccg | ggt | 1392 |
| Ala | Leu | His | Asn | His | Tyr | Thr | Gln | Lys | Ser | Leu | Ser | Leu | Ser | Pro | Gly |      |
|   | 450 |   |   |   |   | 455 |   |   |   |   | 460 |   |   |   |   |      |
| aaa | ggc | ggt | ggc | ggt | tct | ggc | gcg | cct | ttt | aga | gac | tgt | gca | gat | gta | 1440 |
| Lys | Gly | Gly | Gly | Gly | Ser | Gly | Ala | Pro | Phe | Arg | Asp | Cys | Ala | Asp | Val |      |
| 465 |   |   |   |   | 470 |   |   |   |   | 475 |   |   |   |   | 480 |      |
| tat | caa | gct | ggt | ttt | aat | aaa | agt | gga | atc | tac | act | att | tat | att | aat | 1488 |
| Tyr | Gln | Ala | Gly | Phe | Asn | Lys | Ser | Gly | Ile | Tyr | Thr | Ile | Tyr | Ile | Asn |      |
|   |   |   |   | 485 |   |   |   |   | 490 |   |   |   |   | 495 |   |      |
| aat | atg | cca | gaa | ccc | aaa | aag | gtg | ttt | tgc | aat | atg | gat | gtc | aat | ggg | 1536 |
| Asn | Met | Pro | Glu | Pro | Lys | Lys | Val | Phe | Cys | Asn | Met | Asp | Val | Asn | Gly |      |
|   |   |   | 500 |   |   |   |   | 505 |   |   |   |   | 510 |   |   |      |
| gga | ggt | tgg | act | gta | ata | caa | cat | cgt | gaa | gat | gga | agt | cta | gat | ttc | 1584 |
| Gly | Gly | Trp | Thr | Val | Ile | Gln | His | Arg | Glu | Asp | Gly | Ser | Leu | Asp | Phe |      |
|   |   | 515 |   |   |   |   | 520 |   |   |   |   | 525 |   |   |   |      |
| caa | aga | ggc | tgg | aag | gaa | tat | aaa | atg | ggt | ttt | gga | aat | ccc | tcc | ggt | 1632 |
| Gln | Arg | Gly | Trp | Lys | Glu | Tyr | Lys | Met | Gly | Phe | Gly | Asn | Pro | Ser | Gly |      |
|   | 530 |   |   |   |   | 535 |   |   |   |   | 540 |   |   |   |   |      |
| gaa | tat | tgg | ctg | ggg | aat | gag | ttt | att | ttt | gcc | att | acc | agt | cag | agg | 1680 |
| Glu | Tyr | Trp | Leu | Gly | Asn | Glu | Phe | Ile | Phe | Ala | Ile | Thr | Ser | Gln | Arg |      |
| 545 |   |   |   |   | 550 |   |   |   |   | 555 |   |   |   |   | 560 |      |
| cag | tac | atg | cta | aga | att | gag | tta | atg | gac | tgg | gaa | ggg | aac | cga | gcc | 1728 |
| Gln | Tyr | Met | Leu | Arg | Ile | Glu | Leu | Met | Asp | Trp | Glu | Gly | Asn | Arg | Ala |      |
|   |   |   |   | 565 |   |   |   |   | 570 |   |   |   |   | 575 |   |      |
| tat | tca | cag | tat | gac | aga | ttc | cac | ata | gga | aat | gaa | aag | caa | aac | tat | 1776 |
| Tyr | Ser | Gln | Tyr | Asp | Arg | Phe | His | Ile | Gly | Asn | Glu | Lys | Gln | Asn | Tyr |      |
|   |   |   | 580 |   |   |   |   | 585 |   |   |   |   | 590 |   |   |      |
| agg | ttg | tat | tta | aaa | ggt | cac | act | ggg | aca | gca | gga | aaa | cag | agc | agc | 1824 |
| Arg | Leu | Tyr | Leu | Lys | Gly | His | Thr | Gly | Thr | Ala | Gly | Lys | Gln | Ser | Ser |      |
|   |   | 595 |   |   |   |   | 600 |   |   |   |   | 605 |   |   |   |      |
| ctg | atc | tta | cac | ggt | gct | gat | ttc | agc | act | aaa | gat | gct | gat | aat | gac | 1872 |
| Leu | Ile | Leu | His | Gly | Ala | Asp | Phe | Ser | Thr | Lys | Asp | Ala | Asp | Asn | Asp |      |
|   | 610 |   |   |   |   | 615 |   |   |   |   | 620 |   |   |   |   |      |
| aac | tgt | atg | tgc | aaa | tgt | gcc | ctc | atg | tta | aca | gga | gga | tgg | tgg | ttt | 1920 |
| Asn | Cys | Met | Cys | Lys | Cys | Ala | Leu | Met | Leu | Thr | Gly | Gly | Trp | Trp | Phe |      |
| 625 |   |   |   |   | 630 |   |   |   |   | 635 |   |   |   |   | 640 |      |
| gat | gct | tgt | ggc | ccc | tcc | aat | cta | aat | gga | atg | ttc | tat | act | gcg | gga | 1968 |
| Asp | Ala | Cys | Gly | Pro | Ser | Asn | Leu | Asn | Gly | Met | Phe | Tyr | Thr | Ala | Gly |      |
|   |   |   |   | 645 |   |   |   |   | 650 |   |   |   |   | 655 |   |      |
| caa | aac | cat | gga | aaa | ctg | aat | ggg | ata | aag | tgg | cac | tac | ttc | aaa | ggg | 2016 |
| Gln | Asn | His | Gly | Lys | Leu | Asn | Gly | Ile | Lys | Trp | His | Tyr | Phe | Lys | Gly |      |
|   |   |   | 660 |   |   |   |   | 665 |   |   |   |   | 670 |   |   |      |
| cca | agt | tac | tcc | tta | cgt | tcc | aca | act | atg | atg | att | cga | cct | tta | gat | 2064 |

-continued

```
Pro Ser Tyr Ser Leu Arg Ser Thr Thr Met Met Ile Arg Pro Leu Asp
        675                 680                 685
ttt                                                                  2067

<210> SEQ ID NO 6
<211> LENGTH: 688
<212> TYPE: PRT
<213> ORGANISM: Homo sapiens

<400> SEQUENCE: 6

Met Ser Ala Leu Leu Ile Leu Ala Leu Val Gly Ala Ala Val Ala Arg
 1               5                  10                  15

Asp Cys Ala Asp Val Tyr Gln Ala Gly Phe Asn Lys Ser Gly Ile Tyr
            20                  25                  30

Thr Ile Tyr Ile Asn Asn Met Pro Glu Pro Lys Lys Val Phe Cys Asn
        35                  40                  45

Met Asp Val Asn Gly Gly Gly Trp Thr Val Ile Gln His Arg Glu Asp
50                  55                  60

Gly Ser Leu Asp Phe Gln Arg Gly Trp Lys Glu Tyr Lys Met Gly Phe
65                  70                  75                  80

Gly Asn Pro Ser Gly Glu Tyr Trp Leu Gly Asn Glu Phe Ile Phe Ala
                85                  90                  95

Ile Thr Ser Gln Arg Gln Tyr Met Leu Arg Ile Glu Leu Met Asp Trp
            100                 105                 110

Glu Gly Asn Arg Ala Tyr Ser Gln Tyr Asp Arg Phe His Ile Gly Asn
        115                 120                 125

Glu Lys Gln Asn Tyr Arg Leu Tyr Leu Lys Gly His Thr Gly Thr Ala
130                 135                 140

Gly Lys Gln Ser Ser Leu Ile Leu His Gly Ala Asp Phe Ser Thr Lys
145                 150                 155                 160

Asp Ala Asp Asn Asp Asn Cys Met Cys Lys Cys Ala Leu Met Leu Thr
                165                 170                 175

Gly Gly Trp Trp Phe Asp Ala Cys Gly Pro Ser Asn Leu Asn Gly Met
            180                 185                 190

Phe Tyr Thr Ala Gly Gln Asn His Gly Lys Leu Asn Gly Ile Lys Trp
        195                 200                 205

His Tyr Phe Lys Gly Pro Ser Tyr Ser Leu Arg Ser Thr Thr Met Met
210                 215                 220

Ile Arg Pro Leu Asp Phe Gly Pro Gly Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350
```

-continued

| | | | | | | | | | | | |
|---|---|---|---|---|---|---|---|---|---|---|---|
|Thr|Ile|Ser|Lys|Ala|Lys|Gly|Gln|Pro|Arg|Glu|Pro|Gln|Val|Tyr|Thr|
| |355| | | |360| | | |365| | | | | | |

Leu Pro Pro Ser Arg Asp Glu Leu Thr Lys Asn Gln Val Ser Leu Thr
    370             375             380

Cys Leu Val Lys Gly Phe Tyr Pro Ser Asp Ile Ala Val Glu Trp Glu
385             390             395             400

Ser Asn Gly Gln Pro Glu Asn Asn Tyr Lys Thr Thr Pro Pro Val Leu
            405             410             415

Asp Ser Asp Gly Ser Phe Phe Leu Tyr Ser Lys Leu Thr Val Asp Lys
            420             425             430

Ser Arg Trp Gln Gln Gly Asn Val Phe Ser Cys Ser Val Met His Glu
    435             440             445

Ala Leu His Asn His Tyr Thr Gln Lys Ser Leu Ser Leu Ser Pro Gly
450             455             460

Lys Gly Gly Gly Ser Gly Ala Pro Phe Arg Asp Cys Ala Asp Val
465             470             475             480

Tyr Gln Ala Gly Phe Asn Lys Ser Gly Ile Tyr Thr Ile Tyr Ile Asn
            485             490             495

Asn Met Pro Glu Pro Lys Lys Val Phe Cys Asn Met Asp Val Asn Gly
            500             505             510

Gly Gly Trp Thr Val Ile Gln His Arg Glu Asp Gly Ser Leu Asp Phe
    515             520             525

Gln Arg Gly Trp Lys Glu Tyr Lys Met Gly Phe Gly Asn Pro Ser Gly
    530             535             540

Glu Tyr Trp Leu Gly Asn Glu Phe Ile Phe Ala Ile Thr Ser Gln Arg
545             550             555             560

Gln Tyr Met Leu Arg Ile Glu Leu Met Asp Trp Glu Gly Asn Arg Ala
            565             570             575

Tyr Ser Gln Tyr Asp Arg Phe His Ile Gly Asn Glu Lys Gln Asn Tyr
            580             585             590

Arg Leu Tyr Leu Lys Gly His Thr Gly Thr Ala Gly Lys Gln Ser Ser
    595             600             605

Leu Ile Leu His Gly Ala Asp Phe Ser Thr Lys Asp Ala Asp Asn Asp
    610             615             620

Asn Cys Met Cys Lys Cys Ala Leu Met Leu Thr Gly Gly Trp Trp Phe
625             630             635             640

Asp Ala Cys Gly Pro Ser Asn Leu Asn Gly Met Phe Tyr Thr Ala Gly
            645             650             655

Gln Asn His Gly Lys Leu Asn Gly Ile Lys Trp His Tyr Phe Lys Gly
            660             665             670

Pro Ser Tyr Ser Leu Arg Ser Thr Thr Met Met Ile Arg Pro Leu Asp
            675             680             685

<210> SEQ ID NO 7
<211> LENGTH: 2070
<212> TYPE: DNA
<213> ORGANISM: Homo sapiens
<220> FEATURE:
<221> NAME/KEY: CDS
<222> LOCATION: (1)...(2067)

<400> SEQUENCE: 7 atg tct gca ctt ctg atc cta gct ctt gtt gga gct gca gtt gct aga        48
Met Ser Ala Leu Leu Ile Leu Ala Leu Val Gly Ala Ala Val Ala Arg
1               5                   10                  15 gac tgt gct gaa gta ttc aaa tca gga cac acc aca aat ggc atc tac        96

-continued

```
                Asp Cys Ala Glu Val Phe Lys Ser Gly His Thr Thr Asn Gly Ile Tyr
                     20                  25                  30 acg tta aca ttc cct aat tct aca gaa gag atc aag gcc tac tgt gac        144
Thr Leu Thr Phe Pro Asn Ser Thr Glu Glu Ile Lys Ala Tyr Cys Asp
         35                  40                  45 atg gaa gct gga gga ggc ggg tgg aca att att cag cga cgt gag gat        192
Met Glu Ala Gly Gly Gly Gly Trp Thr Ile Ile Gln Arg Arg Glu Asp
 50                  55                  60 ggc agc gtt gat ttt cag agg act tgg aaa gaa tat aaa gtg gga ttt        240
Gly Ser Val Asp Phe Gln Arg Thr Trp Lys Glu Tyr Lys Val Gly Phe
 65                  70                  75                  80 ggt aac cct tca gga gaa tat tgg ctg gga aat gag ttt gtt tcg caa        288
Gly Asn Pro Ser Gly Glu Tyr Trp Leu Gly Asn Glu Phe Val Ser Gln
                 85                  90                  95 ctg act aat cag caa cgc tat gtg ctt aaa ata cac ctt aaa gac tgg        336
Leu Thr Asn Gln Gln Arg Tyr Val Leu Lys Ile His Leu Lys Asp Trp
            100                 105                 110 gaa ggg aat gag gct tac tca ttg tat gaa cat ttc tat ctc tca agt        384
Glu Gly Asn Glu Ala Tyr Ser Leu Tyr Glu His Phe Tyr Leu Ser Ser
        115                 120                 125 gaa gaa ctc aat tat agg att cac ctt aaa gga ctt aca ggg aca gcc        432
Glu Glu Leu Asn Tyr Arg Ile His Leu Lys Gly Leu Thr Gly Thr Ala
    130                 135                 140 ggc aaa ata agc agc atc agc caa cca gga aat gat ttt agc aca aag        480
Gly Lys Ile Ser Ser Ile Ser Gln Pro Gly Asn Asp Phe Ser Thr Lys
145                 150                 155                 160 gat gga gac aac gac aaa tgt att tgc aaa tgt tca caa atg cta aca        528
Asp Gly Asp Asn Asp Lys Cys Ile Cys Lys Cys Ser Gln Met Leu Thr
                165                 170                 175 gga ggc tgg tgg ttt gat gca tgt ggt cct tcc aac ttg aac gga atg        576
Gly Gly Trp Trp Phe Asp Ala Cys Gly Pro Ser Asn Leu Asn Gly Met
            180                 185                 190 tac tat cca cag agg cag aac aca aat aag ttc aac ggc att aaa tgg        624
Tyr Tyr Pro Gln Arg Gln Asn Thr Asn Lys Phe Asn Gly Ile Lys Trp
        195                 200                 205 tac tac tgg aaa ggc tca ggc tat tcg ctc aag gcc aca acc atg atg        672
Tyr Tyr Trp Lys Gly Ser Gly Tyr Ser Leu Lys Ala Thr Thr Met Met
    210                 215                 220 atc cga cca gca gat ttc ggg ggc ccg ggc gag ccc aaa tct tgt gac        720
Ile Arg Pro Ala Asp Phe Gly Gly Pro Gly Glu Pro Lys Ser Cys Asp
225                 230                 235                 240 aaa act cac aca tgc cca ccg tgc cca gca cct gaa ctc ctg ggg gga        768
Lys Thr His Thr Cys Pro Pro Cys Pro Ala Pro Glu Leu Leu Gly Gly
                245                 250                 255 ccg tca gtc ttc ctc ttc ccc cca aaa ccc aag gac acc ctc atg atc        816
Pro Ser Val Phe Leu Phe Pro Pro Lys Pro Lys Asp Thr Leu Met Ile
            260                 265                 270 tcc cgg acc cct gag gtc aca tgc gtg gtg gtg gac gtg agc cac gaa        864
Ser Arg Thr Pro Glu Val Thr Cys Val Val Val Asp Val Ser His Glu
        275                 280                 285 gac cct gag gtc aag ttc aac tgg tac gtg gac ggc gtg gag gtg cat        912
Asp Pro Glu Val Lys Phe Asn Trp Tyr Val Asp Gly Val Glu Val His
    290                 295                 300 aat gcc aag aca aag ccg cgg gag gag cag tac aac agc acg tac cgt        960
Asn Ala Lys Thr Lys Pro Arg Glu Glu Gln Tyr Asn Ser Thr Tyr Arg
305                 310                 315                 320 gtg gtc agc gtc ctc acc gtc ctg cac cag gac tgg ctg aat ggc aag       1008
Val Val Ser Val Leu Thr Val Leu His Gln Asp Trp Leu Asn Gly Lys
                325                 330                 335
```

```
gag tac aag tgc aag gtc tcc aac aaa gcc ctc cca gcc ccc atc gag      1056
Glu Tyr Lys Cys Lys Val Ser Asn Lys Ala Leu Pro Ala Pro Ile Glu
            340                 345                 350 aaa acc atc tcc aaa gcc aaa ggg cag ccc cga gaa cca cag gtg tac      1104
Lys Thr Ile Ser Lys Ala Lys Gly Gln Pro Arg Glu Pro Gln Val Tyr
    355                 360                 365 acc ctg ccc cca tcc cgg gat gag ctg acc aag aac cag gtc agc ctg      1152
Thr Leu Pro Pro Ser Arg Asp Glu Leu Thr Lys Asn Gln Val Ser Leu
370                 375                 380 acc tgc ctg gtc aaa ggc ttc tat ccc agc gac atc gcc gtg gag tgg      1200
Thr Cys Leu Val Lys Gly Phe Tyr Pro Ser Asp Ile Ala Val Glu Trp
385                 390                 395                 400 gag agc aat ggg cag ccg gag aac aac tac aag acc acg cct ccc gtg      1248
Glu Ser Asn Gly Gln Pro Glu Asn Asn Tyr Lys Thr Thr Pro Pro Val
            405                 410                 415 ctg gac tcc gac ggc tcc ttc ttc ctc tac agc aag ctc acc gtg gac      1296
Leu Asp Ser Asp Gly Ser Phe Phe Leu Tyr Ser Lys Leu Thr Val Asp
            420                 425                 430 aag agc agg tgg cag cag ggg aac gtc ttc tca tgc tcc gtg atg cat      1344
Lys Ser Arg Trp Gln Gln Gly Asn Val Phe Ser Cys Ser Val Met His
    435                 440                 445 gag gct ctg cac aac cac tac acg cag aag agc ctc tcc ctg tct ccg      1392
Glu Ala Leu His Asn His Tyr Thr Gln Lys Ser Leu Ser Leu Ser Pro
450                 455                 460 ggt aaa ggc ggt ggc ggt tct ggc gcg cct aga gac tgt gct gaa gta      1440
Gly Lys Gly Gly Gly Gly Ser Gly Ala Pro Arg Asp Cys Ala Glu Val
465                 470                 475                 480 ttc aaa tca gga cac acc aca aat ggc atc tac acg tta aca ttc cct      1488
Phe Lys Ser Gly His Thr Thr Asn Gly Ile Tyr Thr Leu Thr Phe Pro
            485                 490                 495 aat tct aca gaa gag atc aag gcc tac tgt gac atg gaa gct gga gga      1536
Asn Ser Thr Glu Glu Ile Lys Ala Tyr Cys Asp Met Glu Ala Gly Gly
            500                 505                 510 ggc ggg tgg aca att att cag cga cgt gag gat ggc agc gtt gat ttt      1584
Gly Gly Trp Thr Ile Ile Gln Arg Arg Glu Asp Gly Ser Val Asp Phe
    515                 520                 525 cag agg act tgg aaa gaa tat aaa gtg gga ttt ggt aac cct tca gga      1632
Gln Arg Thr Trp Lys Glu Tyr Lys Val Gly Phe Gly Asn Pro Ser Gly
530                 535                 540 gaa tat tgg ctg gga aat gag ttt gtt tcg caa ctg act aat cag caa      1680
Glu Tyr Trp Leu Gly Asn Glu Phe Val Ser Gln Leu Thr Asn Gln Gln
545                 550                 555                 560 cgc tat gtg ctt aaa ata cac ctt aaa gac tgg gaa ggg aat gag gct      1728
Arg Tyr Val Leu Lys Ile His Leu Lys Asp Trp Glu Gly Asn Glu Ala
            565                 570                 575 tac tca ttg tat gaa cat ttc tat ctc tca agt gaa gaa ctc aat tat      1776
Tyr Ser Leu Tyr Glu His Phe Tyr Leu Ser Ser Glu Glu Leu Asn Tyr
            580                 585                 590 agg att cac ctt aaa gga ctt aca ggg aca gcc ggc aaa ata agc agc      1824
Arg Ile His Leu Lys Gly Leu Thr Gly Thr Ala Gly Lys Ile Ser Ser
    595                 600                 605 atc agc caa cca gga aat gat ttt agc aca aag gat gga gac aac gac      1872
Ile Ser Gln Pro Gly Asn Asp Phe Ser Thr Lys Asp Gly Asp Asn Asp
610                 615                 620 aaa tgt att tgc aaa tgt tca caa atg cta aca gga ggc tgg tgg ttt      1920
Lys Cys Ile Cys Lys Cys Ser Gln Met Leu Thr Gly Gly Trp Trp Phe
625                 630                 635                 640 gat gca tgt ggt cct tcc aac ttg aac gga atg tac tat cca cag agg      1968
Asp Ala Cys Gly Pro Ser Asn Leu Asn Gly Met Tyr Tyr Pro Gln Arg
            645                 650                 655
```

-continued

```
cag aac aca aat aag ttc aac ggc att aaa tgg tac tac tgg aaa ggc     2016
Gln Asn Thr Asn Lys Phe Asn Gly Ile Lys Trp Tyr Tyr Trp Lys Gly
            660                 665                 670 tca ggc tat tcg ctc aag gcc aca acc atg atg atc cga cca gca gat     2064
Ser Gly Tyr Ser Leu Lys Ala Thr Thr Met Met Ile Arg Pro Ala Asp
        675                 680                 685 ttc tga                                                              2070
Phe

<210> SEQ ID NO 8
<211> LENGTH: 689
<212> TYPE: PRT
<213> ORGANISM: Homo sapiens

<400> SEQUENCE: 8

Met Ser Ala Leu Leu Ile Leu Ala Leu Val Gly Ala Ala Val Ala Arg
  1               5                  10                  15

Asp Cys Ala Glu Val Phe Lys Ser Gly His Thr Thr Asn Gly Ile Tyr
                 20                  25                  30

Thr Leu Thr Phe Pro Asn Ser Thr Glu Glu Ile Lys Ala Tyr Cys Asp
             35                  40                  45

Met Glu Ala Gly Gly Gly Gly Trp Thr Ile Ile Gln Arg Arg Glu Asp
         50                  55                  60

Gly Ser Val Asp Phe Gln Arg Thr Trp Lys Glu Tyr Lys Val Gly Phe
 65                  70                  75                  80

Gly Asn Pro Ser Gly Glu Tyr Trp Leu Gly Asn Glu Phe Val Ser Gln
                 85                  90                  95

Leu Thr Asn Gln Gln Arg Tyr Val Leu Lys Ile His Leu Lys Asp Trp
            100                 105                 110

Glu Gly Asn Glu Ala Tyr Ser Leu Tyr Glu His Phe Tyr Leu Ser Ser
        115                 120                 125

Glu Glu Leu Asn Tyr Arg Ile His Leu Lys Gly Leu Thr Gly Thr Ala
    130                 135                 140

Gly Lys Ile Ser Ser Ile Ser Gln Pro Gly Asn Asp Phe Ser Thr Lys
145                 150                 155                 160

Asp Gly Asp Asn Asp Lys Cys Ile Cys Lys Cys Ser Gln Met Leu Thr
                165                 170                 175

Gly Gly Trp Trp Phe Asp Ala Cys Gly Pro Ser Asn Leu Asn Gly Met
            180                 185                 190

Tyr Tyr Pro Gln Arg Gln Asn Thr Asn Lys Phe Asn Gly Ile Lys Trp
        195                 200                 205

Tyr Tyr Trp Lys Gly Ser Gly Tyr Ser Leu Lys Ala Thr Thr Met Met
    210                 215                 220

Ile Arg Pro Ala Asp Phe Gly Pro Gly Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320
```

```
Val Val Ser Val Leu Thr Val Leu His Gln Asp Trp Leu Asn Gly Lys
            325                 330                 335
Glu Tyr Lys Cys Lys Val Ser Asn Lys Ala Leu Pro Ala Pro Ile Glu
        340                 345                 350
Lys Thr Ile Ser Lys Ala Lys Gly Gln Pro Arg Glu Pro Gln Val Tyr
    355                 360                 365
Thr Leu Pro Pro Ser Arg Asp Glu Leu Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys Gly Gly Gly Gly Ser Gly Ala Pro Arg Asp Cys Ala Glu Val
465                 470                 475                 480
Phe Lys Ser Gly His Thr Thr Asn Gly Ile Tyr Thr Leu Thr Phe Pro
                485                 490                 495
Asn Ser Thr Glu Glu Ile Lys Ala Tyr Cys Asp Met Glu Ala Gly Gly
            500                 505                 510
Gly Gly Trp Thr Ile Ile Gln Arg Arg Glu Asp Gly Ser Val Asp Phe
        515                 520                 525
Gln Arg Thr Trp Lys Glu Tyr Lys Val Gly Phe Gly Asn Pro Ser Gly
    530                 535                 540
Glu Tyr Trp Leu Gly Asn Glu Phe Val Ser Gln Leu Thr Asn Gln Gln
545                 550                 555                 560
Arg Tyr Val Leu Lys Ile His Leu Lys Asp Trp Glu Gly Asn Glu Ala
                565                 570                 575
Tyr Ser Leu Tyr Glu His Phe Tyr Leu Ser Ser Glu Glu Leu Asn Tyr
            580                 585                 590
Arg Ile His Leu Lys Gly Leu Thr Gly Thr Ala Gly Lys Ile Ser Ser
        595                 600                 605
Ile Ser Gln Pro Gly Asn Asp Phe Ser Thr Lys Asp Gly Asp Asn Asp
    610                 615                 620
Lys Cys Ile Cys Lys Cys Ser Gln Met Leu Thr Gly Gly Trp Trp Phe
625                 630                 635                 640
Asp Ala Cys Gly Pro Ser Asn Leu Asn Gly Met Tyr Tyr Pro Gln Arg
                645                 650                 655
Gln Asn Thr Asn Lys Phe Asn Gly Ile Lys Trp Tyr Tyr Trp Lys Gly
            660                 665                 670
Ser Gly Tyr Ser Leu Lys Ala Thr Thr Met Met Ile Arg Pro Ala Asp
        675                 680                 685
Phe

<210> SEQ ID NO 9
<211> LENGTH: 2052
<212> TYPE: DNA
<213> ORGANISM: Homo sapiens
<220> FEATURE:
<221> NAME/KEY: CDS
```

-continued

<222> LOCATION: (1)...(2049)

<400> SEQUENCE: 9

| | | | | | | | | | | | | | | | | |
|---|---|---|---|---|---|---|---|---|---|---|---|---|---|---|---|---|
| atg | gct | cgg | cct | ggg | cag | cgt | tgg | ctc | ggc | aag | tgg | ctt | gtg | gcg | atg | 48 |
| Met | Ala | Arg | Pro | Gly | Gln | Arg | Trp | Leu | Gly | Lys | Trp | Leu | Val | Ala | Met | |
| 1 | | | 5 | | | | | 10 | | | | | 15 | | | |
| gtc | gtg | tgg | gcg | ctg | tgc | cgg | ctc | gcc | aca | ccg | ctg | gcc | aag | aac | ctg | 96 |
| Val | Val | Trp | Ala | Leu | Cys | Arg | Leu | Ala | Thr | Pro | Leu | Ala | Lys | Asn | Leu | |
| | | 20 | | | | | 25 | | | | | 30 | | | | |
| gag | ccc | gta | tcc | tgg | agc | tcc | ctc | aac | ccc | aag | ttc | ctg | agt | ggg | aag | 144 |
| Glu | Pro | Val | Ser | Trp | Ser | Ser | Leu | Asn | Pro | Lys | Phe | Leu | Ser | Gly | Lys | |
| | 35 | | | | | 40 | | | | | 45 | | | | | |
| ggc | ttg | gtg | atc | tat | ccg | aaa | att | gga | gac | aag | ctg | gac | atc | atc | tgc | 192 |
| Gly | Leu | Val | Ile | Tyr | Pro | Lys | Ile | Gly | Asp | Lys | Leu | Asp | Ile | Ile | Cys | |
| 50 | | | | | 55 | | | | | 60 | | | | | | |
| ccc | cga | gca | gaa | gca | ggg | cgg | ccc | tat | gag | tac | tac | aag | ctg | tac | ctg | 240 |
| Pro | Arg | Ala | Glu | Ala | Gly | Arg | Pro | Tyr | Glu | Tyr | Tyr | Lys | Leu | Tyr | Leu | |
| 65 | | | | 70 | | | | | 75 | | | | | 80 | | |
| gtg | cgg | cct | gag | cag | gca | gct | gcc | tgt | agc | aca | gtt | ctc | gac | ccc | aac | 288 |
| Val | Arg | Pro | Glu | Gln | Ala | Ala | Ala | Cys | Ser | Thr | Val | Leu | Asp | Pro | Asn | |
| | | | | 85 | | | | | 90 | | | | | 95 | | |
| gtg | ttg | gtc | acc | tgc | aat | agg | cca | gag | cag | gaa | ata | cgc | ttt | acc | atc | 336 |
| Val | Leu | Val | Thr | Cys | Asn | Arg | Pro | Glu | Gln | Glu | Ile | Arg | Phe | Thr | Ile | |
| | | | 100 | | | | | 105 | | | | | 110 | | | |
| aag | ttc | cag | gag | ttc | agc | ccc | aac | tac | atg | ggc | ctg | gag | ttc | aag | aag | 384 |
| Lys | Phe | Gln | Glu | Phe | Ser | Pro | Asn | Tyr | Met | Gly | Leu | Glu | Phe | Lys | Lys | |
| | | 115 | | | | | 120 | | | | | 125 | | | | |
| cac | cat | gat | tac | tac | att | acc | tca | aca | tcc | aat | gga | agc | ctg | gag | ggg | 432 |
| His | His | Asp | Tyr | Tyr | Ile | Thr | Ser | Thr | Ser | Asn | Gly | Ser | Leu | Glu | Gly | |
| | 130 | | | | | 135 | | | | | 140 | | | | | |
| ctg | gaa | aac | cgg | gag | ggc | ggt | gtg | tgc | cgc | aca | cgc | acc | atg | aag | atc | 480 |
| Leu | Glu | Asn | Arg | Glu | Gly | Gly | Val | Cys | Arg | Thr | Arg | Thr | Met | Lys | Ile | |
| 145 | | | | | 150 | | | | | 155 | | | | | 160 | |
| atc | atg | aag | gtt | ggg | caa | gat | ccc | aat | gct | gtg | acg | cct | gag | cag | ctg | 528 |
| Ile | Met | Lys | Val | Gly | Gln | Asp | Pro | Asn | Ala | Val | Thr | Pro | Glu | Gln | Leu | |
| | | | | 165 | | | | | 170 | | | | | 175 | | |
| act | acc | agc | agg | ccc | agc | aag | gag | gca | gac | aac | act | gtc | aag | atg | gcc | 576 |
| Thr | Thr | Ser | Arg | Pro | Ser | Lys | Glu | Ala | Asp | Asn | Thr | Val | Lys | Met | Ala | |
| | | | 180 | | | | | 185 | | | | | 190 | | | |
| aca | cag | gcc | cct | ggt | agt | cgg | ggc | tcc | ctg | ggt | gac | tct | gat | ggc | aag | 624 |
| Thr | Gln | Ala | Pro | Gly | Ser | Arg | Gly | Ser | Leu | Gly | Asp | Ser | Asp | Gly | Lys | |
| | | 195 | | | | | 200 | | | | | 205 | | | | |
| cat | gag | act | gtg | aac | cag | gaa | gag | aag | agt | ggc | cca | ggt | gca | agt | ggg | 672 |
| His | Glu | Thr | Val | Asn | Gln | Glu | Glu | Lys | Ser | Gly | Pro | Gly | Ala | Ser | Gly | |
| 210 | | | | | 215 | | | | | 220 | | | | | | |
| ggc | agc | agc | ggg | gac | cct | gat | ggc | ttc | ttc | aac | tcc | aag | ggc | ccg | ggt | 720 |
| Gly | Ser | Ser | Gly | Asp | Pro | Asp | Gly | Phe | Phe | Asn | Ser | Lys | Gly | Pro | Gly | |
| 225 | | | | | 230 | | | | | 235 | | | | | 240 | |
| aag | aac | ctg | gag | ccc | gta | tcc | tgg | agc | tcc | ctc | aac | ccc | aag | ttc | ctg | 768 |
| Lys | Asn | Leu | Glu | Pro | Val | Ser | Trp | Ser | Ser | Leu | Asn | Pro | Lys | Phe | Leu | |
| | | | | 245 | | | | | 250 | | | | | 255 | | |
| agt | ggg | aag | ggc | ttg | gtg | atc | tat | ccg | aaa | att | gga | gac | aag | ctg | gac | 816 |
| Ser | Gly | Lys | Gly | Leu | Val | Ile | Tyr | Pro | Lys | Ile | Gly | Asp | Lys | Leu | Asp | |
| | | | 260 | | | | | 265 | | | | | 270 | | | |
| atc | atc | tgc | ccc | cga | gca | gaa | gca | ggg | cgg | ccc | tat | gag | tac | tac | aag | 864 |
| Ile | Ile | Cys | Pro | Arg | Ala | Glu | Ala | Gly | Arg | Pro | Tyr | Glu | Tyr | Tyr | Lys | |
| | | 275 | | | | | 280 | | | | | 285 | | | | |
| ctg | tac | ctg | gtg | cgg | cct | gag | cag | gca | gct | gcc | tgt | agc | aca | gtt | ctc | 912 |
| Leu | Tyr | Leu | Val | Arg | Pro | Glu | Gln | Ala | Ala | Ala | Cys | Ser | Thr | Val | Leu | |
| | 290 | | | | | 295 | | | | | 300 | | | | | |

-continued

| | |
|---|---|
| gac ccc aac gtg ttg gtc acc tgc aat agg cca gag cag gaa ata cgc<br>Asp Pro Asn Val Leu Val Thr Cys Asn Arg Pro Glu Gln Glu Ile Arg<br>305                    310                    315                    320 | 960 |
| ttt acc atc aag ttc cag gag ttc agc ccc aac tac atg ggc ctg gag<br>Phe Thr Ile Lys Phe Gln Glu Phe Ser Pro Asn Tyr Met Gly Leu Glu<br>                    325                    330                    335 | 1008 |
| ttc aag aag cac cat gat tac tac att acc tca aca tcc aat gga agc<br>Phe Lys Lys His His Asp Tyr Tyr Ile Thr Ser Thr Ser Asn Gly Ser<br>           340                    345                    350 | 1056 |
| ctg gag ggg ctg gaa aac cgg gag ggc ggt gtg tgc cgc aca cgc acc<br>Leu Glu Gly Leu Glu Asn Arg Glu Gly Gly Val Cys Arg Thr Arg Thr<br>                355                    360                    365 | 1104 |
| atg aag atc atc atg aag gtt ggg caa gat ccc aat gct gtg acg cct<br>Met Lys Ile Ile Met Lys Val Gly Gln Asp Pro Asn Ala Val Thr Pro<br>370                    375                    380 | 1152 |
| gag cag ctg act acc agc agg ccc agc aag gag gca gac aac act gtc<br>Glu Gln Leu Thr Thr Ser Arg Pro Ser Lys Glu Ala Asp Asn Thr Val<br>385                    390                    395                    400 | 1200 |
| aag atg gcc aca cag gcc cct ggt agt cgg ggc tcc ctg ggt gac tct<br>Lys Met Ala Thr Gln Ala Pro Gly Ser Arg Gly Ser Leu Gly Asp Ser<br>                    405                    410                    415 | 1248 |
| gat ggc aag cat gag act gtg aac cag gaa gag aag agt ggc cca ggt<br>Asp Gly Lys His Glu Thr Val Asn Gln Glu Glu Lys Ser Gly Pro Gly<br>           420                    425                    430 | 1296 |
| gca agt ggg ggc agc agc ggg gac cct gat ggc ttc ttc aac tcc aaa<br>Ala Ser Gly Gly Ser Ser Gly Asp Pro Asp Gly Phe Phe Asn Ser Lys<br>                435                    440                    445 | 1344 |
| ggc ccg ggc gag ccc aaa tct tgt gac aaa act cac aca tgc cca ccg<br>Gly Pro Gly Glu Pro Lys Ser Cys Asp Lys Thr His Thr Cys Pro Pro<br>450                    455                    460 | 1392 |
| tgc cca gca cct gaa ctc ctg gga gga ccg tca gtc ttc ctc ttc ccc<br>Cys Pro Ala Pro Glu Leu Leu Gly Gly Pro Ser Val Phe Leu Phe Pro<br>465                    470                    475                    480 | 1440 |
| cca aaa ccc aag gac acc ctc atg atc tcc cgg acc cct gag gtc aca<br>Pro Lys Pro Lys Asp Thr Leu Met Ile Ser Arg Thr Pro Glu Val Thr<br>                    485                    490                    495 | 1488 |
| tgc gtg gtg gtg gac gtg agc cac gaa gac cct gag gtc aag ttc aac<br>Cys Val Val Val Asp Val Ser His Glu Asp Pro Glu Val Lys Phe Asn<br>           500                    505                    510 | 1536 |
| tgg tac gtg gac ggc gtg gag gtg cat aat gcc aag aca aag ccg cgg<br>Trp Tyr Val Asp Gly Val Glu Val His Asn Ala Lys Thr Lys Pro Arg<br>                515                    520                    525 | 1584 |
| gag gag cag tac aac agc acg tac cgt gtg gtc agc gtc ctc acc gtc<br>Glu Glu Gln Tyr Asn Ser Thr Tyr Arg Val Val Ser Val Leu Thr Val<br>530                    535                    540 | 1632 |
| ctg cac cag gac tgg ctg aat ggc aag gag tac aag tgc aag gtc tcc<br>Leu His Gln Asp Trp Leu Asn Gly Lys Glu Tyr Lys Cys Lys Val Ser<br>545                    550                    555                    560 | 1680 |
| aac aaa gcc ctc cca gcc ccc atc gag aaa acc atc tcc aaa gcc aaa<br>Asn Lys Ala Leu Pro Ala Pro Ile Glu Lys Thr Ile Ser Lys Ala Lys<br>                    565                    570                    575 | 1728 |
| ggg cag ccc cga gaa cca cag gtg tac acc ctg ccc cca tcc cgg gat<br>Gly Gln Pro Arg Glu Pro Gln Val Tyr Thr Leu Pro Pro Ser Arg Asp<br>           580                    585                    590 | 1776 |
| gag ctg acc aag aac cag gtc agc ctg acc tgc ctg gtc aaa ggc ttc<br>Glu Leu Thr Lys Asn Gln Val Ser Leu Thr Cys Leu Val Lys Gly Phe<br>                595                    600                    605 | 1824 |
| tat ccc agc gac atc gcc gtg gag tgg gag agc aat ggg cag ccg gag<br>Tyr Pro Ser Asp Ile Ala Val Glu Trp Glu Ser Asn Gly Gln Pro Glu | 1872 |

```
                    610                 615                 620
aac aac tac aag acc acg cct ccc gtg ctg gac tcc gac ggc tcc ttc    1920
Asn Asn Tyr Lys Thr Thr Pro Pro Val Leu Asp Ser Asp Gly Ser Phe
625                 630                 635                 640 ttc ctc tac agc aag ctc acc gtg gac aag agc agg tgg cag cag ggg    1968
Phe Leu Tyr Ser Lys Leu Thr Val Asp Lys Ser Arg Trp Gln Gln Gly
                645                 650                 655 aac gtc ttc tca tgc tcc gtg atg cat gag gct ctg cac aac cac tac    2016
Asn Val Phe Ser Cys Ser Val Met His Glu Ala Leu His Asn His Tyr
                660                 665                 670 acg cag aag agc ctc tcc ctg tct ccg ggt aaa tga                    2052
Thr Gln Lys Ser Leu Ser Leu Ser Pro Gly Lys
                675                 680

<210> SEQ ID NO 10
<211> LENGTH: 683
<212> TYPE: PRT
<213> ORGANISM: Homo sapiens

<400> SEQUENCE: 10

Met Ala Arg Pro Gly Gln Arg Trp Leu Gly Lys Trp Leu Val Ala Met
 1               5                  10                  15

Val Val Trp Ala Leu Cys Arg Leu Ala Thr Pro Leu Ala Lys Asn Leu
                20                  25                  30

Glu Pro Val Ser Trp Ser Ser Leu Asn Pro Lys Phe Leu Ser Gly Lys
            35                  40                  45

Gly Leu Val Ile Tyr Pro Lys Ile Gly Asp Lys Leu Asp Ile Ile Cys
        50                  55                  60

Pro Arg Ala Glu Ala Gly Arg Pro Tyr Glu Tyr Tyr Lys Leu Tyr Leu
65                  70                  75                  80

Val Arg Pro Glu Gln Ala Ala Cys Ser Thr Val Leu Asp Pro Asn
                85                  90                  95

Val Leu Val Thr Cys Asn Arg Pro Glu Gln Ile Arg Phe Thr Ile
            100                 105                 110

Lys Phe Gln Glu Phe Ser Pro Asn Tyr Met Gly Leu Glu Phe Lys Lys
        115                 120                 125

His His Asp Tyr Tyr Ile Thr Ser Thr Ser Asn Gly Ser Leu Glu Gly
        130                 135                 140

Leu Glu Asn Arg Glu Gly Gly Val Cys Arg Thr Arg Thr Met Lys Ile
145                 150                 155                 160

Ile Met Lys Val Gly Gln Asp Pro Asn Ala Val Thr Pro Glu Gln Leu
                165                 170                 175

Thr Thr Ser Arg Pro Ser Lys Glu Ala Asp Asn Thr Val Lys Met Ala
            180                 185                 190

Thr Gln Ala Pro Gly Ser Arg Gly Ser Leu Gly Asp Ser Asp Gly Lys
        195                 200                 205

His Glu Thr Val Asn Gln Glu Glu Lys Ser Gly Pro Gly Ala Ser Gly
        210                 215                 220

Gly Ser Ser Gly Asp Pro Asp Gly Phe Phe Asn Ser Lys Gly Pro Gly
225                 230                 235                 240

Lys Asn Leu Glu Pro Val Ser Trp Ser Ser Leu Asn Pro Lys Phe Leu
                245                 250                 255

Ser Gly Lys Gly Leu Val Ile Tyr Pro Lys Ile Gly Asp Lys Leu Asp
            260                 265                 270

Ile Ile Cys Pro Arg Ala Glu Ala Gly Arg Pro Tyr Glu Tyr Tyr Lys
        275                 280                 285
```

```
Leu Tyr Leu Val Arg Pro Glu Gln Ala Ala Cys Ser Thr Val Leu
    290                 295                 300

Asp Pro Asn Val Leu Val Thr Cys Asn Arg Pro Gln Glu Ile Arg
305                 310                 315                 320

Phe Thr Ile Lys Phe Gln Glu Phe Ser Pro Asn Tyr Met Gly Leu Glu
                325                 330                 335

Phe Lys Lys His His Asp Tyr Tyr Ile Thr Ser Thr Ser Asn Gly Ser
                340                 345                 350

Leu Glu Gly Leu Glu Asn Arg Glu Gly Gly Val Cys Arg Thr Arg Thr
            355                 360                 365

Met Lys Ile Ile Met Lys Val Gly Gln Asp Pro Asn Ala Val Thr Pro
        370                 375                 380

Glu Gln Leu Thr Thr Ser Arg Pro Ser Lys Glu Ala Asp Asn Thr Val
385                 390                 395                 400

Lys Met Ala Thr Gln Ala Pro Gly Ser Arg Gly Ser Leu Gly Asp Ser
                405                 410                 415

Asp Gly Lys His Glu Thr Val Asn Gln Glu Lys Ser Gly Pro Gly
            420                 425                 430

Ala Ser Gly Gly Ser Ser Gly Asp Pro Asp Gly Phe Phe Asn Ser Lys
        435                 440                 445

Gly Pro Gly Glu Pro Lys Ser Cys Asp Lys Thr His Thr Cys Pro Pro
    450                 455                 460

Cys Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
                500                 505                 510

Trp Tyr Val Asp Gly Val Glu Val His Asn Ala Lys Thr Lys Pro Arg
            515                 520                 525

Glu Glu Gln Tyr Asn Ser Thr Tyr Arg Val Val Ser Val Leu Thr Val
        530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Asp
            580                 585                 590

Glu Leu Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
        675                 680

<210> SEQ ID NO 11
<211> LENGTH: 1977
```

```
<212> TYPE: DNA
<213> ORGANISM: Artificial Sequence
<220> FEATURE:
<223> OTHER INFORMATION: Ephrin-B2-Ephrin-B2-Fc
<220> FEATURE:
<221> NAME/KEY: CDS
<222> LOCATION: (1)...(1974)

<400> SEQUENCE: 11 atg gcc atg gcc cgg tcc agg agg gac tct gtg tgg aag tac tgt tgg      48
Met Ala Met Ala Arg Ser Arg Arg Asp Ser Val Trp Lys Tyr Cys Trp
 1               5                  10                  15 gga ctt ttg atg gtt ttg tgc aga act gcg atc tcc aga tcg ata gtt      96
Gly Leu Leu Met Val Leu Cys Arg Thr Ala Ile Ser Arg Ser Ile Val
             20                  25                  30 tta gag cct atc tac tgg aat tcc tcg aac tcc aaa ttt cta ccc gga     144
Leu Glu Pro Ile Tyr Trp Asn Ser Ser Asn Ser Lys Phe Leu Pro Gly
         35                  40                  45 caa ggc ctg gta cta tac cca cag ata gga gac aaa ttg gat att att     192
Gln Gly Leu Val Leu Tyr Pro Gln Ile Gly Asp Lys Leu Asp Ile Ile
     50                  55                  60 tgc ccc aaa gtg gac tct aaa act gtt ggc cag tat gaa tat tat aaa     240
Cys Pro Lys Val Asp Ser Lys Thr Val Gly Gln Tyr Glu Tyr Tyr Lys
 65                  70                  75                  80 gtt tat atg gtt gat aaa gac caa gca gac aga tgc aca att aag aag     288
Val Tyr Met Val Asp Lys Asp Gln Ala Asp Arg Cys Thr Ile Lys Lys
                 85                  90                  95 gag aat acc ccg ctg ctc aac tgt gcc aga cca gac caa gat gtg aaa     336
Glu Asn Thr Pro Leu Leu Asn Cys Ala Arg Pro Asp Gln Asp Val Lys
            100                 105                 110 ttc acc atc aag ttt caa gaa ttc agc cct aac ctc tgg ggt cta gaa     384
Phe Thr Ile Lys Phe Gln Glu Phe Ser Pro Asn Leu Trp Gly Leu Glu
        115                 120                 125 ttt cag aag aac aaa gat tac tac att ata tct aca tca aat ggg tct     432
Phe Gln Lys Asn Lys Asp Tyr Tyr Ile Ile Ser Thr Ser Asn Gly Ser
    130                 135                 140 ttg gag ggc ctg gat aac cag gag gga ggg gtg tgc cag aca aga gcc     480
Leu Glu Gly Leu Asp Asn Gln Glu Gly Gly Val Cys Gln Thr Arg Ala
145                 150                 155                 160 atg aag atc ctc atg aaa gtt gga caa gat gca agt tct gct gga tca     528
Met Lys Ile Leu Met Lys Val Gly Gln Asp Ala Ser Ser Ala Gly Ser
                165                 170                 175 gcc agg aat cac ggt cca aca aga cgt cca gag cta gaa gct ggt aca     576
Ala Arg Asn His Gly Pro Thr Arg Arg Pro Glu Leu Glu Ala Gly Thr
            180                 185                 190 aat ggg aga agt tca aca aca agt ccc ttt gtg aag cca aat cca ggt     624
Asn Gly Arg Ser Ser Thr Thr Ser Pro Phe Val Lys Pro Asn Pro Gly
        195                 200                 205 tct agc acc gat ggc aac agc gcg ggg cat tcc ggg aac aat ctc ctg     672
Ser Ser Thr Asp Gly Asn Ser Ala Gly His Ser Gly Asn Asn Leu Leu
    210                 215                 220 ggg ggc ccg gga ata gtt tta gag cct atc tac tgg aat tcc tcg aac     720
Gly Gly Pro Gly Ile Val Leu Glu Pro Ile Tyr Trp Asn Ser Ser Asn
225                 230                 235                 240 tcc aaa ttt cta ccc gga caa ggc ctg gta cta tac cca cag ata gga     768
Ser Lys Phe Leu Pro Gly Gln Gly Leu Val Leu Tyr Pro Gln Ile Gly
                245                 250                 255 gac aaa ttg gat att att tgc ccc aaa gtg gac tct aaa act gtt ggc     816
Asp Lys Leu Asp Ile Ile Cys Pro Lys Val Asp Ser Lys Thr Val Gly
            260                 265                 270 cag tat gaa tat tat aaa gtt tat atg gtt gat aaa gac caa gca gac     864
```

-continued

| | | |
|---|---|---|
| Gln Tyr Glu Tyr Tyr Lys Val Tyr Met Val Asp Lys Asp Gln Ala Asp<br>275 280 285 | | |
| aga tgc aca att aag aag gag aat acc ccg ctg ctc aac tgt gcc aga<br>Arg Cys Thr Ile Lys Lys Glu Asn Thr Pro Leu Leu Asn Cys Ala Arg<br>290 295 300 | 912 | |
| cca gac caa gat gtg aaa ttc acc atc aag ttt caa gaa ttc agc cct<br>Pro Asp Gln Asp Val Lys Phe Thr Ile Lys Phe Gln Glu Phe Ser Pro<br>305 310 315 320 | 960 | |
| aac ctc tgg ggt cta gaa ttt cag aag aac aaa gat tac tac att ata<br>Asn Leu Trp Gly Leu Glu Phe Gln Lys Asn Lys Asp Tyr Tyr Ile Ile<br>325 330 335 | 1008 | |
| tct aca tca aat ggg tct ttg gag ggc ctg gat aac cag gag gga ggg<br>Ser Thr Ser Asn Gly Ser Leu Glu Gly Leu Asp Asn Gln Glu Gly Gly<br>340 345 350 | 1056 | |
| gtg tgc cag aca aga gcc atg aag atc ctc atg aaa gtt gga caa gat<br>Val Cys Gln Thr Arg Ala Met Lys Ile Leu Met Lys Val Gly Gln Asp<br>355 360 365 | 1104 | |
| gca agt tct gct gga tca gcc agg aat cac ggt cca aca aga cgc cca<br>Ala Ser Ser Ala Gly Ser Ala Arg Asn His Gly Pro Thr Arg Arg Pro<br>370 375 380 | 1152 | |
| gag cta gaa gct ggt aca aat ggg aga agt tca aca aca agt ccc ttt<br>Glu Leu Glu Ala Gly Thr Asn Gly Arg Ser Ser Thr Thr Ser Pro Phe<br>385 390 395 400 | 1200 | |
| gtg aag cca aat cca ggt tct agc acc gat ggc aac agc gcg ggg cat<br>Val Lys Pro Asn Pro Gly Ser Ser Thr Asp Gly Asn Ser Ala Gly His<br>405 410 415 | 1248 | |
| tcc ggg aac aat ctc ctg ggg ggc ccg ggc gag ccc aaa tct tgt gac<br>Ser Gly Asn Asn Leu Leu Gly Gly Pro Gly Glu Pro Lys Ser Cys Asp<br>420 425 430 | 1296 | |
| aaa act cac aca tgc cca ccg tgc cca gca cct gaa ctc ctg ggg gga<br>Lys Thr His Thr Cys Pro Pro Cys Pro Ala Pro Glu Leu Leu Gly Gly<br>435 440 445 | 1344 | |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>450 455 460 | 1392 | |
| tcc cgg acc cct gag gtc aca tgc gtg gtg gtg gac gtg agc cac gaa<br>Ser Arg Thr Pro Glu Val Thr Cys Val Val Val Asp Val Ser His Glu<br>465 470 475 480 | 1440 | |
| gac cct gag gtc aag ttc aac tgg tac gtg gac ggc gtg gag gtg cat<br>Asp Pro Glu Val Lys Phe Asn Trp Tyr Val Asp Gly Val Glu Val His<br>485 490 495 | 1488 | |
| aat gcc aag aca aag ccg cgg gag gag cag tac aac agc acg tac cgt<br>Asn Ala Lys Thr Lys Pro Arg Glu Glu Gln Tyr Asn Ser Thr Tyr Arg<br>500 505 510 | 1536 | |
| gtg gtc agc gtc ctc acc gtc ctg cac cag gac tgg ctg aat ggc aag<br>Val Val Ser Val Leu Thr Val Leu His Gln Asp Trp Leu Asn Gly Lys<br>515 520 525 | 1584 | |
| gag tac aag tgc aag gtc tcc aac aaa gcc ctc cca gcc ccc atc gag<br>Glu Tyr Lys Cys Lys Val Ser Asn Lys Ala Leu Pro Ala Pro Ile Glu<br>530 535 540 | 1632 | |
| aaa acc atc tcc aaa gcc aaa ggg cag ccc cga gaa cca cag gtg tac<br>Lys Thr Ile Ser Lys Ala Lys Gly Gln Pro Arg Glu Pro Gln Val Tyr<br>545 550 555 560 | 1680 | |
| acc ctg ccc cca tcc cgg gat gag ctg acc aag aac cag gtc agc ctg<br>Thr Leu Pro Pro Ser Arg Asp Glu Leu Thr Lys Asn Gln Val Ser Leu<br>565 570 575 | 1728 | |
| acc tgc ctg gtc aaa ggc ttc tat ccc agc gac atc gcc gtg gag tgg<br>Thr Cys Leu Val Lys Gly Phe Tyr Pro Ser Asp Ile Ala Val Glu Trp<br>580 585 590 | 1776 | |

-continued

```
gag agc aat ggg cag ccg gag aac aac tac aag acc acg cct ccc gtg      1824
Glu Ser Asn Gly Gln Pro Glu Asn Asn Tyr Lys Thr Thr Pro Pro Val
            595                 600                 605 ctg gac tcc gac ggc tcc ttc ttc ctc tac agc aag ctc acc gtg gac      1872
Leu Asp Ser Asp Gly Ser Phe Phe Leu Tyr Ser Lys Leu Thr Val Asp
610                 615                 620 aag agc agg tgg cag cag ggg aac gtc ttc tca tgc tcc gtg atg cat      1920
Lys Ser Arg Trp Gln Gln Gly Asn Val Phe Ser Cys Ser Val Met His
625                 630                 635                 640 gag gct ctg cac aac cac tac acg cag aag agc ctc tcc ctg tct ccg      1968
Glu Ala Leu His Asn His Tyr Thr Gln Lys Ser Leu Ser Leu Ser Pro
                645                 650                 655 ggt aaa tga                                                          1977
Gly Lys <210> SEQ ID NO 12
<211> LENGTH: 658
<212> TYPE: PRT
<213> ORGANISM: Artificial Sequence
<220> FEATURE:
<223> OTHER INFORMATION: Homo Sapier Fusion Protein

<400> SEQUENCE: 12

Met Ala Met Ala Arg Ser Arg Arg Asp Ser Val Trp Lys Tyr Cys Trp
1               5                   10                  15

Gly Leu Leu Met Val Leu Cys Arg Thr Ala Ile Ser Arg Ser Ile Val
            20                  25                  30

Leu Glu Pro Ile Tyr Trp Asn Ser Ser Asn Ser Lys Phe Leu Pro Gly
        35                  40                  45

Gln Gly Leu Val Leu Tyr Pro Gln Ile Gly Asp Lys Leu Asp Ile Ile
    50                  55                  60

Cys Pro Lys Val Asp Ser Lys Thr Val Gly Gln Tyr Glu Tyr Tyr Lys
65                  70                  75                  80

Val Tyr Met Val Asp Lys Asp Gln Ala Asp Arg Cys Thr Ile Lys Lys
                85                  90                  95

Glu Asn Thr Pro Leu Leu Asn Cys Ala Arg Pro Asp Gln Asp Val Lys
            100                 105                 110

Phe Thr Ile Lys Phe Gln Glu Phe Ser Pro Asn Leu Trp Gly Leu Glu
        115                 120                 125

Phe Gln Lys Asn Lys Asp Tyr Tyr Ile Ile Ser Thr Ser Asn Gly Ser
    130                 135                 140

Leu Glu Gly Leu Asp Asn Gln Glu Gly Gly Val Cys Gln Thr Arg Ala
145                 150                 155                 160

Met Lys Ile Leu Met Lys Val Gly Gln Asp Ala Ser Ser Ala Gly Ser
                165                 170                 175

Ala Arg Asn His Gly Pro Thr Arg Arg Pro Glu Leu Glu Ala Gly Thr
            180                 185                 190

Asn Gly Arg Ser Ser Thr Thr Ser Pro Phe Val Lys Pro Asn Pro Gly
        195                 200                 205

Ser Ser Thr Asp Gly Asn Ser Ala Gly His Ser Gly Asn Asn Leu Leu
    210                 215                 220

Gly Gly Pro Gly Ile Val Leu Glu Pro Ile Tyr Trp Asn Ser Ser Asn
225                 230                 235                 240

Ser Lys Phe Leu Pro Gly Gln Gly Leu Val Leu Tyr Pro Gln Ile Gly
                245                 250                 255

Asp Lys Leu Asp Ile Ile Cys Pro Lys Val Asp Ser Lys Thr Val Gly
            260                 265                 270
```

-continued

```
Gln Tyr Glu Tyr Tyr Lys Val Tyr Met Val Asp Lys Asp Gln Ala Asp
            275                 280                 285
Arg Cys Thr Ile Lys Lys Glu Asn Thr Pro Leu Leu Asn Cys Ala Arg
        290                 295                 300
Pro Asp Gln Asp Val Lys Phe Thr Ile Lys Phe Gln Glu Phe Ser Pro
305                 310                 315                 320
Asn Leu Trp Gly Leu Glu Phe Gln Lys Asn Lys Asp Tyr Tyr Ile Ile
                325                 330                 335
Ser Thr Ser Asn Gly Ser Leu Glu Gly Leu Asp Asn Gln Glu Gly Gly
            340                 345                 350
Val Cys Gln Thr Arg Ala Met Lys Ile Leu Met Lys Val Gly Gln Asp
        355                 360                 365
Ala Ser Ser Ala Gly Ser Ala Arg Asn His Gly Pro Thr Arg Arg Pro
    370                 375                 380
Glu Leu Glu Ala Gly Thr Asn Gly Arg Ser Ser Thr Thr Ser Pro Phe
385                 390                 395                 400
Val Lys Pro Asn Pro Gly Ser Ser Thr Asp Gly Asn Ser Ala Gly His
                405                 410                 415
Ser Gly Asn Asn Leu Leu Gly Gly Pro Gly Glu Pro Lys Ser Cys Asp
            420                 425                 430
Lys Thr His Thr Cys Pro Pro Cys Pro Ala Pro Glu Leu Leu Gly Gly
        435                 440                 445
Pro Ser Val Phe Leu Phe Pro Pro Lys Pro Lys Asp Thr Leu Met Ile
    450                 455                 460
Ser Arg Thr Pro Glu Val Thr Cys Val Val Val Asp Val Ser His Glu
465                 470                 475                 480
Asp Pro Glu Val Lys Phe Asn Trp Tyr Val Asp Gly Val Glu Val His
                485                 490                 495
Asn Ala Lys Thr Lys Pro Arg Glu Glu Gln Tyr Asn Ser Thr Tyr Arg
            500                 505                 510
Val Val Ser Val Leu Thr Val Leu His Gln Asp Trp Leu Asn Gly Lys
        515                 520                 525
Glu Tyr Lys Cys Lys Val Ser Asn Lys Ala Leu Pro Ala Pro Ile Glu
    530                 535                 540
Lys Thr Ile Ser Lys Ala Lys Gly Gln Pro Arg Glu Pro Gln Val Tyr
545                 550                 555                 560
Thr Leu Pro Pro Ser Arg Asp Glu Leu Thr Lys Asn Gln Val Ser Leu
                565                 570                 575
Thr Cys Leu Val Lys Gly Phe Tyr Pro Ser Asp Ile Ala Val Glu Trp
            580                 585                 590
Glu Ser Asn Gly Gln Pro Glu Asn Asn Tyr Lys Thr Thr Pro Pro Val
        595                 600                 605
Leu Asp Ser Asp Gly Ser Phe Phe Leu Tyr Ser Lys Leu Thr Val Asp
    610                 615                 620
Lys Ser Arg Trp Gln Gln Gly Asn Val Phe Ser Cys Ser Val Met His
625                 630                 635                 640
Glu Ala Leu His Asn His Tyr Thr Gln Lys Ser Leu Ser Leu Ser Pro
                645                 650                 655
Gly Lys

<210> SEQ ID NO 13
<211> LENGTH: 4
<212> TYPE: PRT
```

```
<213> ORGANISM: Homo sapiens

<400> SEQUENCE: 13

Gly Pro Ala Pro
1

<210> SEQ ID NO 14
<211> LENGTH: 5
<212> TYPE: PRT
<213> ORGANISM: Homo sapiens

<400> SEQUENCE: 14

Gly Gly Pro Ala Pro
1               5

<210> SEQ ID NO 15
<211> LENGTH: 8
<212> TYPE: PRT
<213> ORGANISM: Homo sapiens

<400> SEQUENCE: 15

Gly Gly Gly Gly Ser Gly Ala Pro
1               5

<210> SEQ ID NO 16
<211> LENGTH: 4
<212> TYPE: PRT
<213> ORGANISM: Homo sapiens

<400> SEQUENCE: 16

Gly Gly Pro Gly
1

<210> SEQ ID NO 17
<211> LENGTH: 5
<212> TYPE: PRT
<213> ORGANISM: Homo sapiens

<400> SEQUENCE: 17

Arg Asp Cys Ala Asp
1               5

<210> SEQ ID NO 18
<211> LENGTH: 5
<212> TYPE: PRT
<213> ORGANISM: Homo sapiens

<400> SEQUENCE: 18

Arg Asp Cys Ala Glu
1               5

<210> SEQ ID NO 19
<211> LENGTH: 5
<212> TYPE: PRT
<213> ORGANISM: Homo sapiens

<400> SEQUENCE: 19

Asp Cys Ala Glu Val
1               5
```